United States Patent
Yanai et al.

(10) Patent No.: US 7,432,102 B2
(45) Date of Patent: *Oct. 7, 2008

(54) TRANSFORMANTS PRODUCING SUBSTANCE PF1022 DERIVATIVES, METHODS FOR PRODUCING THE SAME, AND NOVEL BIOSYNTHESIS GENES

(75) Inventors: Koji Yanai, Odawara (JP); Naomi Sumida, Odawara (JP); Manabu Watanabe, Odawara (JP); Tatsuki Moriya, Odawara (JP); Takeshi Murakami, Odawara (JP)

(73) Assignee: Meiji Seika Kaisha, Ltd., Tokyo-To (JP)

( * ) Notice: Subject to any disclaimer, the term of this patent is extended or adjusted under 35 U.S.C. 154(b) by 336 days.

This patent is subject to a terminal disclaimer.

(21) Appl. No.: 10/472,587

(22) PCT Filed: Mar. 22, 2002

(86) PCT No.: PCT/JP02/02782

§ 371 (c)(1),
(2), (4) Date: Sep. 22, 2003

(87) PCT Pub. No.: WO02/077244

PCT Pub. Date: Oct. 3, 2002

(65) Prior Publication Data

US 2004/0214274 A1    Oct. 28, 2004

(30) Foreign Application Priority Data

Mar. 22, 2001    (JP)    .............................. 2001-082227

(51) Int. Cl.
- *C12N 1/00* (2006.01)
- *C12P 1/00* (2006.01)
- *C12P 17/00* (2006.01)
- *C12P 15/00* (2006.01)
- *C12P 13/00* (2006.01)
- *C12P 7/00* (2006.01)
- *C12P 7/24* (2006.01)
- *C12P 1/02* (2006.01)

(52) U.S. Cl. .................... 435/254.11; 435/41; 435/117; 435/127; 435/128; 435/132; 435/147; 435/171

(58) Field of Classification Search ........................ None
See application file for complete search history.

(56) References Cited

U.S. PATENT DOCUMENTS 5,763,221 A * 6/1998 Aoyagi et al. .............. 435/69.1
7,109,018 B1 * 9/2006 Yanai et al. .............. 435/252.3

FOREIGN PATENT DOCUMENTS

| EP | 0 382 173 | 8/1990 |
| WO | 01/23542 | 4/2001 |

OTHER PUBLICATIONS

Weckwerth et al., J. Biol. Chem., vol. 275, pp. 17909-17915, 2000.*
Witkowski et al. Biochemistry, vol. 38, pp. 11643-11650, 1999.*
V. Blanc et al., "Identification and analysis of genes from *Streptomyces pristinaespiralis* encoding enzymes involved in the biosynthesis of the 4-dimethylamino-L-phenylalanine precursor of pristinamycin I", Molecuarl Microbiology, vol. 23, No. 2, pp. 191-202, 1997.
W. Weckwerth et al., "Biosynthesis of PF1022A and related cyclooctadepsipeptides", The Journal of Biological Chemistry, vol. 275, No. 23, pp. 17909-17915, Jun. 9, 2000.
K. Yanai et al., "*Para*-position derivatives of fungal anthelmintic cyclodepsipeptides engineered with *Streptomyces venezuelae* antibiotic biosynthetic genes", Nature Biotechnology, vol. 22, No. 7, pp. 848-855, Jul. 2004.
J. Eberhard et al., "Cloning and expression in yeast of a higher plant chorismate mutase molecular cloning, sequencing of the cDNA and characterization of the *Arabidopsis thaliana* enzyme expressed in yeast", FEBS Letters, vol. 334, No. 2, pp. 233-236, Nov. 1993.
T. Schmidheini et al., "A single point mutation results in a constitutively activated and feedback-resistant chorismate mutase of *Saccharomyces cerevisiae*", Journal of Bacteriology, vol. 171, No. 3, pp. 1245-1253, Mar. 1989.
S. Krappmann et al., "The aroC gene of *Aspergillus nidulans* codes for a monofunctional, allosterically regulated chorismate mutase", The Journal of Biological Chemistry, vol. 274, No. 32, pp. 22275-22282, Aug. 6, 1999.

(Continued)

*Primary Examiner*—Kathleen Kerr Bragdon
*Assistant Examiner*—Jae W Lee
(74) *Attorney, Agent, or Firm*—Wenderoth, Lind & Ponack, L.L.P.

(57) ABSTRACT

An objective of the present invention is to provide a method for producing substance PF1022 derivatives, in particular PF1022-220 and PF1022-260, by a direct fermentation method, and a transformant to be used for this method. According to the present invention, there is provided a transformant producing substance FF1022 derivatives, which can be obtained by introducing a genes involved in a biosynthetic pathway from chorismic acid to p-aminophenylpyruvic acid, including a papA gene encoding 4-amino-4-deoxychorismate synthase. which gene comprises the DNA sequence encoding the amino acid sequence of SEQ ID NO: 2; a papB gene encoding 4-amino-4-deoxyclaismate mutase, which gene comprises the DNA sequence encoding the amino acid sequence of SEQ ID NO: 4; and a papC gene encoding 4-amino-4-deoxyprepbenate dehydrogenase, which gene comprises the DNA sequence encoding the amino acid sequence of SEQ ID NO: 6, into a phenylalanine auxotrophic host induced from an organism that produces a substance PF1022. According to the present invention, there is also provided a process of producing substance PF1022 derivative, comprising steps of culturing the above-mentioned transformant and collecting the substance PF1022 derivatives.

9 Claims, 21 Drawing Sheets

OTHER PUBLICATIONS

R. S. Fischer et al., "Cloning, sequencing, and expression of the P-protein gene (*pheA*) of *Pseudomonas stutzeri* in *Escherichia coli*: implications for evolutionary relationships in phenylalanine biosynthesis", Journal of General Microbiology, vol. 137, No. 6, pp. 1293-1301, Jun. 1991.

Database UniProt, Oct. 1, 1993, "Prephenate dehydratase" XP002332551 retrieved from EBI Accession No. UniProt: PHA2_Yeast, Database Accession No. PHA2_Yeast.

Database UniProt, Jun. 1, 1998, "SPBC30D10.16", XP002332638 retrieved from EBI Accession No. 014361_SCHPO, Database Accession No. 014361.

* cited by examiner

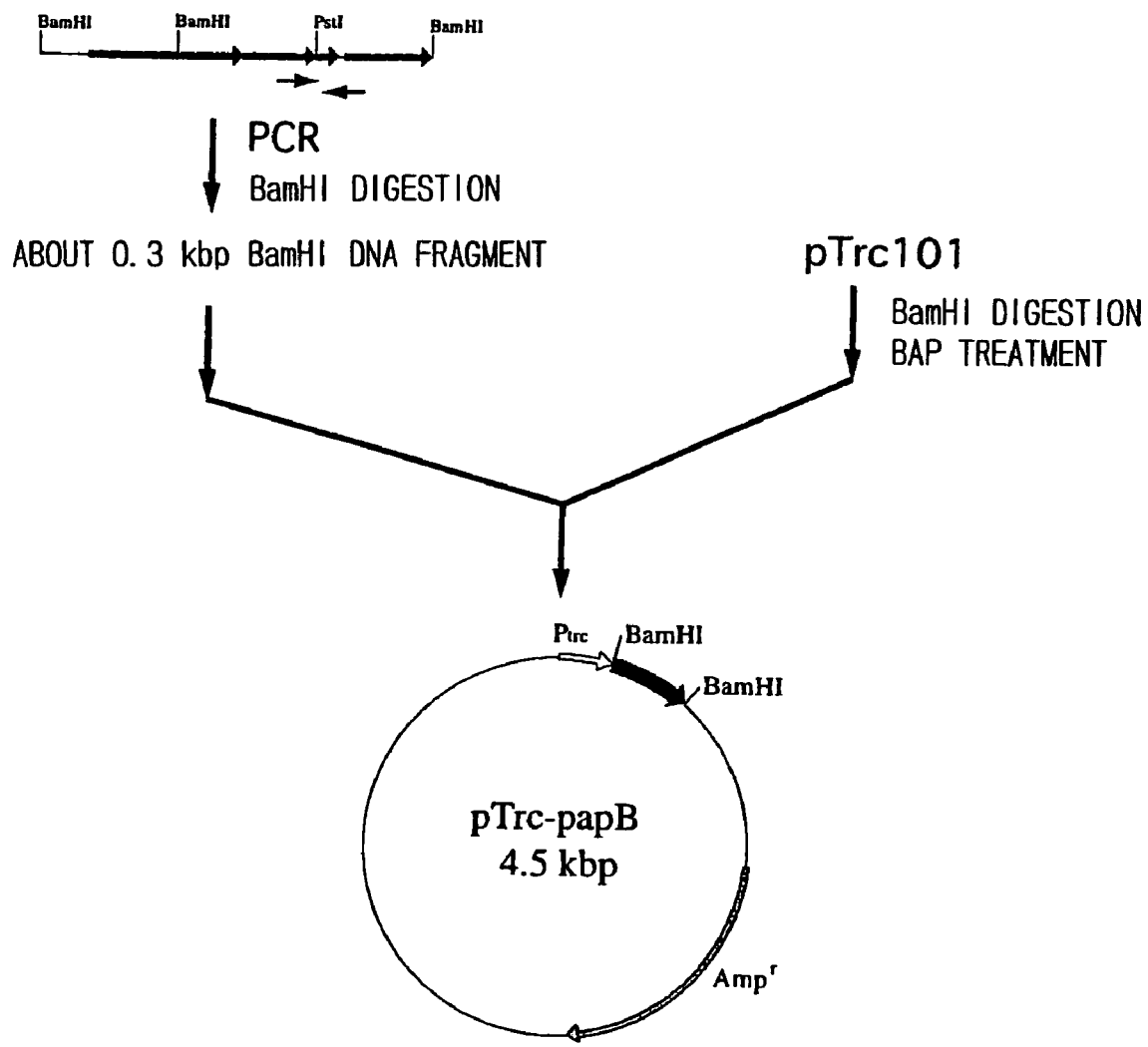
F I G. 4

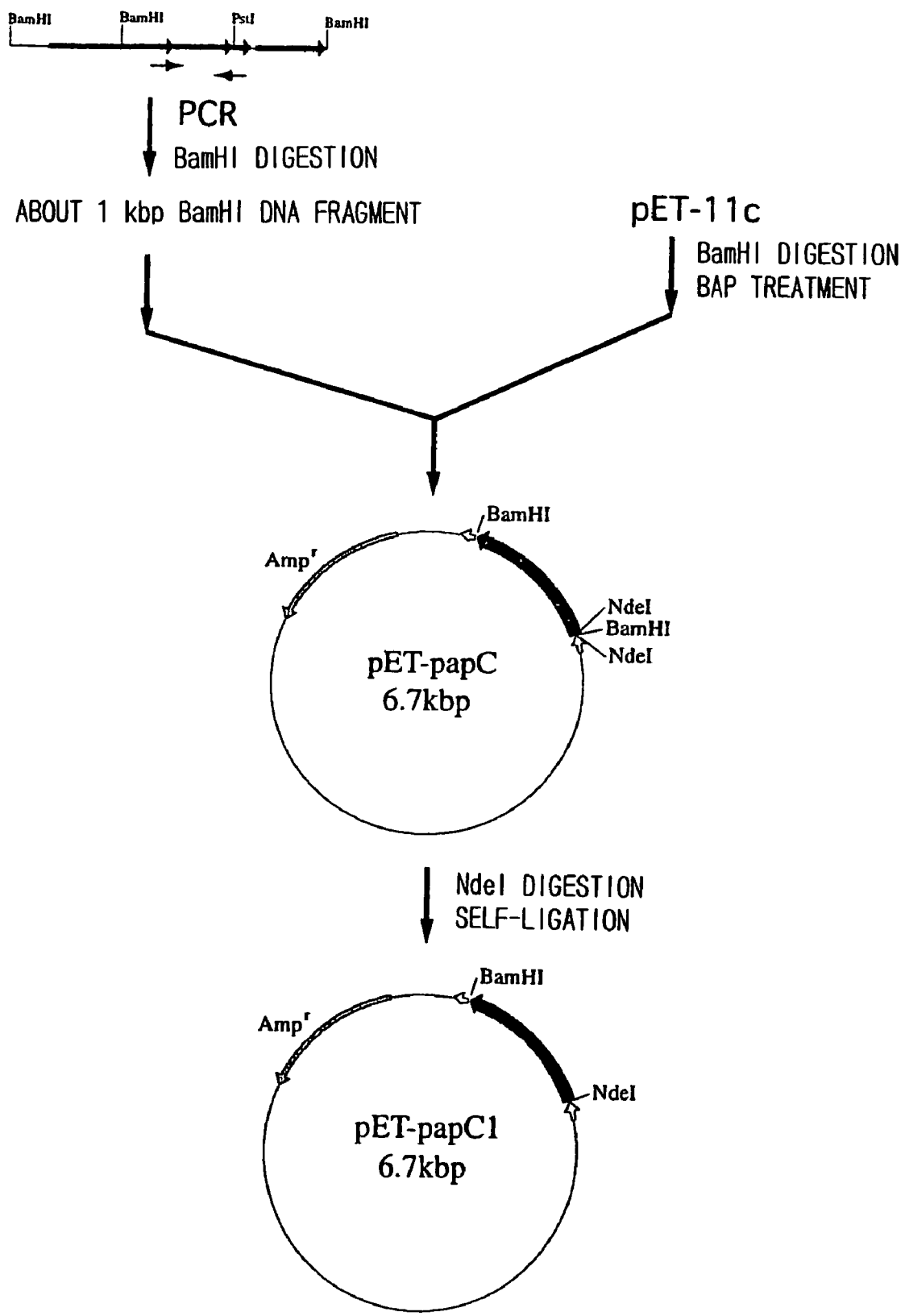
F I G. 6

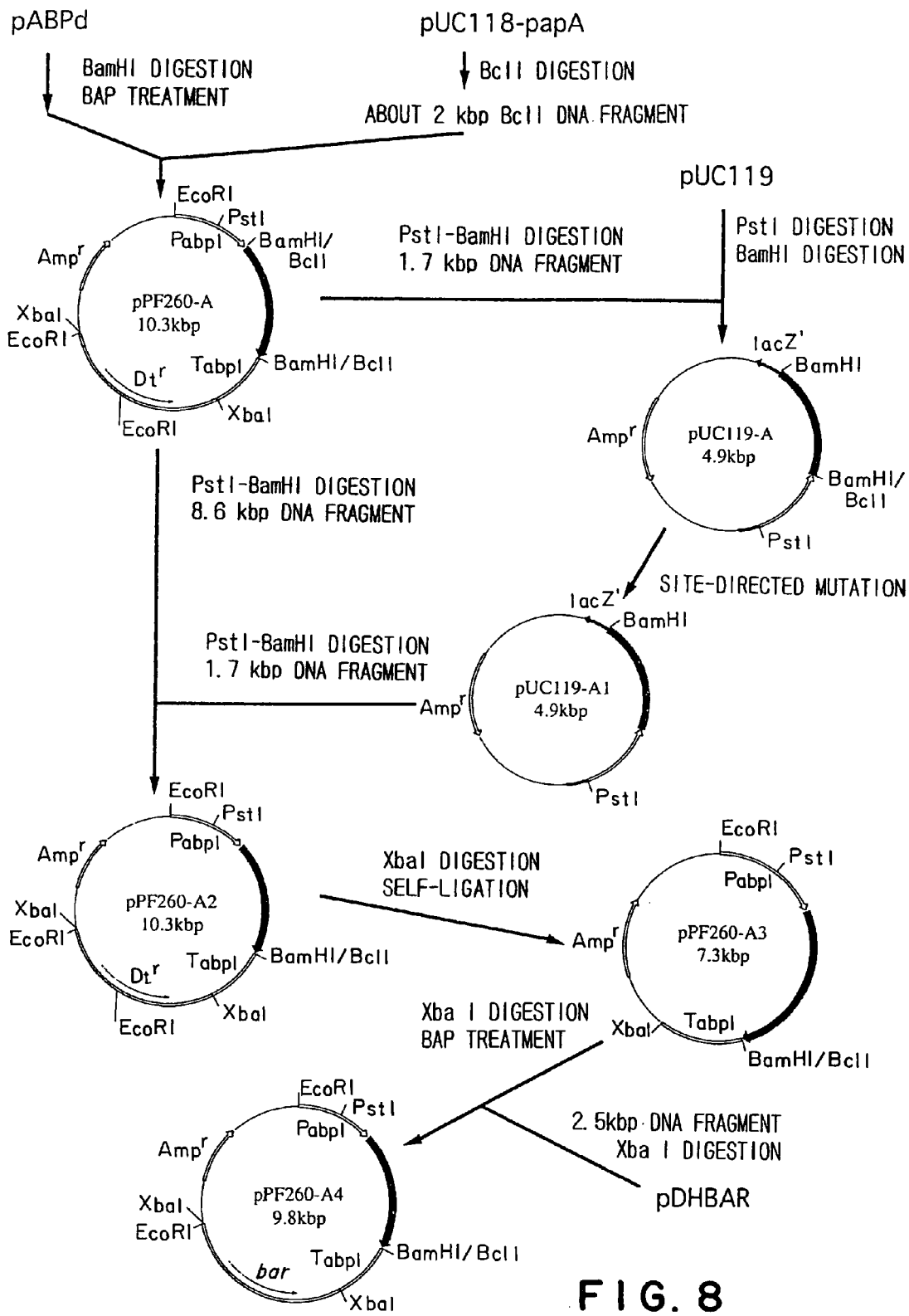
F I G. 8

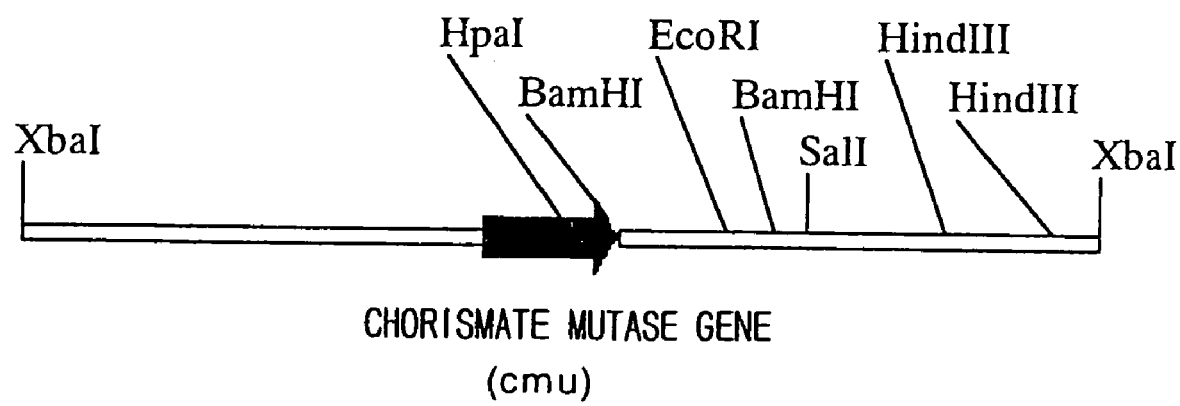
F I G. 13

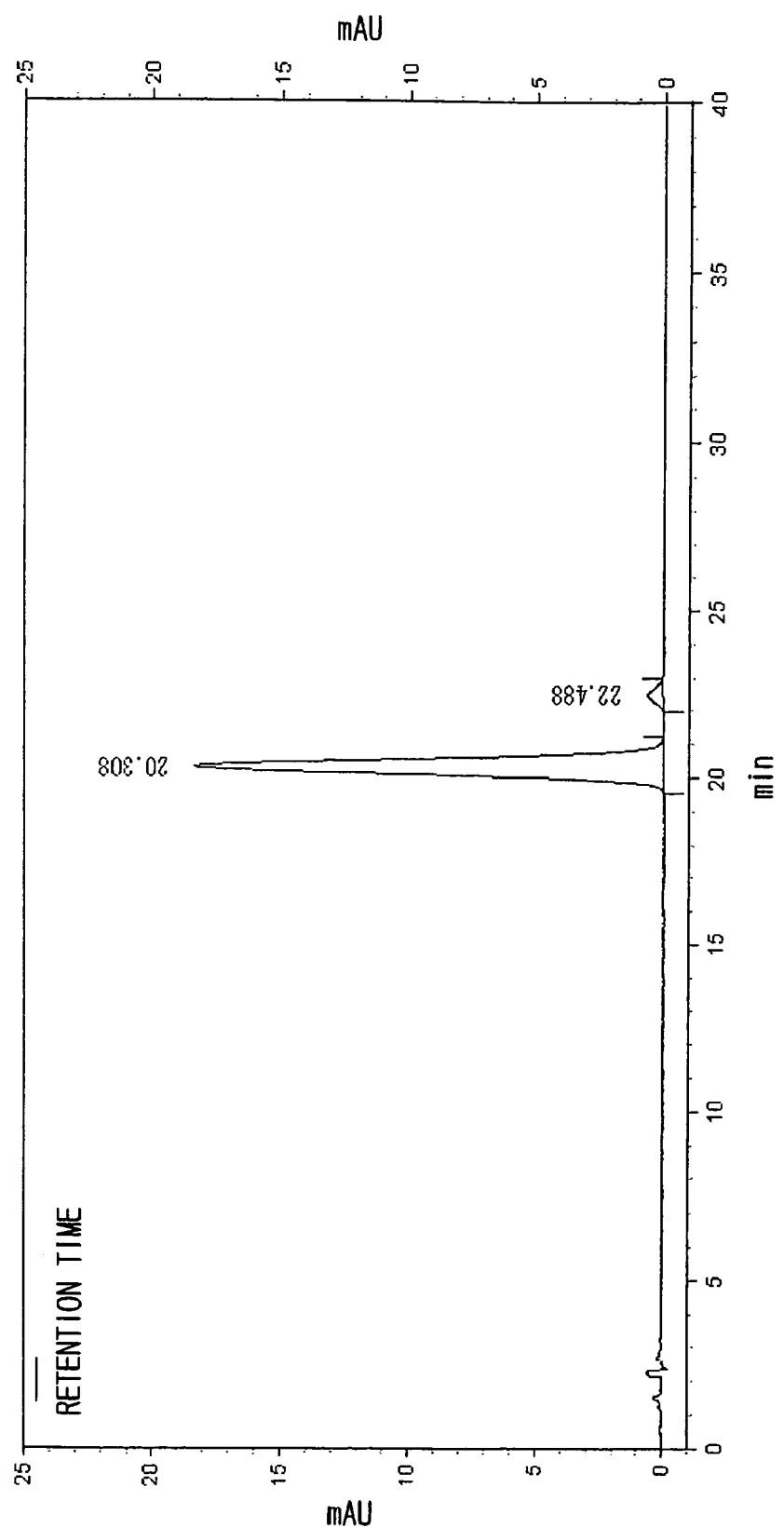
(A) CHROMATOGRAM FOR STANDARD PF1022-220

(B) CHROMATOGRAM FOR SAMPLE FROM TRANSFORMANT (C) CHROMATOGRAM FOR SAMPLE FROM TRANSFORMANT AND STANDARD PF1022-220

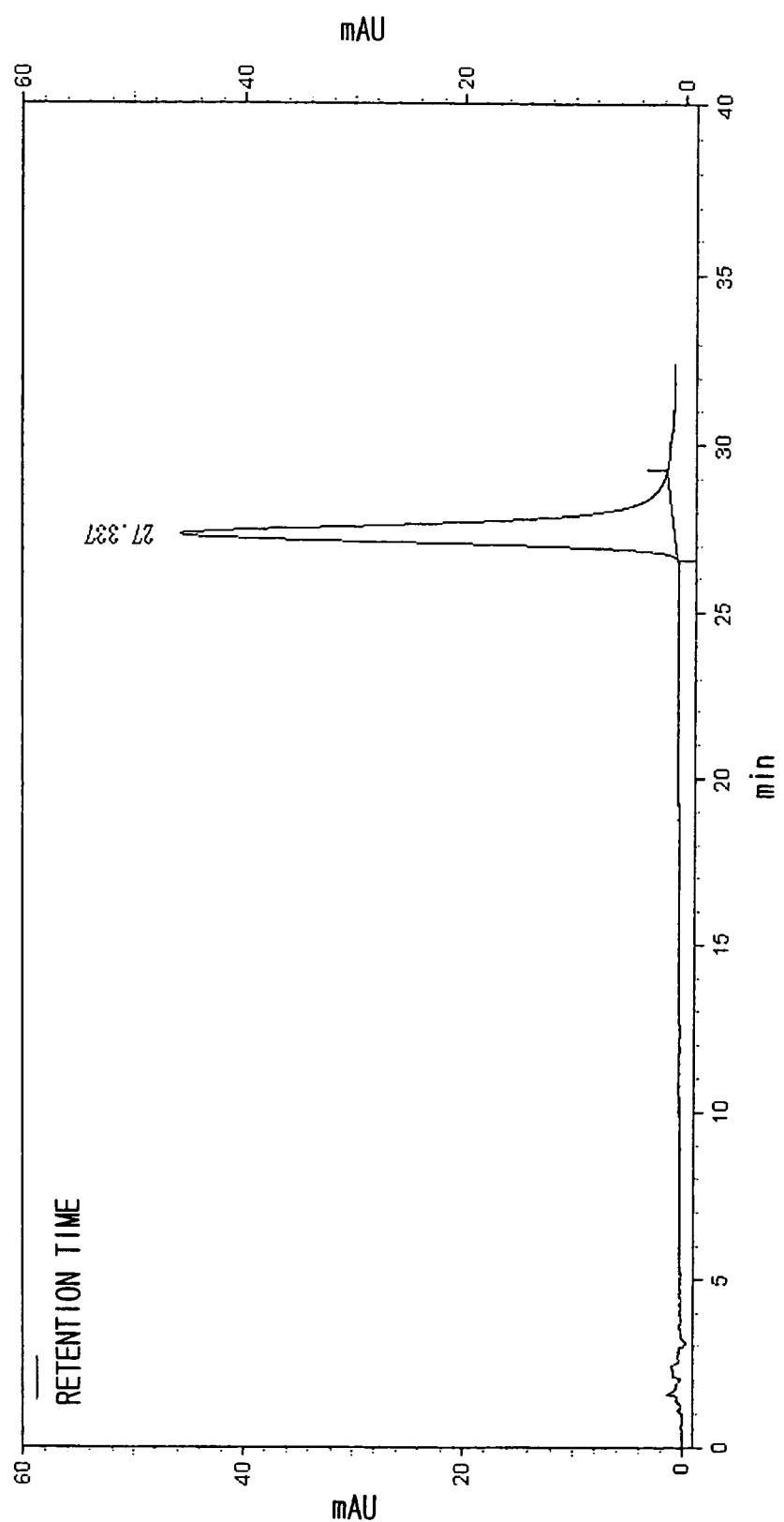
(A) CHROMATOGRAM FOR STANDARD PF1022-260

(B) CHROMATOGRAM FOR SAMPLE FROM TRANSFORMANT

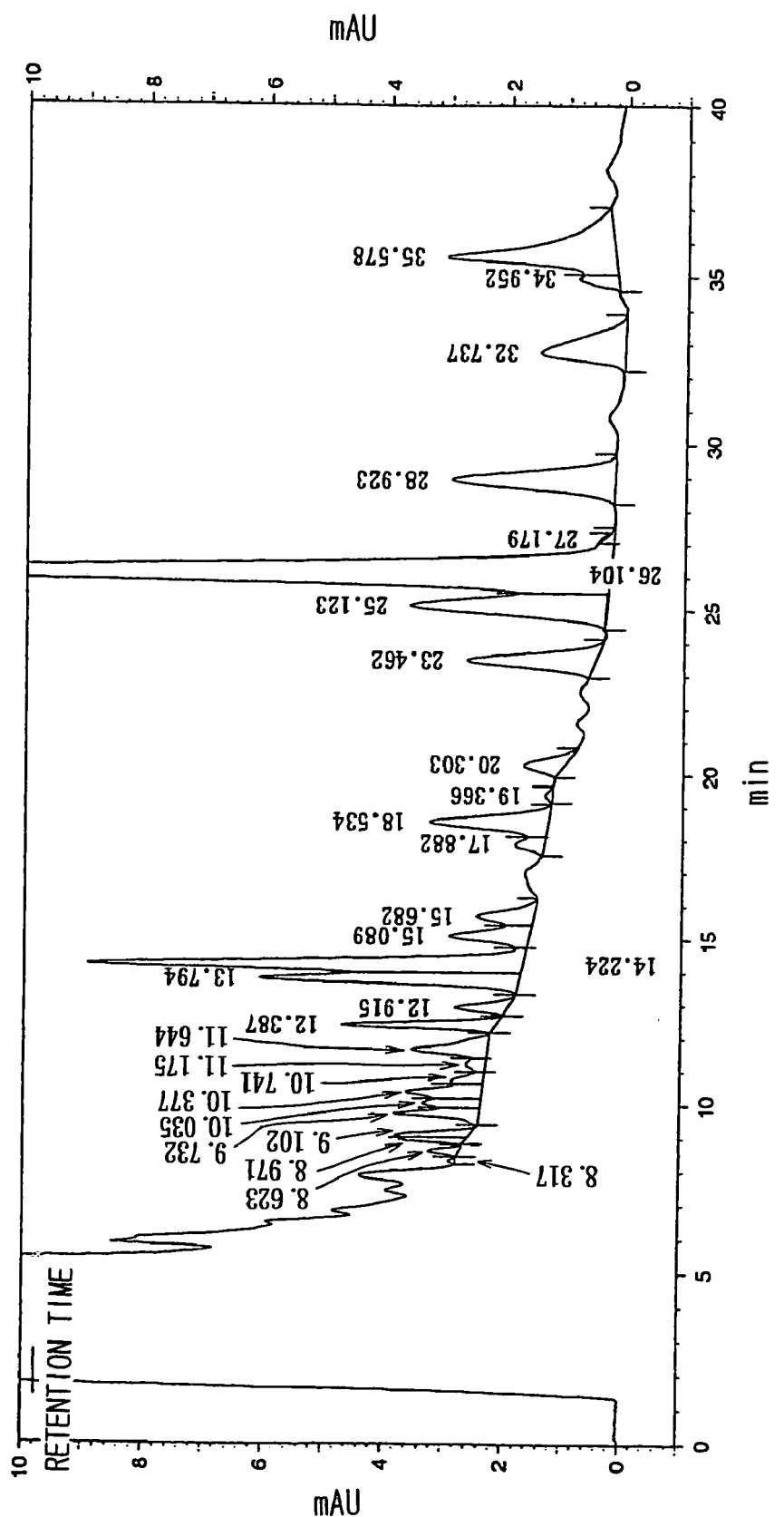
(A) CHROMATOGRAM FOR SAMPLE FROM STRAIN TF-57

(B) CHROMATOGRAM FOR SAMPLE FROM STRAIN TF-45

SEQUENCE LISTING

<160> NUMBER OF SEQ ID NOS: 40

<210> SEQ ID NO 1
<211> LENGTH: 2061
<212> TYPE: DNA
<213> ORGANISM: Streptomyces venezuelae
<220> FEATURE:
<221> NAME/KEY: CDS
<222> LOCATION: (1)..(2058)

<400> SEQUENCE: 1

```
atg cgc acg ctt ctg atc gac aac tac gac tcg ttc acc cac aac ctg      48
Met Arg Thr Leu Leu Ile Asp Asn Tyr Asp Ser Phe Thr His Asn Leu
 1               5                  10                  15 ttc cag tac atc ggc gag gcc acc ggg caa ccc ccc gtc gtc gtg ccc      96
Phe Gln Tyr Ile Gly Glu Ala Thr Gly Gln Pro Pro Val Val Val Pro
             20                  25                  30 aac gac gcc gac tgg tcg cgg ctg ccc gtc gag gac ttc gac gcg atc     144
Asn Asp Ala Asp Trp Ser Arg Leu Pro Val Glu Asp Phe Asp Ala Ile
         35                  40                  45 gtc gtg tcc ccg ggc ccc ggc agc ccc gac cgg gaa cgg gac ttc gga     192
Val Val Ser Pro Gly Pro Gly Ser Pro Asp Arg Glu Arg Asp Phe Gly
     50                  55                  60
```

```
                                                                    -continued atc agc cgc cgg gcg atc acc gac agc ggc ctg ccc gtc ctc ggc gtc      240
Ile Ser Arg Arg Ala Ile Thr Asp Ser Gly Leu Pro Val Leu Gly Val
 65              70                  75                  80 tgc ctc ggc cac cag ggc atc gcc cag ctc ttc ggc gga acc gtc ggc      288
Cys Leu Gly His Gln Gly Ile Ala Gln Leu Phe Gly Gly Thr Val Gly
             85                  90                  95 ctc gcc ccg gaa ccc atg cac ggc cgg gtc tcc gag gtg cgg cac acc      336
Leu Ala Pro Glu Pro Met His Gly Arg Val Ser Glu Val Arg His Thr
        100                 105                 110 ggc gag gac gtc ttc cgg ggc ctc ccc tcg ccg ttc acc gcc gtg cgc      384
Gly Glu Asp Val Phe Arg Gly Leu Pro Ser Pro Phe Thr Ala Val Arg
    115                 120                 125 tac cac tcc ctg gcc gcc acc gac ctc ccc gac gag ctc gaa ccc ctc      432
Tyr His Ser Leu Ala Ala Thr Asp Leu Pro Asp Glu Leu Glu Pro Leu
130                 135                 140 gcc tgg agc gac gac ggg gtc gtc atg ggc ctg cgg cac cgc gag aag      480
Ala Trp Ser Asp Asp Gly Val Val Met Gly Leu Arg His Arg Glu Lys
145                 150                 155                 160 ccg ctg tgg ggc gtc cag ttc cac ccg gag tcc atc ggc agc gac ttc      528
Pro Leu Trp Gly Val Gln Phe His Pro Glu Ser Ile Gly Ser Asp Phe
                165                 170                 175 ggc cgg gag atc atg gcc aac ttc cgc gac ctc gcc ctc gcc cac cac      576
Gly Arg Glu Ile Met Ala Asn Phe Arg Asp Leu Ala Leu Ala His His
            180                 185                 190 cgg gca cgg cgc cac ggg gcc gac tcc ccg tac gaa ctc cac gtg cgc      624
Arg Ala Arg Arg His Gly Ala Asp Ser Pro Tyr Glu Leu His Val Arg
        195                 200                 205 cgc gtc gac gtg ctg ccg gac gcc gaa gag gta cgc cgc ggc tgc ctg      672
Arg Val Asp Val Leu Pro Asp Ala Glu Glu Val Arg Arg Gly Cys Leu
    210                 215                 220 ccc ggc gag ggc acc acg ttc tgg ctg gac agc agc tcc gtc ctc gaa      720
Pro Gly Glu Gly Thr Thr Phe Trp Leu Asp Ser Ser Ser Val Leu Glu
225                 230                 235                 240 ggc gcc tcg cgc ttc tcc ttc ctc ggc gac gac cgc ggc ccg ctc gcc      768
Gly Ala Ser Arg Phe Ser Phe Leu Gly Asp Asp Arg Gly Pro Leu Ala
                245                 250                 255 gag tac ctc acc tac cgc gtc gcc gac ggc gtc gtc tcc gtc cgc ggc      816
Glu Tyr Leu Thr Tyr Arg Val Ala Asp Gly Val Val Ser Val Arg Gly
            260                 265                 270 tcc gac ggc acc acg acc cgg acg cgg cgc ccc ttc ttc aac tac ctg      864
Ser Asp Gly Thr Thr Thr Arg Thr Arg Arg Pro Phe Phe Asn Tyr Leu
        275                 280                 285 gag gag cag ctc gaa cgc cga cgg gtc ccc gtc gcc ccc gaa ctg ccc      912
Glu Glu Gln Leu Glu Arg Arg Arg Val Pro Val Ala Pro Glu Leu Pro
    290                 295                 300 ttc gag ttc aac ctc ggc tac gtc ggc tac ctc ggc tac gag ctg aag      960
Phe Glu Phe Asn Leu Gly Tyr Val Gly Tyr Leu Gly Tyr Glu Leu Lys
305                 310                 315                 320 gcg gag acc acc ggc gac ccc gcg cac cgg tcc ccg cac ccc gac gcc     1008
Ala Glu Thr Thr Gly Asp Pro Ala His Arg Ser Pro His Pro Asp Ala
                325                 330                 335 gcg ttc ctc ttc gcc gac cgc gcc atc gcc ctc gac cac cag gaa ggc     1056
Ala Phe Leu Phe Ala Asp Arg Ala Ile Ala Leu Asp His Gln Glu Gly
            340                 345                 350 tgc tgc tac ctg ctg gcc ctc gac cgc ggg cac gac gac ggc gcc         1104
Cys Cys Tyr Leu Leu Ala Leu Asp Arg Gly His Asp Asp Gly Ala
        355                 360                 365 cgc gcc tgg ctg cgg gag acg gcc gag acc ctc acc ggc ctg gcc gtc     1152
Arg Ala Trp Leu Arg Glu Thr Ala Glu Thr Leu Thr Gly Leu Ala Val
```

-continued

```
              370                 375                 380
cgc gcc ccg gcc gag ccg acc ccc gcc atg gtc ttc ggg atc ccc gag      1200
Arg Ala Pro Ala Glu Pro Thr Pro Ala Met Val Phe Gly Ile Pro Glu
385                 390                 395                 400 gcg gcg gcc ggc ttc ggc ccc ctg gcc cgc gcg cgc cac gac aag gac      1248
Ala Ala Ala Gly Phe Gly Pro Leu Ala Arg Ala Arg His Asp Lys Asp
                405                 410                 415 gcc tac ctc aag cgc atc gac gag tgc ctc aag gag atc cgc aac ggc      1296
Ala Tyr Leu Lys Arg Ile Asp Glu Cys Leu Lys Glu Ile Arg Asn Gly
        420                 425                 430 gag tcg tac gag atc tgc ctg acc aac atg gtc acc gcg ccc acc gag      1344
Glu Ser Tyr Glu Ile Cys Leu Thr Asn Met Val Thr Ala Pro Thr Glu
            435                 440                 445 gcg acg gcc ctg ccg ctc tac tcc gcg ctg cgc gcc atc agc ccc gtc      1392
Ala Thr Ala Leu Pro Leu Tyr Ser Ala Leu Arg Ala Ile Ser Pro Val
        450                 455                 460 ccg tac ggc gcc ctg ctc gag ttc ccc gaa ctg tcg gtg ctg agc gcc      1440
Pro Tyr Gly Ala Leu Leu Glu Phe Pro Glu Leu Ser Val Leu Ser Ala
465                 470                 475                 480 tcg ccc gag cgg ttc ctc acg atc ggc gcc gac ggc ggc gtc gag tcc      1488
Ser Pro Glu Arg Phe Leu Thr Ile Gly Ala Asp Gly Gly Val Glu Ser
                485                 490                 495 aag ccc atc aag ggg acc cgc ccc cgg ggc ggc acc gcg gag gag gac      1536
Lys Pro Ile Lys Gly Thr Arg Pro Arg Gly Gly Thr Ala Glu Glu Asp
        500                 505                 510 gag cgg ctc cgc gcc gac ctg gcc ggc cgg gag aag gac cgg gcc gag      1584
Glu Arg Leu Arg Ala Asp Leu Ala Gly Arg Glu Lys Asp Arg Ala Glu
            515                 520                 525 aac ctg atg atc gtc gac ctg gtc cgc aac gac ctc aac agc gtc tgc      1632
Asn Leu Met Ile Val Asp Leu Val Arg Asn Asp Leu Asn Ser Val Cys
        530                 535                 540 gcg atc ggc tcc gtc cac gtg ccc cgg ctc ttc gag gtg gag acc tac      1680
Ala Ile Gly Ser Val His Val Pro Arg Leu Phe Glu Val Glu Thr Tyr
545                 550                 555                 560 gcg ccc gtg cac cag ctg gtg tcg acc atc cgg gga cgg ctg cgg ccc      1728
Ala Pro Val His Gln Leu Val Ser Thr Ile Arg Gly Arg Leu Arg Pro
                565                 570                 575 ggc acc agc acc gcc gcc tgc gta cgc gcc gcc ttc ccc ggc ggc tcc      1776
Gly Thr Ser Thr Ala Ala Cys Val Arg Ala Ala Phe Pro Gly Gly Ser
        580                 585                 590 atg acc ggc gcg ccc aag aag cgc acc atg gag atc atc gac cgc ctg      1824
Met Thr Gly Ala Pro Lys Lys Arg Thr Met Glu Ile Ile Asp Arg Leu
            595                 600                 605 gag gaa ggc ccc cgg ggc gtc tac tcc ggg gcg ctc gga tgg ttc gcc      1872
Glu Glu Gly Pro Arg Gly Val Tyr Ser Gly Ala Leu Gly Trp Phe Ala
        610                 615                 620 ctc agc ggc gcc gcc gac ctc agc atc gtc atc cgc acc atc gtg ctg      1920
Leu Ser Gly Ala Ala Asp Leu Ser Ile Val Ile Arg Thr Ile Val Leu
625                 630                 635                 640 gcc gac ggc cag gcg gag ttc ggc gtc ggg gcg atc gtg tcc ctc          1968
Ala Asp Gly Gln Ala Glu Phe Gly Val Gly Ala Ile Val Ser Leu
                645                 650                 655 tcc gac cag gag gag gag ttc acc gag acc gtg gta aag gcc cgc gcc      2016
Ser Asp Gln Glu Glu Glu Phe Thr Glu Thr Val Val Lys Ala Arg Ala
        660                 665                 670 atg gtc acc gcc ctc gac ggc agc gcc gtg gcg ggc gcc cga tga          2061
Met Val Thr Ala Leu Asp Gly Ser Ala Val Ala Gly Ala Arg
            675                 680                 685
```

<210> SEQ ID NO 2
<211> LENGTH: 686
<212> TYPE: PRT
<213> ORGANISM: Streptomyces venezuelae

<400> SEQUENCE: 2

```
Met Arg Thr Leu Leu Ile Asp Asn Tyr Asp Ser Phe Thr His Asn Leu
  1               5                  10                  15

Phe Gln Tyr Ile Gly Glu Ala Thr Gly Gln Pro Pro Val Val Val Pro
                 20                  25                  30

Asn Asp Ala Asp Trp Ser Arg Leu Pro Val Glu Asp Phe Asp Ala Ile
             35                  40                  45

Val Val Ser Pro Gly Pro Gly Ser Pro Asp Arg Glu Arg Asp Phe Gly
 50                  55                  60

Ile Ser Arg Arg Ala Ile Thr Asp Ser Gly Leu Pro Val Leu Gly Val
 65                  70                  75                  80

Cys Leu Gly His Gln Gly Ile Ala Gln Leu Phe Gly Gly Thr Val Gly
                 85                  90                  95

Leu Ala Pro Glu Pro Met His Gly Arg Val Ser Glu Val Arg His Thr
                100                 105                 110

Gly Glu Asp Val Phe Arg Gly Leu Pro Ser Pro Phe Thr Ala Val Arg
            115                 120                 125

Tyr His Ser Leu Ala Ala Thr Asp Leu Pro Asp Glu Leu Glu Pro Leu
130                 135                 140

Ala Trp Ser Asp Asp Gly Val Val Met Gly Leu Arg His Arg Glu Lys
145                 150                 155                 160

Pro Leu Trp Gly Val Gln Phe His Pro Glu Ser Ile Gly Ser Asp Phe
                165                 170                 175

Gly Arg Glu Ile Met Ala Asn Phe Arg Asp Leu Ala Leu Ala His His
            180                 185                 190

Arg Ala Arg Arg His Gly Ala Asp Ser Pro Tyr Glu Leu His Val Arg
        195                 200                 205

Arg Val Asp Val Leu Pro Asp Ala Glu Glu Val Arg Arg Gly Cys Leu
    210                 215                 220

Pro Gly Glu Gly Thr Thr Phe Trp Leu Asp Ser Ser Ser Val Leu Glu
225                 230                 235                 240

Gly Ala Ser Arg Phe Ser Phe Leu Gly Asp Asp Arg Gly Pro Leu Ala
                245                 250                 255

Glu Tyr Leu Thr Tyr Arg Val Ala Asp Gly Val Val Ser Val Arg Gly
            260                 265                 270

Ser Asp Gly Thr Thr Thr Arg Thr Arg Arg Pro Phe Phe Asn Tyr Leu
        275                 280                 285

Glu Glu Gln Leu Glu Arg Arg Arg Val Pro Val Ala Pro Glu Leu Pro
    290                 295                 300

Phe Glu Phe Asn Leu Gly Tyr Val Gly Tyr Leu Gly Tyr Glu Leu Lys
305                 310                 315                 320

Ala Glu Thr Thr Gly Asp Pro Ala His Arg Ser Pro His Pro Asp Ala
                325                 330                 335

Ala Phe Leu Phe Ala Asp Arg Ala Ile Ala Leu Asp His Gln Glu Gly
            340                 345                 350

Cys Cys Tyr Leu Leu Ala Leu Asp Arg Arg Gly His Asp Asp Gly Ala
        355                 360                 365

Arg Ala Trp Leu Arg Glu Thr Ala Glu Thr Leu Thr Gly Leu Ala Val
    370                 375                 380
```

```
Arg Ala Pro Ala Glu Pro Thr Pro Ala Met Val Phe Gly Ile Pro Glu
385                 390                 395                 400

Ala Ala Ala Gly Phe Gly Pro Leu Ala Arg Ala Arg His Asp Lys Asp
                405                 410                 415

Ala Tyr Leu Lys Arg Ile Asp Glu Cys Leu Lys Glu Ile Arg Asn Gly
            420                 425                 430

Glu Ser Tyr Glu Ile Cys Leu Thr Asn Met Val Thr Ala Pro Thr Glu
        435                 440                 445

Ala Thr Ala Leu Pro Leu Tyr Ser Ala Leu Arg Ala Ile Ser Pro Val
    450                 455                 460

Pro Tyr Gly Ala Leu Leu Glu Phe Pro Glu Leu Ser Val Leu Ser Ala
465                 470                 475                 480

Ser Pro Glu Arg Phe Leu Thr Ile Gly Ala Asp Gly Gly Val Glu Ser
                485                 490                 495

Lys Pro Ile Lys Gly Thr Arg Pro Arg Gly Thr Ala Glu Glu Asp
                500                 505                 510

Glu Arg Leu Arg Ala Asp Leu Ala Gly Arg Glu Lys Asp Arg Ala Glu
            515                 520                 525

Asn Leu Met Ile Val Asp Leu Val Arg Asn Asp Leu Asn Ser Val Cys
530                 535                 540

Ala Ile Gly Ser Val His Val Pro Arg Leu Phe Glu Val Glu Thr Tyr
545                 550                 555                 560

Ala Pro Val His Gln Leu Val Ser Thr Ile Arg Gly Arg Leu Arg Pro
                565                 570                 575

Gly Thr Ser Thr Ala Ala Cys Val Arg Ala Ala Phe Pro Gly Gly Ser
            580                 585                 590

Met Thr Gly Ala Pro Lys Lys Arg Thr Met Glu Ile Ile Asp Arg Leu
        595                 600                 605

Glu Glu Gly Pro Arg Gly Val Tyr Ser Gly Ala Leu Gly Trp Phe Ala
    610                 615                 620

Leu Ser Gly Ala Ala Asp Leu Ser Ile Val Ile Arg Thr Ile Val Leu
625                 630                 635                 640

Ala Asp Gly Gln Ala Glu Phe Gly Val Gly Ala Ile Val Ser Leu
                645                 650                 655

Ser Asp Gln Glu Glu Glu Phe Thr Glu Thr Val Val Lys Ala Arg Ala
            660                 665                 670

Met Val Thr Ala Leu Asp Gly Ser Ala Val Ala Gly Ala Arg
        675                 680                 685

<210> SEQ ID NO 3
<211> LENGTH: 312
<212> TYPE: DNA
<213> ORGANISM: Streptomyces venezuelae
<220> FEATURE:
<221> NAME/KEY: CDS
<222> LOCATION: (1)..(309)

<400> SEQUENCE: 3 atg acc gag cag aac gag ctg cag cgg ctg cgc gcg gag ctc gac gcc    48
Met Thr Glu Gln Asn Glu Leu Gln Arg Leu Arg Ala Glu Leu Asp Ala
  1               5                  10                  15 ctc gac ggg acg ctc ctg gac acg gtg cgg cgc cgc atc gac ctc ggt    96
Leu Asp Gly Thr Leu Leu Asp Thr Val Arg Arg Arg Ile Asp Leu Gly
             20                  25                  30 gtc cgc atc gcg cgg tac aag tcc cgg cac ggc gtc ccg atg atg cag   144
Val Arg Ile Ala Arg Tyr Lys Ser Arg His Gly Val Pro Met Met Gln
         35                  40                  45
```

-continued

```
ccc ggc cgg gtc agc ctg gtc aag gac agg gcc gcc cgc tac gcc gcc      192
Pro Gly Arg Val Ser Leu Val Lys Asp Arg Ala Ala Arg Tyr Ala Ala
         50                  55                  60 gac cac ggc ctc gac gaa tcg ttc ctg gtg aac ctc tac gac gtg atc      240
Asp His Gly Leu Asp Glu Ser Phe Leu Val Asn Leu Tyr Asp Val Ile
 65                  70                  75                  80 atc acg gag atg tgc cgc gtc gag gac ctg gtg atg agc cgg gag agc      288
Ile Thr Glu Met Cys Arg Val Glu Asp Leu Val Met Ser Arg Glu Ser
                 85                  90                  95 ctg acg gcc gag gac cgg cgg tga                                      312
Leu Thr Ala Glu Asp Arg Arg
            100
```

<210> SEQ ID NO 4
<211> LENGTH: 103
<212> TYPE: PRT
<213> ORGANISM: Streptomyces venezuelae

<400> SEQUENCE: 4

```
Met Thr Glu Gln Asn Glu Leu Gln Arg Leu Arg Ala Glu Leu Asp Ala
 1               5                  10                  15

Leu Asp Gly Thr Leu Leu Asp Thr Val Arg Arg Ile Asp Leu Gly
             20                  25                  30

Val Arg Ile Ala Arg Tyr Lys Ser Arg His Gly Val Pro Met Met Gln
         35                  40                  45

Pro Gly Arg Val Ser Leu Val Lys Asp Arg Ala Ala Arg Tyr Ala Ala
     50                  55                  60

Asp His Gly Leu Asp Glu Ser Phe Leu Val Asn Leu Tyr Asp Val Ile
 65                  70                  75                  80

Ile Thr Glu Met Cys Arg Val Glu Asp Leu Val Met Ser Arg Glu Ser
                 85                  90                  95

Leu Thr Ala Glu Asp Arg Arg
            100
```

<210> SEQ ID NO 5
<211> LENGTH: 969
<212> TYPE: DNA
<213> ORGANISM: Streptomyces venezuelae
<220> FEATURE:
<221> NAME/KEY: CDS
<222> LOCATION: (1)..(966)

<400> SEQUENCE: 5

```
atg agc ggc ttc ccc cgc agc gtc gtc gtc ggc ggc agc ggg gcg gtg       48
Met Ser Gly Phe Pro Arg Ser Val Val Val Gly Gly Ser Gly Ala Val
 1               5                  10                  15 ggc ggc atg ttc gcc ggg ctg ctg cgg gag gcg ggc agc cgc acg ctc       96
Gly Gly Met Phe Ala Gly Leu Leu Arg Glu Ala Gly Ser Arg Thr Leu
             20                  25                  30 gtc gtc gac ctc gta ccg ccg ccg gga cgg ccg gac gcc tgc ctg gtg      144
Val Val Asp Leu Val Pro Pro Pro Gly Arg Pro Asp Ala Cys Leu Val
         35                  40                  45 ggc gac gtc acc gcg ccg ggg ccc gaa ctc gcg gcc gcc ctc cgg gac      192
Gly Asp Val Thr Ala Pro Gly Pro Glu Leu Ala Ala Ala Leu Arg Asp
     50                  55                  60 gcg gac ctc gtc ctg ctc gcc gta cac gag gac gtg gcc ctc aag gcc      240
Ala Asp Leu Val Leu Leu Ala Val His Glu Asp Val Ala Leu Lys Ala
 65                  70                  75                  80 gtg gcg ccc gtg acc cgg ctc atg cgg ccg ggc gcg ctg ctc gcc gac      288
Val Ala Pro Val Thr Arg Leu Met Arg Pro Gly Ala Leu Leu Ala Asp
```

-continued

```
                    85                   90                   95
acc ctg tcc gtc cgg acg ggc atg gcc gcg gag ctc gcg gcc cac gcc      336
Thr Leu Ser Val Arg Thr Gly Met Ala Ala Glu Leu Ala Ala His Ala
                   100                 105                 110 ccc ggc gtc cag cac gtg ggc ctc aac ccg atg ttc gcc ccc gcc gcc      384
Pro Gly Val Gln His Val Gly Leu Asn Pro Met Phe Ala Pro Ala Ala
               115                 120                 125 ggc atg acc ggc cga ccc gtg gcc gcc gtg gtc acc agg gac ggg ccg      432
Gly Met Thr Gly Arg Pro Val Ala Ala Val Val Thr Arg Asp Gly Pro
           130                 135                 140 ggc gtc acg gcc ctg ctg cgg ctc gtc gag ggc ggc ggc ggc agg ccc      480
Gly Val Thr Ala Leu Leu Arg Leu Val Glu Gly Gly Gly Gly Arg Pro
145                 150                 155                 160 gta cgg ctc acg gcg gag gag cac gac cgg acg acg gcg gcc acc cag      528
Val Arg Leu Thr Ala Glu Glu His Asp Arg Thr Thr Ala Ala Thr Gln
               165                 170                 175 gcc ctg acg cac gcc gtg ctc ctc tcc ttc ggg ctc gcc ctc gcc cgc      576
Ala Leu Thr His Ala Val Leu Leu Ser Phe Gly Leu Ala Leu Ala Arg
           180                 185                 190 ctc ggc gtc gac gtc cgg gcc ctg gcg gcg acg gca ccg ccg ccc cac      624
Leu Gly Val Asp Val Arg Ala Leu Ala Ala Thr Ala Pro Pro Pro His
       195                 200                 205 cag gtg ctg ctc gcc ctc ctg gcc cgt gtg ctc ggc ggc agc ccc gag      672
Gln Val Leu Leu Ala Leu Leu Ala Arg Val Leu Gly Gly Ser Pro Glu
   210                 215                 220 gtg tac ggg gac atc cag cgg tcc aac ccc cgg gcg gcg tcc gcg cgc      720
Val Tyr Gly Asp Ile Gln Arg Ser Asn Pro Arg Ala Ala Ser Ala Arg
225                 230                 235                 240 cgg gcg ctc gcc gag gcc ctg cgc tcc ttc gcc gcg ctg gtc ggc gac      768
Arg Ala Leu Ala Glu Ala Leu Arg Ser Phe Ala Ala Leu Val Gly Asp
                   245                 250                 255 gac ccg gac cgt gcc gac gcc ccc ggg cgc gcc gac gcc ccc ggc cat      816
Asp Pro Asp Arg Ala Asp Ala Pro Gly Arg Ala Asp Ala Pro Gly His
               260                 265                 270 ccc ggg gga tgc gac ggc gcc ggg aac ctc gac ggc gtc ttc ggg gaa      864
Pro Gly Gly Cys Asp Gly Ala Gly Asn Leu Asp Gly Val Phe Gly Glu
           275                 280                 285 ctc cgc cgg ctc atg gga ccg gag ctc gcg gcg ggc cag gac cac tgc      912
Leu Arg Arg Leu Met Gly Pro Glu Leu Ala Ala Gly Gln Asp His Cys
       290                 295                 300 cag gag ctg ttc cgc acc ctc cac cgc acc gac gac gaa ggc gag aag      960
Gln Glu Leu Phe Arg Thr Leu His Arg Thr Asp Asp Glu Gly Glu Lys
305                 310                 315                 320 gac cga tga                                                          969
Asp Arg
```

<210> SEQ ID NO 6
<211> LENGTH: 322
<212> TYPE: PRT
<213> ORGANISM: Streptomyces venezuelae

<400> SEQUENCE: 6

```
Met Ser Gly Phe Pro Arg Ser Val Val Gly Gly Ser Gly Ala Val
 1               5                  10                  15

Gly Gly Met Phe Ala Gly Leu Leu Arg Glu Ala Gly Ser Arg Thr Leu
            20                  25                  30

Val Val Asp Leu Val Pro Pro Gly Arg Pro Asp Ala Cys Leu Val
            35                  40                  45

Gly Asp Val Thr Ala Pro Gly Pro Glu Leu Ala Ala Ala Leu Arg Asp
```

```
                50                  55                  60
Ala Asp Leu Val Leu Ala Val His Glu Asp Val Ala Leu Lys Ala
 65                  70                  75                  80

Val Ala Pro Val Thr Arg Leu Met Arg Pro Gly Ala Leu Leu Asp
                 85                  90                  95

Thr Leu Ser Val Arg Thr Gly Met Ala Ala Glu Leu Ala Ala His Ala
                100                 105                 110

Pro Gly Val Gln His Val Gly Leu Asn Pro Met Phe Ala Pro Ala Ala
                115                 120                 125

Gly Met Thr Gly Arg Pro Val Ala Ala Val Thr Arg Asp Gly Pro
130                 135                 140

Gly Val Thr Ala Leu Leu Arg Leu Val Glu Gly Gly Gly Arg Pro
145                 150                 155                 160

Val Arg Leu Thr Ala Glu Glu His Asp Arg Thr Thr Ala Ala Thr Gln
                165                 170                 175

Ala Leu Thr His Ala Val Leu Leu Ser Phe Gly Leu Ala Leu Ala Arg
                180                 185                 190

Leu Gly Val Asp Val Arg Ala Leu Ala Ala Thr Ala Pro Pro His
                195                 200                 205

Gln Val Leu Leu Ala Leu Leu Ala Arg Val Leu Gly Gly Ser Pro Glu
                210                 215                 220

Val Tyr Gly Asp Ile Gln Arg Ser Asn Pro Arg Ala Ala Ser Ala Arg
225                 230                 235                 240

Arg Ala Leu Ala Glu Ala Leu Arg Ser Phe Ala Ala Leu Val Gly Asp
                245                 250                 255

Asp Pro Asp Arg Ala Asp Ala Pro Gly Arg Ala Asp Ala Pro Gly His
                260                 265                 270

Pro Gly Gly Cys Asp Gly Ala Gly Asn Leu Asp Gly Val Phe Gly Glu
                275                 280                 285

Leu Arg Arg Leu Met Gly Pro Glu Leu Ala Ala Gly Gln Asp His Cys
                290                 295                 300

Gln Glu Leu Phe Arg Thr Leu His Arg Thr Asp Asp Glu Gly Glu Lys
305                 310                 315                 320

Asp Arg

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence:PCR primer
      for the pabAB gene

<400> SEQUENCE: 7 gggggggatcc tatgcgcacg cttctgatcg ac                                32

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence:PCR primer
      for the pabAB gene

<400> SEQUENCE: 8 gggggggatcc tcatcgggcg cccgccactg cg                                32
```

```
<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence:PCR primer
      for the papA gene

<400> SEQUENCE: 9
ggtgatcata tgcgcacgct tctgatcgac                                       30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:PCR primer
      for the papA gene

<400> SEQUENCE: 10
ggtgatcatc atcgggcgcc cgccacggcg                                       30

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence:PCR primer
      for the papB gene

<400> SEQUENCE: 11
gcggatccat atgaccgagc agaacgagct g                                     31

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence:PCR primer
      for the papB gene

<400> SEQUENCE: 12
gcggatcctc accgccggtc ctcggc                                           26

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence:PCR primer
      for the papC gene

<400> SEQUENCE: 13
gcggatccat atgagcggct tcccccgca                                        29

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence:PCR primer
      for the papC gene

<400> SEQUENCE: 14
gcggatcctc atcggtcctt ctcgccttc                                        29

<210> SEQ ID NO 15
```

```
<211> LENGTH: 20
<212> TYPE: DNA
<213> ORGANISM: Artificial Sequence
<220> FEATURE:
<223> OTHER INFORMATION: Description of Artificial Sequence:PCR primer
      for the Abp1 gene

<400> SEQUENCE: 15
ctcaaaccag gaactctttc                                                  20

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence:PCR primer
      for the Abp1 gene

<400> SEQUENCE: 16
gacatgtgga aaccacattt tg                                               22

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence:PCR primer
      for the Abp1 gene

<400> SEQUENCE: 17
ggggaattcg tgggtggtga tatcatggc                                        29

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence:PCR primer
      for the Abp1 gene

<400> SEQUENCE: 18
gggggatcct tgatgggttt tggg                                             24

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence:PCR primer
      for the Abp1 gene

<400> SEQUENCE: 19
gggggatcct aaactcccat ctatagc                                          27

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence:PCR primer
      for the Abp1 gene

<400> SEQUENCE: 20
gggtctagac gactcattgc agtgagtgg                                        29

<210> SEQ ID NO 21
<211> LENGTH: 49
```

```
<212> TYPE: DNA
<213> ORGANISM: Artificial Sequence
<220> FEATURE:
<223> OTHER INFORMATION: Description of Artificial Sequence:primer for
      site-directed mutagenesis

<400> SEQUENCE: 21
gatcagaagc gtgcgcattg ttaggttgat tgatgggttt tgggaattg                49

<210> SEQ ID NO 22
<211> LENGTH: 49
<212> TYPE: DNA
<213> ORGANISM: Artificial Sequence
<220> FEATURE:
<223> OTHER INFORMATION: Description of Artificial Sequence:primer for
      site-directed mutagenesis

<400> SEQUENCE: 22
ctcgttctgc tcggtcattg ttaggttgat tgatgggttt tgggaattg                49

<210> SEQ ID NO 23
<211> LENGTH: 48
<212> TYPE: DNA
<213> ORGANISM: Artificial Sequence
<220> FEATURE:
<223> OTHER INFORMATION: Description of Artificial Sequence:primer for
      site-directed mutagenesis

<400> SEQUENCE: 23
cgggggaagc cgctcattgt taggttgatt gatgggtttt gggaattg                 48

<210> SEQ ID NO 24
<211> LENGTH: 17
<212> TYPE: DNA
<213> ORGANISM: Artificial Sequence
<220> FEATURE:
<221> NAME/KEY: base
<222> LOCATION: (5)
<223> OTHER INFORMATION: w = a or t
<220> FEATURE:
<221> NAME/KEY: base
<222> LOCATION: (6)
<223> OTHER INFORMATION: y = t or c
<220> FEATURE:
<221> NAME/KEY: base
<222> LOCATION: (9)
<223> OTHER INFORMATION: n = a g c or t
<220> FEATURE:
<221> NAME/KEY: base
<222> LOCATION: (12)
<223> OTHER INFORMATION: r = g or a
<220> FEATURE:
<221> NAME/KEY: base
<222> LOCATION: (15)
<223> OTHER INFORMATION: y = t or c
<220> FEATURE:
<223> OTHER INFORMATION: Description of Artificial Sequence:PCR primer
      for the chorismate mutase gene

<400> SEQUENCE: 24
caytwyggna arttygt                                                   17

<210> SEQ ID NO 25
<211> LENGTH: 17
<212> TYPE: DNA
<213> ORGANISM: Artificial Sequence
<220> FEATURE:
<221> NAME/KEY: base
<222> LOCATION: (3)
<223> OTHER INFORMATION: y = t or c
<220> FEATURE:
```

```
<221> NAME/KEY: base
<222> LOCATION: (6)
<223> OTHER INFORMATION: n = a g c or t
<220> FEATURE:
<221> NAME/KEY: base
<222> LOCATION: (9)
<223> OTHER INFORMATION: y = t or c
<220> FEATURE:
<221> NAME/KEY: base
<222> LOCATION: (11)
<223> OTHER INFORMATION: s = g or c
<220> FEATURE:
<221> NAME/KEY: base
<222> LOCATION: (12)
<223> OTHER INFORMATION: n = a g c or t
<220> FEATURE:
<221> NAME/KEY: base
<222> LOCATION: (15)
<223> OTHER INFORMATION: y = t or c
<220> FEATURE:
<223> OTHER INFORMATION: Description of Artificial Sequence:PCR primer
      for the chorismate mutase gene

<400> SEQUENCE: 25
taytcnacyt snacytc                                                    17

<210> SEQ ID NO 26
<211> LENGTH: 869
<212> TYPE: DNA
<213> ORGANISM: Mycelia sterilia
<220> FEATURE:
<221> NAME/KEY: intron
<222> LOCATION: (72)..(148)

<400> SEQUENCE: 26
atggatacta taatcgatct gaaagatgcc tccaaggcgc ttgacttggg caacatccgc      60
ttccaactca tgtaagtggc tagcctcacc gctaccctgt atgccactgg gtgtgttcat     120
gtatgcttac tatccctctt catactagac gcctcgaaga cacaatcacc tttcacttga     180
tcgagcgggt gcaatttccc ttgaacaagt cgatctacca gccgggtgcc atcgcgctgg     240
gctcggatgc gaatttgagc ttcatggact ggtacctgca ggaacaagag aagctgcagt     300
cgttgatccg acgttacgaa gcgccggacg agtacccatt cttcccggat gcgctacaga     360
agccgatcct gaagccgctc gactacccca agatcctgca ccctaacgac gttaacgtga     420
acgagaagat caagcgcttc tacatcgagc gtttcctgcc cgccgtgtgt ccggacttcg     480
gccgcggcga cggcggcgag ttggatgaga actacggatc ctcggccacc tgcgacatcg     540
cctgtctcca ggccctctcc cgtcgtatcc atttcggcaa gttcgtcgcc gagtccaagt     600
tccagtccga cccggagctc tacacgagac tgatcaaggc cggcgatcgc gacggcatcg     660
gcgagtccat caccaacgcg gccgtcgaga agcaggtgct cgcccggctt cgtctcaagg     720
cgcagacata tggcacggac ccttcgtcca ctaataccac cggcgcggga aagatcaatg     780
ccgatgcggt tgagtccatg tacagggatt tcgtgatccc catcaccaaa gaggtcgaag     840
tagagtacct catgcaacga ctagagtag                                      869

<210> SEQ ID NO 27
<211> LENGTH: 263
<212> TYPE: PRT
<213> ORGANISM: Mycelia sterilia

<400> SEQUENCE: 27

Met Asp Thr Ile Ile Asp Leu Lys Asp Ala Ser Lys Ala Leu Asp Leu
  1               5                  10                  15
```

```
Gly Asn Ile Arg Phe Gln Leu Ile Arg Leu Glu Asp Thr Ile Thr Phe
             20                  25                  30

His Leu Ile Glu Arg Val Gln Phe Pro Leu Asn Lys Ser Ile Tyr Gln
         35                  40                  45

Pro Gly Ala Ile Ala Leu Gly Ser Asp Ala Asn Leu Ser Phe Met Asp
     50                  55                  60

Trp Tyr Leu Gln Glu Gln Glu Lys Leu Gln Ser Leu Ile Arg Arg Tyr
 65                  70                  75                  80

Glu Ala Pro Asp Glu Tyr Pro Phe Phe Pro Asp Ala Leu Gln Lys Pro
                 85                  90                  95

Ile Leu Lys Pro Leu Asp Tyr Pro Lys Ile Leu His Pro Asn Asp Val
             100                 105                 110

Asn Val Asn Glu Lys Ile Lys Arg Phe Tyr Ile Glu Arg Phe Leu Pro
         115                 120                 125

Ala Val Cys Pro Asp Phe Gly Arg Gly Asp Gly Glu Leu Asp Glu
     130                 135                 140

Asn Tyr Gly Ser Ser Ala Thr Cys Asp Ile Ala Cys Leu Gln Ala Leu
145                 150                 155                 160

Ser Arg Arg Ile His Phe Gly Lys Phe Val Ala Glu Ser Lys Phe Gln
                 165                 170                 175

Ser Asp Pro Glu Leu Tyr Thr Arg Leu Ile Lys Ala Gly Asp Arg Asp
             180                 185                 190

Gly Ile Gly Glu Ser Ile Thr Asn Ala Ala Val Glu Lys Gln Val Leu
         195                 200                 205

Ala Arg Leu Arg Leu Lys Ala Gln Thr Tyr Gly Thr Asp Pro Ser Ser
     210                 215                 220

Thr Asn Thr Thr Gly Ala Gly Lys Ile Asn Ala Asp Ala Val Glu Ser
225                 230                 235                 240

Met Tyr Arg Asp Phe Val Ile Pro Ile Thr Lys Glu Val Glu Val Glu
                 245                 250                 255

Tyr Leu Met Gln Arg Leu Glu
             260

<210> SEQ ID NO 28
<211> LENGTH: 23
<212> TYPE: PRT
<213> ORGANISM: Myceria sterilia
<220> FEATURE:
<221> NAME/KEY: Residue
<222> LOCATION:
<223> OTHER INFORMATION: Xaa = Any amino acid

<400> SEQUENCE: 28

Gly His Thr Ser Ala Gly Asp Ala Gly Ser Lys Pro Val Val Xaa Phe
 1               5                  10                  15

Leu Gly Pro Ile Ser Ser Tyr
             20

<210> SEQ ID NO 29
<211> LENGTH: 12
<212> TYPE: PRT
<213> ORGANISM: Myceria sterilia

<400> SEQUENCE: 29

Gly Val Glu Thr Val Asp Val Ser Ser Thr Ser Arg
 1               5                  10

<210> SEQ ID NO 30
```

```
<211> LENGTH: 8
<212> TYPE: PRT
<213> ORGANISM: Myceria sterilia

<400> SEQUENCE: 30

Thr Leu Asp His Phe Ala Asp Arg
 1               5

<210> SEQ ID NO 31
<211> LENGTH: 5
<212> TYPE: PRT
<213> ORGANISM: Myceria sterilia

<400> SEQUENCE: 31

Phe Phe Val Leu Arg
 1               5

<210> SEQ ID NO 32
<211> LENGTH: 16
<212> TYPE: PRT
<213> ORGANISM: Myceria sterilia

<400> SEQUENCE: 32

Ala Phe Pro Leu Glu Gln Phe Asp Leu Met Pro Val Thr Thr Ile Lys
 1               5                  10                  15

<210> SEQ ID NO 33
<211> LENGTH: 17
<212> TYPE: DNA
<213> ORGANISM: Artificial Sequence
<220> FEATURE:
<221> NAME/KEY: base
<222> LOCATION: (3)
<223> OTHER INFORMATION: y = t or c
<220> FEATURE:
<221> NAME/KEY: base
<222> LOCATION: (6)
<223> OTHER INFORMATION: n = a g c or t
<220> FEATURE:
<221> NAME/KEY: base
<222> LOCATION: (9)
<223> OTHER INFORMATION: n = a g c or t
<220> FEATURE:
<221> NAME/KEY: base
<222> LOCATION: (12)
<223> OTHER INFORMATION: y = t or c
<220> FEATURE:
<221> NAME/KEY: base
<222> LOCATION: (15)
<223> OTHER INFORMATION: n = a g c or t
<220> FEATURE:
<223> OTHER INFORMATION: Description of Artificial Sequence:A PCR primer
      for PDT gene screening

<400> SEQUENCE: 33
tcygcnggng aygcngg                                              17

<210> SEQ ID NO 34
<211> LENGTH: 17
<212> TYPE: DNA
<213> ORGANISM: Artificial Sequence
<220> FEATURE:
<221> NAME/KEY: base
<222> LOCATION: (3)
<223> OTHER INFORMATION: r = g or a
<220> FEATURE:
<221> NAME/KEY: base
<222> LOCATION: (6)
<223> OTHER INFORMATION: n = a g c or t
<220> FEATURE:
<221> NAME/KEY: base
```

```
<222> LOCATION: (9)
<223> OTHER INFORMATION: n = a g c or t
<220> FEATURE:
<221> NAME/KEY: base
<222> LOCATION: (12)
<223> OTHER INFORMATION: y = t or c
<220> FEATURE:
<221> NAME/KEY: base
<222> LOCATION: (15)
<223> OTHER INFORMATION: n = a g c or t
<220> FEATURE:
<223> OTHER INFORMATION: Description of Artificial Sequence:A PCR primer
      for PDT gene screening

<400> SEQUENCE: 34
tcrgcnggng aygcngg                                                    17

<210> SEQ ID NO 35
<211> LENGTH: 17
<212> TYPE: DNA
<213> ORGANISM: Artificial Sequence
<220> FEATURE:
<221> NAME/KEY: base
<222> LOCATION: (3)
<223> OTHER INFORMATION: y = t or c
<220> FEATURE:
<221> NAME/KEY: base
<222> LOCATION: (6)
<223> OTHER INFORMATION: n = a g c or t
<220> FEATURE:
<221> NAME/KEY: base
<222> LOCATION: (9)
<223> OTHER INFORMATION: n = a g c or t
<220> FEATURE:
<221> NAME/KEY: base
<222> LOCATION: (12)
<223> OTHER INFORMATION: y = t or c
<220> FEATURE:
<221> NAME/KEY: base
<222> LOCATION: (15)
<223> OTHER INFORMATION: n = a g c or t
<220> FEATURE:
<223> OTHER INFORMATION: Description of Artificial Sequence:A PCR primer
      for PDT gene screening

<400> SEQUENCE: 35
agygcnggng aygcngg                                                    17

<210> SEQ ID NO 36
<211> LENGTH: 20
<212> TYPE: DNA
<213> ORGANISM: Artificial Sequence
<220> FEATURE:
<221> NAME/KEY: base
<222> LOCATION: (6)
<223> OTHER INFORMATION: n = a g c or t
<220> FEATURE:
<221> NAME/KEY: base
<222> LOCATION: (8)
<223> OTHER INFORMATION: r = g or a
<220> FEATURE:
<221> NAME/KEY: base
<222> LOCATION: (9)
<223> OTHER INFORMATION: r = g or a
<220> FEATURE:
<221> NAME/KEY: base
<222> LOCATION: (12)
<223> OTHER INFORMATION: r = g or a
<220> FEATURE:
<221> NAME/KEY: base
<222> LOCATION: (15)
<223> OTHER INFORMATION: y = t or c
<220> FEATURE:
<221> NAME/KEY: base
<222> LOCATION: (18)
```

-continued

<223> OTHER INFORMATION: y = t or c
<220> FEATURE:
<223> OTHER INFORMATION: Description of Artificial Sequence:A PCR primer
for PDT gene screening

<400> SEQUENCE: 36
ggcatnarrt craaytgytc 20

<210> SEQ ID NO 37
<211> LENGTH: 1366
<212> TYPE: DNA
<213> ORGANISM: Myceria sterilia
<220> FEATURE:
<221> NAME/KEY: intron
<222> LOCATION: (91)..(192)
<220> FEATURE:
<221> NAME/KEY: intron
<222> LOCATION: (254)..(380)

<400> SEQUENCE: 37
atggaggcga gcggtcatac cagcgctgga gatgcaggct ccaaacctgt cgtctgtttc 60
ttggggccga tatcgtccta tacacatcag gtatgcacaa tgcactcact tcaagatttc 120
gtttttaaat aaacccgtgt ctcattatgc ctatcatcaa ctaataattg agttctcatg 180
agttatgtat aggcgacgct gaaagctttt ccactagagc aatttgattt gatgcccgtg 240
accacaatca aaggtgtgta acgaatctca agactgactg ttcctttata atgctattgg 300
ttcgatatca tatcgatatt attattatta tatatatgtc acgttatgtc aggagtattc 360
aagctaatac gtgaagcaag atatctttga cacaacacaa tccggcgccg cgacatacgg 420
cgtggtccca ttcgagaact ccaccaacgg ctccgtggtc ttcaccctcg accacttcgc 480
cgaccggtcc gggctctacc cggacctcaa cgtctgcagg gagatctacc tagacgtgca 540
ccactgcctg ctcggccacg catcatcatc atcctcctcc cccactaact caaactcgga 600
ccccatatcc cgcctccgcc gcgtatacag ccacccgcaa gccttcgggc aatgcacgct 660
attcctaggc tcgcggctcc cccgcggcgt cgaaaccgtc gacgtgagca gcacgagccg 720
cgcagcggaa ctcgcgtccg cggatacatc gggcgagagc gccgccatta gctctgctgc 780
tgctgccgag ctgctcggcc tcgatgtgtt ggtgagtaat atcgaggacc gcgaggataa 840
tactacgagg ttctttgtgc ttaggagggg tgtgctgggt gattgcgatg ggtctgcgga 900
aaaaggggaa gaggaagagg gggaacggga tgggggggaaa ggagaaggag atgacgacga 960
cgcggccctc ctatcgagca cgaaatccct cctctccttc accgtgccgc atcgtagccc 1020
gggggccctc gccgacgtac tctcgtgctt tcgccgtggc gggctgaatc tcacgagcat 1080
taatagccgg cctagtctca ccactaccac ctccacttct accacttcca cttctactac 1140
caccacttct actactggta ctggtactgg tactggtact gggtcaggct cgggctcggg 1200
ctccgtttcc gcggccttcg aatacatctt cttcgtcgag ttcgagggcc atcggttccg 1260
cgaccccaag ggcagggtcg cccgggtcct cgccgacgtc gctgctggcg cggcctcgtc 1320
gaggtggctt gggagctggg agaatatgcg ggcgagcgtg gggtga 1366

<210> SEQ ID NO 38
<211> LENGTH: 378
<212> TYPE: PRT
<213> ORGANISM: Myceria sterilia

<400> SEQUENCE: 38

Met Glu Ala Ser Gly His Thr Ser Ala Gly Asp Ala Gly Ser Lys Pro
1 5 10 15

Val Val Cys Phe Leu Gly Pro Ile Ser Ser Tyr Thr His Gln Ala Thr
            20                  25                  30

Leu Lys Ala Phe Pro Leu Glu Gln Phe Asp Leu Met Pro Val Thr Thr
        35                  40                  45

Ile Lys Asp Ile Phe Asp Thr Thr Gln Ser Gly Ala Ala Thr Tyr Gly
    50                  55                  60

Val Val Pro Phe Glu Asn Ser Thr Asn Gly Ser Val Val Phe Thr Leu
65                  70                  75                  80

Asp His Phe Ala Asp Arg Ser Gly Leu Tyr Pro Asp Leu Asn Val Cys
                85                  90                  95

Arg Glu Ile Tyr Leu Asp Val His His Cys Leu Leu Gly His Ala Ser
            100                 105                 110

Ser Ser Ser Ser Ser Pro Thr Asn Ser Asn Ser Asp Pro Ile Ser Arg
        115                 120                 125

Leu Arg Arg Val Tyr Ser His Pro Gln Ala Phe Gly Gln Cys Thr Leu
    130                 135                 140

Phe Leu Gly Ser Arg Leu Pro Arg Gly Val Glu Thr Val Asp Val Ser
145                 150                 155                 160

Ser Thr Ser Arg Ala Ala Glu Leu Ala Ser Ala Asp Thr Ser Gly Glu
                165                 170                 175

Ser Ala Ala Ile Ser Ser Ala Ala Ala Glu Leu Leu Gly Leu Asp
            180                 185                 190

Val Leu Val Ser Asn Ile Glu Asp Arg Glu Asp Asn Thr Thr Arg Phe
        195                 200                 205

Phe Val Leu Arg Arg Gly Val Leu Gly Asp Cys Asp Gly Ser Ala Glu
210                 215                 220

Lys Gly Glu Glu Glu Gly Glu Arg Asp Gly Lys Gly Glu Gly
225                 230                 235                 240

Asp Asp Asp Asp Ala Ala Leu Leu Ser Ser Thr Lys Ser Leu Leu Ser
                245                 250                 255

Phe Thr Val Pro His Arg Ser Pro Gly Ala Leu Ala Asp Val Leu Ser
            260                 265                 270

Cys Phe Arg Arg Gly Gly Leu Asn Leu Thr Ser Ile Asn Ser Arg Pro
        275                 280                 285

Ser Leu Thr Thr Thr Thr Ser Thr Ser Thr Thr Ser Thr Ser Thr Thr
    290                 295                 300

Thr Thr Ser Thr Thr Gly Thr Gly Thr Gly Thr Gly Thr Gly Ser Gly
305                 310                 315                 320

Ser Gly Ser Gly Ser Val Ser Ala Ala Phe Glu Tyr Ile Phe Phe Val
                325                 330                 335

Glu Phe Glu Gly His Arg Phe Arg Asp Pro Lys Gly Arg Val Ala Arg
            340                 345                 350

Val Leu Ala Asp Val Ala Ala Gly Ala Ala Ser Ser Arg Trp Leu Gly
        355                 360                 365

Ser Trp Glu Asn Met Arg Ala Ser Val Gly
    370                 375

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence:A PCR primer
      for BSD gene

```
<400> SEQUENCE: 39
gcatcgatgc ctttgtctca agaag                                              25

<210> SEQ ID NO 40
<211> LENGTH: 26
<212> TYPE: DNA
<213> ORGANISM: Artificial Sequence
<220> FEATURE:
<223> OTHER INFORMATION: Description of Artificial Sequence:A PCR primer
      for BSD gene

<400> SEQUENCE: 40
gcagatctta gccctcccac acataa                                             26
```

TRANSFORMANTS PRODUCING SUBSTANCE PF1022 DERIVATIVES, METHODS FOR PRODUCING THE SAME, AND NOVEL BIOSYNTHESIS GENES

This application is U.S. national stage of International Application No. PCT/JP02/02782 filed Mar. 22, 2002.

BACKGROUND OF THE INVENTION

1. Field of the Invention

The present invention relates to transformants producing a substance PF1022 derivative, and to methods for producing the PF1022 derivative using the transformants. Furthermore, the present invention relates to novel genes involved in a biosynthetic pathway from chorismic acid to phenylpyruvic acid.

2. Background Art

Substance PF1022 has anthelmintic activity and its utilization for drugs for humans and animals is expected. Substance PF1022 is a cyclic depsipeptide represented by formula (I);

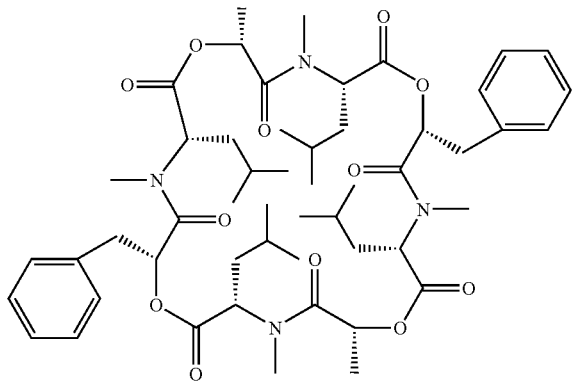

and is known to be manufactured by a fermentation method (Japanese Patent Application Laid-open Publication No. 35796/1991).

Substance PF1022 is a cyclic depsipeptide composed of L-N-methylleucine[$(CH_3)_2CHCH_2CH(NHCH_3)COOH$] (H-L-MeLeu-OH), D-lactic acid [$CH_3CH(OH)COOH$] (H-D-Lac-OH), and D-phenyllactic acid [$C_6H_5CH_2CH(OH)COOH$] (H-D-PhLac-OH) bonded by ester bonds and amide bonds.

Substance PF1022 can also be represented by formula (II): Cyclo(L-MeLeu-D-Lac-L-MeLeu-D-PhLac-L-MeLeu-D-Lac-L-MeLeu-D-PhLac).

As for substance PF1022 derivatives, seven kinds of derivatives, i.e., PF1022B, PF1022C, PF1022D, PF1022E, PF1022F, PF1022G, and PF1022H, are reported to be manufactured by a fermentation method (Japanese Patent Application Laid-open Publication No. 170749/1993, Japanese Patent Application Laid-open Publication No. 184126/1994, WO98/05655). Further, various substance PF1022 derivatives having anthelmintic activity are manufactured by chemical synthesis (WO94/19334, WO97/11064, Japanese Patent No. 2874342). Among them, a substance PF1022 derivative, PF1022-220, represented by formula (III):

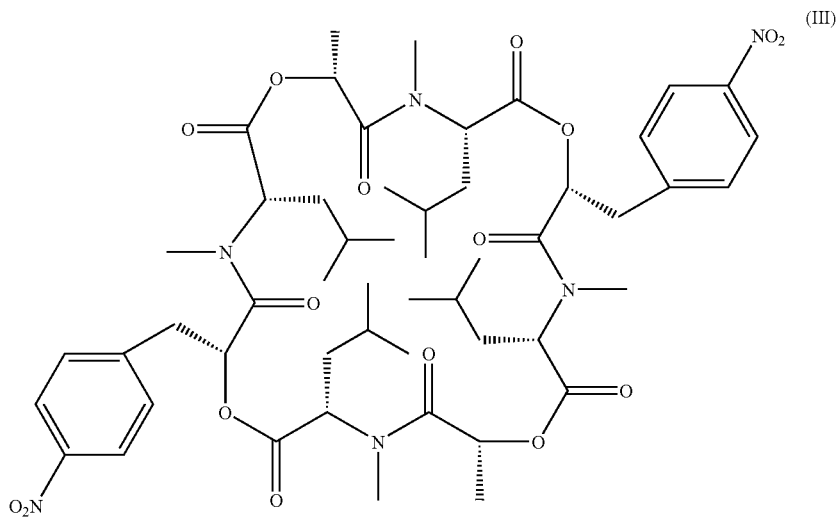

or formula (IV): Cyclo(L-MeLeu-D-Lac-L-MeLeu-D-p-NO$_2$PhLac-L-MeLeu-D-Lac-L-MeLeu-D-p-NO$_2$PhLac), wherein D-p-NO$_2$PhLac represents D-p-nitrophenyllactic acid, and a substance PF1022 derivative, PF1022-260, represented by formula (V):

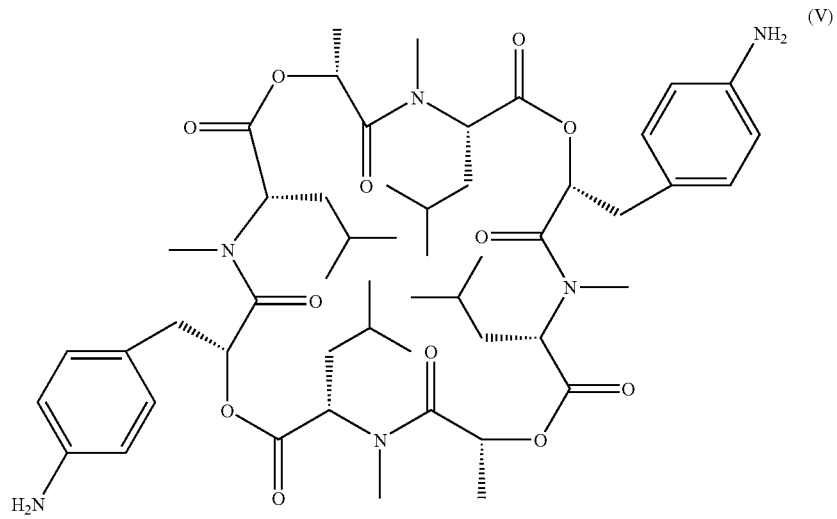

or formula (VI): Cyclo (L-MeLeu-D-Lac-L-MeLeu-D-p-NH$_2$PhLac-L-MeLeu-D-Lac-L-MeLeu-D-p-NH$_2$PhLac), wherein D-p-NH$_2$PhLac represents D-p-aminophenyllactic acid, not only have anthelmintic activity by themselves but also serve an extremely effective substance as a raw material for synthesizing substance PF1022 derivatives having high anthelmintic activity (Japanese Patent No. 2874342).

However, PF1022-220 and PF1022-260 could be manufactured only by chemical synthesis. In manufacturing a cyclic depsipeptide having a complicated cyclic core, such as substance PF1022, a production method using fermentation is advantageous in terms of time generally required, labor, cost, and the like and can be easily carried out, as compared to a chemical synthesis method. Accordingly, a process by direct fermentation has been in need also for substance PF1022 derivatives represented by PF1022-220 and PF1022-260.

The present inventors introduced a gene involved in a biosynthetic pathway from chorismic acid to p-aminophenylpyruvic acid into an organism producing secondary metabolites in which a benzene ring skeleton is unsubstituted at the para-position with a functional group containing a nitrogen atom, obtained a transformant, and further established a method of producing secondary metabolites in which a benzene ring skeleton is substituted at the para-position with a functional group containing a nitrogen atom, by using this transformant (WO01/23542).

SUMMARY OF THE INVENTION

By applying the method described in WO01/23542 to a host producing substance PF1022, the present inventors could confirm that the resulting transformants produced a substance PF1022 derivative, PF1022-268, represented by formula (VII):

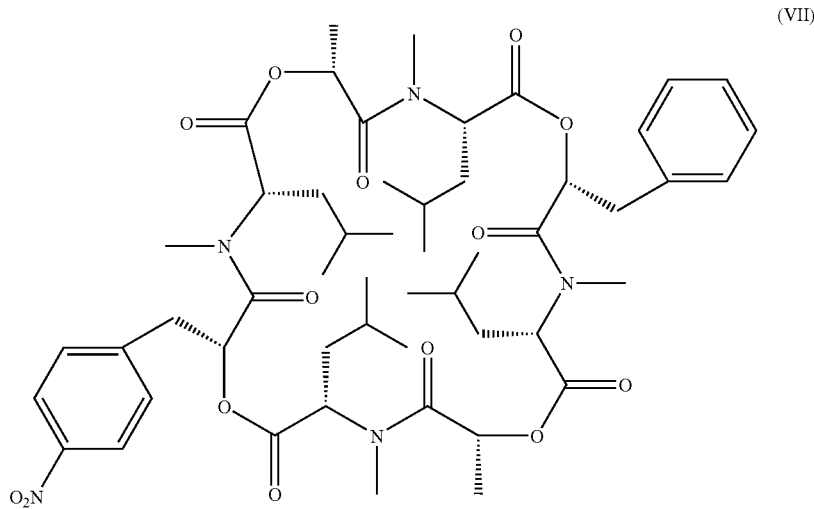

or formula (VIII): Cyclo(L-MeLeu-D-Lac-L-MeLeu-D-p-NO$_2$PhLac-L-MeLeu-D-Lac-L-MeLeu-D-PhLac)

and a substance PF1022 derivative, PF1022-269, represented by formula (IX):

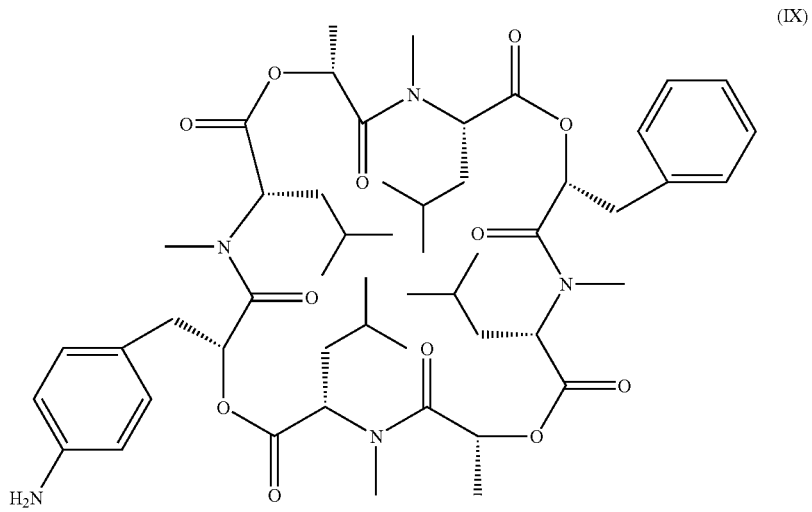
(IX)

or formula (X): Cyclo(L-MeLeu-D-Lac-L-MeLeu-D-p-NH₂PhLac-L-MeLeu-D-Lac-L-MeLeu-D-PhLac), but could not confirm the production of PF1022-220 and PF1022-260.

On the other hand, the present inventors have successfully obtained a transformant that newly produces substance PF1022 derivatives, PF1022-220 and PF1022-260, by inducing a phenylalanine auxotrophic mutant strain from an organism that produces substance PF1022, transforming this mutant strain with a DNA containing genes involved in a biosynthetic pathway from chorismic acid to p-aminophenylpyruvic acid. The present invention is based on these findings.

An objective of the present invention is to provide a method for producing substance PF1022 derivatives, in particular PF1022-220 and PF1022-260, by a direct fermentation method, and a transformant to be used for this method.

According to the present invention, there is provided a transformant producing substance PF1022 derivatives, in particular PF1022-220 (formula (III)) and PF1022-260 (formula (V)), which is obtainable by introducing genes involved in a biosynthetic pathway from chorismic acid to p-aminophenylpyruvic acid (biosynthesis gene) into a phenylalanine auxotrophic host induced from an organism that produces substance PF1022 represented by formula (I):

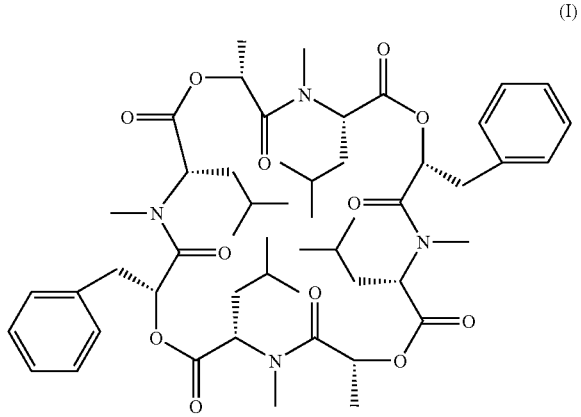
(I)

According to the present invention, there is also provided a process of producing substance PF1022 derivatives, comprising steps of culturing the abovementioned transformant and collecting the substance PF1022 derivatives.

Another objective of the present invention is to provide novel genes involved in the biosynthetic pathway from chorismic acid to pheylpyruvic acid.

Novel genes according to the present invention are
a polynucleotide encoding the amino acid sequence of SEQ ID NO: 27 or a modified sequence of SEQ ID NO: 27 having chorismate mutase activity; and
a polynucleotide encoding the amino acid sequence of SEQ ID NO: 38 or a modified sequence of SEQ ID NO: 38 having prephenate dehydratase activity.

BRIEF DESCRIPTION OF THE DRAWINGS

FIG. 4 shows the construction of plasmid pTrc-papB.
FIG. 6 shows the construction of plasmid pET-papC1.
FIG. 8 shows the construction of plasmids pPF260-A3 and pPF260-A4.
FIG. 13 shows the restriction map of the XbaI DNA fragment and the location of a chorismate mutase gene.

DETAILED DESCRIPTION OF THE INVENTION

Deposition of Microorganisms

Figure 1:
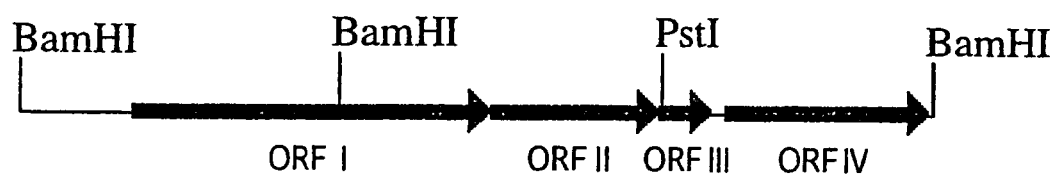
FIG. 1 shows the restriction map of a DNA fragment isolated from *Streptomyces venezuelae* and the position of open reading frames (ORF) thereon.

The PF1022 strain was deposited with the International Patent Organism Depositary, National Institute of Advanced Industrial Science and Technology (Tsukuba Central 6, 1-1-1 Higashi, Tsukuba, Ibaraki, Japan), dated Jan. 24, 1989. The accession number is FERM BP-2671.

*Escherichia coli* (JM109) transformed with plasmid pUC118-papA was deposited with the International Patent Organism Depositary, National Institute of Advanced Industrial Science and Technology (Tsukuba Central 6, 1-1-1 Higashi, Tsukuba, Ibaraki, Japan), dated Sep. 17, 1999. The accession number is FERM BP-7256.

*Escherichia coli* (JM109) transformed with plasmid pTrc-papB was deposited with the International Patent Organism Depositary, National Institute of Advanced Industrial Science and Technology (Tsukuba Central 6, 1-1-1 Higashi, Tsukuba, Ibaraki, Japan), dated Sep. 17, 1999. The accession number is FERM BP-7257.

*Escherichia coli* (JM109) transformed with plasmid pET-papC was deposited with the International Patent Organism Depositary, National Institute of Advanced Industrial Science and Technology (Tsukuba Central 6, 1-1-1 Higashi, Tsukuba, Ibaraki, Japan), dated Sep. 17, 1999. The accession number is FERM BP-7258.

*Escherichia coli* (JM109) transformed with plasmid pMKD01 was deposited with the International Patent Organism Depositary, National Institute of Advanced Industrial Science and Technology (Tsukuba Central 6, 1-1-1 Higashi, Tsukuba, Ibaraki, Japan), dated Jul. 12, 1996. The accession number is FERM BP-5974.

Phenylalanine Auxotrophic Host

The phenylalanine auxotrophic host used in the present invention means a phenylalanine auxotrophic mutant strain which is derived from an organism originally producing substance PF1022 (referred to as "substance PF1022-producing microorganism") by treating the organism for mutation as described later.

An example of preferable phenylalanine auxotrophic host is a mutant strain of a substance PF1022-producing microorganism which became to require auxotrophicity to phenylalanine by almost completely lacking enzyme activity involved in the biosynthetic pathway from chorismic acid to aminophenylpyruvic acid, more specifically chorismate mutase and/or prephenate dehydratase activity, or by significantly reducing these activity in the parent strain.

The phenylalanine auxotrophic mutant strain can be obtained by treating a substance PF1022-producing microorganism with UV light or with a mutagen such as N-methyl-N'-nitro-N-nitrosoguanidine (NTG) or nitrous acid and selecting a mutant strain which cannot grow when cultured in a minimum medium but recovers the growth by adding phenylalanine.

The mutant strain can also be obtained by utilizing recombinant DNA technology. Namely, a gene encoding chorismate mutase or prephenate dehydratase is isolated from a substance PF1022-producing microorganism and a target gene on the chromosome is disrupted by homologous recombination using the isolated gene to obtain the mutant strain of interest. Gene disruption can be done according to a known method.

The method for disrupting genes using homologous recombination can generally be divided into two groups, one-step gene disruption method and two-step gene disruption method. The following explanation uses a chorismate mutase gene as an example.

In a one-step gene disruption method, an insertion type vector or a replacement type vector is used.

As an insertion type vector, a vector comprising an inactivated chorismate mutase gene and a selectable marker gene to select a transformant is first prepared. The inactivated chorismate mutase gene can be a gene identical to the original chorismate mutase gene, except that a mutation that singly enables inactivation of chorismate mutase gene is introduced into two separate sites. Such an insertion type vector is introduced into a cell to select a transformant in which homologous recombination has taken place with the target chorismate mutase gene on the chromosome in the area between the two mutation sites. In such a transformant, two copies of the chorismate mutase gene exist on the chromosome. However, since the mutation is introduced into one site of each chorismate mutase gene, the chorismate mutase gene on the chromosome can be inactivated.

As a replacement type vector, a vector containing a chorismate mutase gene in which a selectable marker gene is inserted within the chorismate mutase gene so as to divide the chorismate mutase gene is prepared. This replacement type vector is introduced into a cell to select a transformant in which homologous recombination has taken place in the area derived from the chorismate mutase gene on both sides of the selectable marker gene. In such a transformant, the chorismate mutase gene on the chromosome can be inactivated since the target chorismate mutase gene is replaced with a gene having an inserted selectable marker gene.

On the other hand, in the two-step gene disruption method, in its first step, a vector comprising a chorismate mutase gene, in which at least one mutation that singly enables inactivation of the chorismate mutase gene is introduced, and a selectable marker gene is constructed. This vector is introduced into a cell to induce homologous recombination with a target chorismate mutase gene on the chromosome upstream of the mutation site of the chorismate mutase gene. As a result, the core vector containing the selectable marker gene is placed between the two copies of the target chorismate mutase gene on the chromosome. Thus, of the two copies of the target chorismate mutase gene, one has a mutation and the other has no mutation.

Next, a part of the vector between the two copies of the target chorismate mutase gene loops out and homologous recombination is induced again downstream of the mutation site. As a result, the vector containing the selectable marker gene and one copy of the target chorismate mutase gene are lost and the chorismate mutase gene on the chromosome is replaced by the target chorismate mutase gene containing a mutation, thereby inactivating the chorismate mutase gene on the chromosome. A strain having such recombination can be selected by using the loss of the marker gene as an indicator. Here, it is evident that a similar result can be obtained when homologous recombination is induced downstream region of the mutation site in the first step and then homologous recombination is induced in the upstream region.

Examples of the preferable phenylalanine auxotrophic hosts in the present invention include a phenylalanine auxotrophic mutant strain induced from a filamentous fungus strain which belongs to *Agonomycetales*, preferably a phenylalanine auxotrophic mutant strain induced from *Mycelia sterilia*, more preferably a phenylalanine auxotrophic mutant strain induced by strain PF1022 which is deposited with the National Institute of Advanced Industrial Science and Technology under an accession number of FERM BP-2671. Most preferable is a phenylalanine auxotrophic mutant strain characterized in that the strain has been induced from *Mycelia sterilia* and its phenylalanine requirement is derived from the lack of endogenous chorismate mutase activity and/or prephenate dehydratase activity.

Biosynthesis Genes

Examples of enzymes involved in the biosynthetic pathway from chorismic acid to p-aminophenylpyruvic acid include 4-amino-4-deoxychorismate synthase, 4-amino-4-deoxychorismate mutase, and 4-amino-4-deoxyprephenate dehydrogenase (Blanc, V., et al., Mol. Microbiol., 23, 191-202, 1997). The biosynthetic pathway from chorismic acid to p-aminophenylpyruvic acid can be summarized as follows.

4-amino-4-deoxychorismate synthase acts on chorismic acid to produce 4-amino-4-deoxychorismic acid; 4-amino-4-deoxychorismate mutase acts on the resulting 4-amino-4-deoxychorismic acid to produce 4-amino-4-deoxyprephenic acid; and 4-amino-4-deoxyprephenate dehydrogenase acts on the resulting 4-amino-4-deoxyprephenic acid to produce p-aminophenylpyruvic acid.

The term "4-amino-4-deoxychorismate synthase" as used herein means an enzyme that acts on chorismic acid to transform it into 4-amino-4-deoxychorismic acid. The 4-amino-4-deoxychorismate synthase is found in a wide variety of organisms as a part of the biosynthesis system from chorismic acid to p-aminobenzoic acid. P-Aminobenzoic acid is synthesized from chorismic acid in a two-step reaction. The former reaction is catalyzed by 4-amino-4-deoxychorismate synthase, and the latter reaction is catalyzed by 4-amino-4-deoxychorismate lyase (Green, J. M. and Nichols, B. P., J. Biol. Chem., 266, 12971-12975, 1991).

Reported genes encoding 4-amino-4-deoxychorismate synthase include those derived from *Escherichia coli* (Kaplan, J. B. and Nichols, B. P., J. Mol. Biol., 168, 451-468, 1983; Goncharoff, P. and Nichols, B. P., J. Bacteriol., 159, 57-62, 1984), *Bacillus subtilis* (Slock, J. et al., J. Bacteriol., 172, 7211-7226, 1990), *Klebsiella pneumoniae* (Kaplan, J. B. et al., J. Mol. Biol., 183, 327-340, 1985; Goncharoff, P. and Nichols, B. P., Mol. Biol. Evol., 5, 531-548, 1988), *Streptomyces pristinaespiralis* (Blanc, V. et al., Mol. Microbiol., 23, 191-202, 1997), *S. venezuelae* (Brown, M. P. et al., Microbiology, 142, 1345-1355, 1996), and *Saccharomyces cerevisiae* (Edman, J. C. et al., Yeast, 9, 669-675, 1993), and they can be used. Genes encoding the 4-amino-4-deoxychorismate synthase, other than those mentioned above, can also be isolated from organisms having 4-amino-4-deoxychorismate synthase activity using standard techniques and used in the present invention.

On the other hand, the 4-amino-4-deoxychorismate synthase can be generally divided into two groups: one which is composed of two polypeptides, such as those derived from *Escherichia coli*, *Bacillus subtilis*, or *Klebsiella pneumoniae*, and the other which is composed of one peptide, such as those from a part of Actinomycetes or *Saccharomyces cerevisiae*. In the present invention, it is preferable to use a gene encoding the 4-amino-4-deoxychorismate synthase consisting of one polypeptide since a plurality of genes has to be introduced to a host.

In the present invention, an example of the gene encoding the 4-amino-4-deoxychorismate synthase is preferably a gene encoding the amino acid sequence of SEQ ID NO: 2 or a modified sequence of SEQ ID NO: 2 having 4-amino-4-deoxychorismate synthase activity. More preferably, it is a gene containing the DNA sequence of SEQ ID NO: 1.

In the present invention, "modified sequence" means a sequence having one or more, for example one to several, modifications selected from the group consisting of a substitution, a deletion, an insertion, and an addition.

In the present invention, whether a modified amino acid sequence has 4-amino-4-deoxychorismate synthase activity or not can be evaluated by allowing the protein comprising said amino acid sequence to act on a substrate and then detecting the reaction product. For example, it can be evaluated according to the method described later in Example 2.

The term "4-amino-4-deoxychorismate mutase" as used herein means an enzyme that acts on 4-amino-4-deoxychorismic acid to transform it into 4-amino-4-deoxyprephenic acid.

The term "4-amino-4-deoxyprephenate dehydrogenase" as used herein means an enzyme which acts on 4-amino-4-deoxyprephenic acid to transform it into p-aminophenylpyruvic acid.

A gene encoding 4-amino-4-deoxychorismate mutase and a gene encoding 4-amino-4-deoxyprephenate dehydrogenase are obtained from organisms that can biosynthesize p-aminophenylpyruvic acid. More specifically, examples of such organisms include *Streptomyces pristinaespiralis* that produces pristinamycin I; *Streptomyces loidens* that produces vernamycin B; *Nocardia parafinnica* and *Corynebacterium hydrocarboclastus* that produce corynesin; and *Streptomyces venezuelae* that produces chloramphenicol.

Among these organisms, *Streptomyces pristinaespiralis* can be used in the present invention since genes which presumably encode 4-amino-4-deoxychorismate mutase and 4-amino-4-deoxyprephenate dehydrogenase have already been isolated and their nucleotide sequences have been determined (V. Blanc et al., Mol. Microbiol., 23, 191-202, 1997).

A number of genes encoding chorismate mutase and prephenate dehydrogenase have been already isolated from bacteria, yeasts, plants and the like, and these genes can be modified by substituting, deleting or adding appropriate amino acids so as to have 4-amino-4-deoxychorismate mutase activity and 4-amino-4-deoxyprephenate dehydrogenase activity, based on protein engineering techniques or directed evolution techniques. Thus, the resulting modified genes can also be used in the present invention.

In the present invention, an example of the gene encoding the 4-amino-4-deoxychorismate mutase is preferably a gene encoding the amino acid sequence of SEQ ID NO: 4 or a modified sequence of SEQ ID NO: 4 having 4-amino-4-deoxychorismate mutase activity, more preferably a gene containing the DNA sequence of SEQ ID NO: 3.

In the present invention, whether a modified amino acid sequence has 4-amino-4-deoxychorismate mutase activity or not can be evaluated by allowing the protein comprising said amino acid sequence to act on a substrate and then detecting the reaction product, for example, according to the method described later in Example 3.

In the present invention, an example of the gene encoding the 4-amino-4-deoxyprephenate dehydrogenase is preferably a gene encoding the amino acid sequence of SEQ ID NO: 6 or a modified sequence of SEQ ID NO: 6 having 4-amino-4-deoxyprephenate dehydrogenase activity. More preferably, it is a gene containing the DNA sequence of SEQ ID NO: 5.

In the present invention, whether a modified amino acid sequence has 4-amino-4-deoxyprephenate dehydrogenase activity or not can be evaluated by allowing the protein comprising said amino acid sequence to act on a substrate and then detecting the reaction product. For example, it can be evaluated according to the method described later in Example 4.

Given the amino acid sequences of enzymes involved in the biosynthesis in the present invention, nucleotide sequences encoding the amino acid sequences can be easily determined, and various nucleotide sequences encoding the amino acid sequences depicted in SEQ ID NO: 2; SEQ ID NO: 4, and SEQ ID NO: 6 can be selected.

Accordingly, biosynthesis genes according to the present invention include, in addition to a part or all of the DNA sequences of SEQ ID NO: 1, SEQ ID NO: 3, and SEQ ID NO: 5, DNA sequences encoding the same amino acid sequences and having degenerate codons. Further, they include RNA sequences corresponding to these sequences.

Transformants

A transformant according to the present invention means a host comprising genes involved in the biosynthetic pathway from chorismic acid to p-aminophenylpyruvic acid (biosynthesis gene). The gene to be introduced into the host means a DNA molecule, which is replicable in the host cell and in which the genes can be expressed, in particular an expression vector.

A transformed organism can be obtained by introducing a DNA molecule comprising genes involved in the biosynthetic pathway from chorismic acid to p-aminophenylpyruvic acid into the host. In the present invention, when a plurality of biosynthesis enzyme genes is introduced into the host, each gene can be contained in either the same or different DNA molecules. Further, when the host cell is a bacterium, each gene can be designed to be expressed as a polycistronic mRNA so as to be made into a single DNA molecule.

The expression vector to be used in the present invention can be appropriately selected from viruses, plasmids, cosmid vectors, and the like taking the kind of the host cell to be used into consideration. For example, lambda bacteriophages and pBR and pUC plasmids can be used when the host cell is *Escherichia coli*; pUB plasmids can be used for *Bacillus subtilis*; and YEp, YRp, YCp, and YIp plasmid vectors can be used for yeasts.

Among the plasmid vectors to be used, at least one vector preferably contains a selectable marker to select transformants. A drug resistance gene or a gene complementing an auxotrophic mutation can be used as a selectable marker. Preferable examples of the marker genes to be used for each host include an ampicillin resistance gene, a kanamycin resistance gene and a tetracycline gene for bacteria; a tryptophan biosynthesis gene (trp 1), an uracil biosynthesis gene (ura3) and a leucine biosynthesis gene (leu2) for yeasts; and a hygromycin B resistance gene, a bialaphos resistance gene, a bleomycin resistance gene and an aureobasidin resistance gene for fungi.

Furthermore, in an expression vector, DNA sequences necessary for expression of the individual genes, for example, transcription regulatory signals and translation regulatory signals, such as a promoter, a transcription initiation signal, a ribosome binding site, a translation stop signal, and a transcription stop signal, can operably be linked to the biosynthesis gene. The regulatory sequences can be selected and ligated according to an ordinary method.

For example, promoters such a lactose operon and a tryptophan operon can be used in *Escherichia coli*; promoters of an alcohol dehydrogenase gene, an acid phosphatase gene, a galactose utilization gene, and a glyceraldehyde 3-phosphate dehydrogenase gene can be used in yeasts; and promoters such as α-amylase gene, a glucoamylase gene, a cellobiohydrolase gene, a glyceraldehyde 3-phosphate dehydrogenase gene, and an Abp1 gene can be used in fungi.

Transformation of a host can be carried out according to an ordinary method such as the calcium ion method, the lithium ion method, the electroporation method, the PEG method, the *Agrobacterium* method, and the particle gun method, and the method can be selected depending on the host to be transformed.

A transformant according to the present invention is preferably a transformant producing a substance PF1022 derivative depicted by formula (III) or formula (V), characterized in that (a) it is derived from *Mycelia sterilia* producing substance PF1022 depicted by formula (I), (b) an endogenous chrismate mutase gene and/or prephenate dehydratase gene is disrupted by gene disruption, and (c) a gene involved in the biosynthetic pathway from chorismic acid to p-aminophenylpyruvic acid is introduced.

Production of Substance PF1022 Derivative

In the present invention, a transformant of the present invention is cultured, and the resultant culture is used to obtain a substance PF1022 derivative of interest. The transformant can be cultured according to an ordinary method by appropriately selecting a medium, culture conditions, and the like.

The medium can be supplemented with a carbon source and nitrogen source that can be anabolized and utilized, respectively, by the transformant of the present invention, inorganic salts, various vitamins, various amino acids such as glutamic acid and asparagine, trace nutrients such as nucleotides, and selectable agents such as antibiotics.

Further, organic and inorganic substances that help the growth of the transformant of the present invention and promote the production of the substance PF1022 derivative of the present invention can be appropriately added. Further, if necessary, a synthetic medium or complex medium which appropriately contains other nutrients can be used.

Any kind of carbon source and nitrogen source can be used in the medium as long as they can be utilized by the transformant of the present invention. As the anabolizable carbon source, for example, various carbohydrates, such as sucrose, glucose, starch, glycerin, fructose, maltose, mannitol, xylose, galactose, ribose, dextrin, animal and plant oils and the like, or hydrolysates thereof, can be used. The preferable concentration generally is from 0.1% to 5% of the medium.

As the utilizable nitrogen source, for example, animal or plant components, or exudates or extracts thereof, such as peptone, meat extract, corn steep liquor, and defatted soybean powder, organic acid ammonium salts such as succinic acid ammonium salts and tartaric acid ammonium salts, urea, and other various inorganic or organic nitrogen-containing compounds can be used.

Further, as inorganic salts, for example, those which can produce sodium, potassium, calcium, magnesium, cobalt, chlorine, phosphoric acid, sulfuric acid, and other ions can be appropriately used.

Any medium which contains other components, such as cells, exudates or extracts of microorganisms such as yeasts, and fine plant powders, can be appropriately used as long as they don't interfere with the growth of the transformant and the production and accumulation of the substance PF1022 derivative of the present invention. When a mutant strain having a nutritional requirement is cultured, a substance to satisfy its nutritional requirement is added to the medium. However, this kind of nutrient may not necessarily be added when a medium containing natural substances is used.

The pH of the medium is, for example, about 6 to 8. Incubation can be carried out by a shaking culture method under an aerobic condition, an agitation culture method with aeration or an aerobic submerged culture method.

An appropriate incubation temperature is 15° C. to 40° C., generally about 26° C. to 37° C.

Production of the substance PF1022 derivative of the present invention depends on a medium, culture conditions, or a host used. However, the maximum accumulation can generally be attained in 2 to 25 days by any culture method. The incubation is terminated when the amount of the substance PF1022 derivative of the present invention in the medium reaches its peak, and the target substance is isolated from the culture and then purified.

Needless to say, the culture conditions such as the medium component, medium fluidity, incubation temperature, agitation speed and aeration rate can be appropriately selected and controlled depending on the transformant to be used and the exterior conditions so as to obtain preferable results. If foaming occurs in a liquid medium, a defoaming agent such as silicone oil, vegetable oils, mineral oils, and surfactants can be appropriately used.

The substance PF1022 derivative of the present invention accumulated in the culture thus obtained is contained in the cells of the transformant of the present invention and the culture filtrate. Accordingly, it is possible to recover the substance PF1022 derivative of the present invention from both culture filtrate and transformant cells by separating the culture into each fraction by centrifugation.

The substance PF1022 derivative of the present invention can be recovered from the culture filtrate according to an ordinary method used for recovering the substance PF1022 derivative of the present invention from the culture. The procedures can be carried out singly, in combination in a certain order, or repeatedly. For example, extraction filtration, centrifugation, salting out, concentration, drying, freezing, adsorption, detaching, means for separation based on the difference in solubility in various solvents, such as precipitation, crystallization, recrystallization, reverse solution, counter-current distribution, and chromatography, can be used.

Further, the substance PF1022 derivative of the present invention can be obtained from the culture inside the cells of the transformant of the present invention. For example, extraction from the culture (e.g., smashing and pressure disruption), recovery (e.g., filtration and centrifugation), and purification (e.g., salting out and solvent precipitation) can be carried out using an ordinary method.

The crude substance obtained can be purified according to an ordinary method, for example, by column chromatography using a carrier such as silica gel and alumina or reverse-phase chromatography using an ODS carrier. A pure substance PF1022 derivative of the present invention can be obtained from the culture of the transformant of the present invention using the abovementioned methods, either singly or in appropriate combination.

Gene for Enzyme Involved in the Biosynthetic Pathway from Chorismic Acid to Phenylpyruvic Acid It is still another objective of the present invention to provide a novel gene for an enzyme involved in the biosynthetic pathway from chorismic acid to phenylpyruvic acid. The biosynthetic pathway from chorismic acid to phenylpyruvic acid can be summarized as follows: Chorismate mutase acts on chorismic acid to produce prephenic acid and prephenate dehydratase acts on the resulting prephenic acid to produce phenylpyruvic acid.

A novel gene according to the present invention is a polynucleotide encoding the amino acid sequence of SEQ ID NO: 27 or a modified sequence of SEQ ID NO: 27 having chorismate mutase activity, more preferably a polynucleotide comprising the DNA sequence of SEQ ID NO: 26.

In the present invention, whether a polynucleotide encodes a modified amino acid sequence having chorismate mutase activity or not can be evaluated by introducing the polynucleotide into a host (e.g., E. coli) according to known gene recombination technology for expression, allowing the resulting protein to act on a substrate and then detecting the reaction product (see Examples 2, 3, 4, and 9).

A novel gene according to the present invention is also a polynucleotide encoding the amino acid sequence of SEQ ID NO: 38 or a modified sequence of SEQ ID NO: 38 having prephenate dehydratase activity, more preferably a polynucleotide comprising the DNA sequence of SEQ ID NO: 37.

In the present invention, whether a polynucleotide encodes a modified amino acid sequence having prephenate dehydratase activity or not can be evaluated by introducing the polynucleotide into a host (e.g., E. coli) using known gene recombination technology for expression, allowing the resulting protein to act on a substrate and then detecting the reaction product (see Examples 2, 3, 4, and 17).

In the present invention, given the amino acid sequence of an enzyme involved in a biosynthetic pathway from chorismic acid to phenylpyruvic acid, nucleotide sequences encoding the amino acid sequence can be easily determined, and various nucleotide sequences encoding the amino acid sequences depicted in SEQ ID NO: 27 and SEQ ID NO: 38 can be selected. Accordingly, genes involved in a biosynthetic pathway from chorismic acid to phenylpyruvic acid according to the present invention include, in addition to a part or all of the DNA sequences of SEQ ID NO: 26 and SEQ ID NO: 37, DNA sequences encoding the same amino acid sequences and having degenerate codons. Further, they include RNA sequences corresponding to these sequences.

EXAMPLE

The present invention is further illustrated by the following examples that are not intended as a limitation, and various changes and modifications fall within the scope of the invention.

Example 1

Isolation of a gene encoding 4-amino-4-deoxychorismate synthase, a gene encoding 4-amino-4-deoxychorismate mutase, and a gene encoding 4-amino-4-deoxyprephenate dehydrogenase from *Streptomyces venezuelae*

(1) Preparation of Probe DNA Fragment

A 50 ml portion of a liquid medium (2% soluble starch, 1% polypeptone, 0.3% meat extract, 0.05% potassium dihydrogenphosphate, pH 7.0) was prepared in a 250-ml Erlenmeyer flask. The ISP5230 strain and 140-5 strain of *Streptomyces venezuelae* were each inoculated into this medium and cultured at 28° C. for 24 hours. After culturing, the cells were harvested from the culture by centrifugation, and the chromosome DNA was prepared from these cells by the method described in Genetic Manipulation of *Streptomyces*, A Laboratory Manual (D. A. Hopwood et al., The John Innes Foundation, p71-78, 1985).

Next, PCR was carried out using the above-mentioned chromosomal DNA of the *Streptomyces venezuelae* strain ISP5230 as a template and oligonucleotides of SEQ ID NO: 7 and SEQ ID NO: 8 as primers. The PCR was carried out with a TaKaRa LA PCR™ kit Ver. 2.1 (Takara Shuzo Co., Ltd.) and Gene Amp PCR System 2400 (Perkin-Elmer). A reaction solution containing 1 µl of the chromosomal DNA (equivalent to 0.62 µg), 5 µl of 10-fold concentrated reaction buffer attached to the kit, 8 µl of a 2.5 mM dNTP solution, 0.5 µl each of the above-mentioned primers prepared at a concentration of 100 pmol/µl, 5 µl of dimethyl sulfoxide (Wako Pure Chemical Industries, Ltd.), 0.5 µl of TaKaRa LA-Taq (2.5 U), and 29.5 µl of sterile water was made up into a total volume of 50 µl. The reaction was carried out by repeating incubation of 25 cycles of one minute at 94° C., one minute at 50° C. and 3 minutes at 72° C., after pretreatment at 94° C. for 10 minutes. After the reaction, a portion of the reaction solution was subjected to agarose gel electrophoresis to confirm that a DNA fragment of approximately 2 kbp was specifically amplified. Then, the remaining reaction solution was extracted with phenol:chloroform:isoamyl alcohol (25:24:1) and precipitated with ethanol. The precipitate was redissolved in sterile water, and the resulting solution (60 µl) was digested with restriction enzyme BamHI, after which agarose gel electrophoresis was carried out, and a band of approximately 2 kbp was isolated according to an ordinary method to recover a DNA fragment.

This DNA fragment was cloned into the BamHI site of plasmid pTrcHis B (Invitrogen). Since the restriction map of the inserted fragment of the resulting plasmid was identical to that of pabAB gene (U21728) reported by Brown et al. (M. P. Brown et al., Microbiology, 142, 1345-1355, 1996), the pabAB gene was considered to be cloned, and the plasmid was named pTH-PAB. The plasmid pTH-PAB was digested with restriction enzyme BamHI, agarose gel electrophoresis was carried out, and an insertion fragment was isolated and recovered to be used as a probe for the screening of a chromosomal DNA library described below.

(2) Screening of Chromosomal DNA Library and Isolation of Genes

About 10 µg of the chromosomal DNA of the *Streptomyces venezuelae* 140-5 strain was partly digested with restriction enzyme Sau3AI, after which agarose gel electrophoresis was carried out to isolate and recover DNA fragments of from 10 kbp to 20 kbp.

About 0.5 µg of the DNA fragments of from 10 kbp to 20 kbp thus recovered and 1 µg of λDASH II previously doubledigested with restriction enzymes BamHI and XhoI were ligated with T4 DNA ligase and then packaged in vitro using a Gigapack III packaging extract (Stratagene) to construct a chromosomal DNA library. Plaques were formed by infecting *Escherichia coli* XLI-Blue MRA with this DNA library.

Plaque hybridization was carried out using the DNA fragment of approximately 2 kbp isolated in (1) as a probe and an ECL Direct DNA/RNA Labeling Detection System (Amersham Pharmacia Biotech) to screen about 24000 plaques. Among positive clones thus obtained, ten clones were subjected to a secondary screening, and the resulting positive clones were purified to prepare phage DNAs.

These phage DNAs were digested with restriction enzyme BamHI, and Southern analysis was carried out, which revealed that the probe was hybridized with two kinds of DNA fragments, i.e., fragments of approximately 1.8 kbp and approximately 3.4 kbp. Further, restriction map analysis of the phage DNAs revealed that these two kinds of DNA fragments were adjoining on the chromosomal DNA.

Next, the entire nucleotide sequences of these two kinds of DNA fragments were determined using a fluorescent DNA sequencer ABI PRISM 377 (Perkin-Elmer). As a result of the subsequent open-reading-frame (ORF) search, ORFs I-IV were found as shown in FIG. 1. The amino acid sequences deduced from each of the ORFs were searched for homology with known amino acid sequences using database, which revealed that ORF I was homologous to p-aminobenzoic acid-synthesizing enzyme, ORF II was homologous to prephenate dehydrogenase, and ORF III was homologous to chorismate mutase. Genes of ORF I, II and III were then named papA, papC and papB, respectively. nucleotide sequence of papA are each shown in SEQ ID The amino acid sequence encoded by papA and the NO: 2 and SEQ ID NO: 1; the amino acid sequence encoded by papB and the nucleotide sequence of papB are each shown in SEQ ID NO: 4 and SEQ ID NO: 3; and the amino acid sequence encoded by papC and the nucleotide sequence of papC are each shown in SEQ ID NO: 6 and SEQ ID NO: 5.

Example 2

Expression of papA Gene in *Escherichia coli*

In order to obtain the translation region of the papA gene, PCR was carried out with the phage DNA derived from the positive clone shown in Example 1 as a template and oligonucleotides of SEQ ID NO: 9 and SEQ ID NO: 10 as primers. The PCR was carried out with KOD Dash (Toyobo Co., Ltd.) as DNA polymerase using the Gene Amp PCR System 9700 (Perkin-Elmer). A reaction solution containing 1 µl of phage DNA (equivalent to 1 µg), 5 µl of 10-fold concentrated reaction buffer attached to the enzyme, 5 µl of a 2 mM dNTP solution, 1 µl each of the above-mentioned primers prepared at a concentration of 100 pmol/µl, 5 µl of dimethyl sulfoxide (Wako Pure Chemical Industries, Ltd.), 1 µl of KOD Dash, and 31 µl of sterile water was made up into a total volume of 50 µl. The reaction was carried out by repeating incubation of 15 cycles of 30 seconds at 94° C., 2 seconds at 50° C. and 30 seconds at 72° C., after pretreatment at 94° C. for 5 minutes. The reaction solution thus obtained was extracted with phenol:chloroform:isoamyl alcohol (25:24:1) and precipitated with ethanol. The precipitate was redissolved in sterile water, and the DNA terminals were blunted using a DNA blunting kit (Takara Shuzo Co., Ltd.). Further, the 5' end was phosphorylated using T4 DNA kinase (Wako Pure Chemical Industries, Ltd.), after which agarose gel electrophoresis was carried out, a DNA fragment of approximately 2 kbp was isolated, recovered, and cloned into the SmaI site of plasmid pUC118 to obtain plasmid pUC118-papA (FERM BP-7256).

The nucleotide sequence of the inserted fragment of pUC118-papA (FERM BP-7256) was determined using a fluorescent DNA sequencer ABI PRISM 310 Genetic Analyzer (Perkin-Elmer). As a result, it was revealed that cytosine at position 2043 in the nucleotide sequence of SEQ ID NO: 1 was replaced by adenine. Since this replacement was believed to be an error upon amplification of the DNA fragment by PCR and brought no change in the amino acid sequence to be encoded, the inserted fragment of pUC118-papA (FERM BP-7256) was used for the following experiment.

pUC118-papA (FERM BP-7256) was introduced into *Escherichia coli* JM110, and a plasmid was prepared from the resultant transformant using an ordinary method. After digesting with restriction enzyme BclI, agarose gel electrophoresis was carried out to isolate and recover a BclI DNA fragment of approximately 2 kbp.

Figure 2:
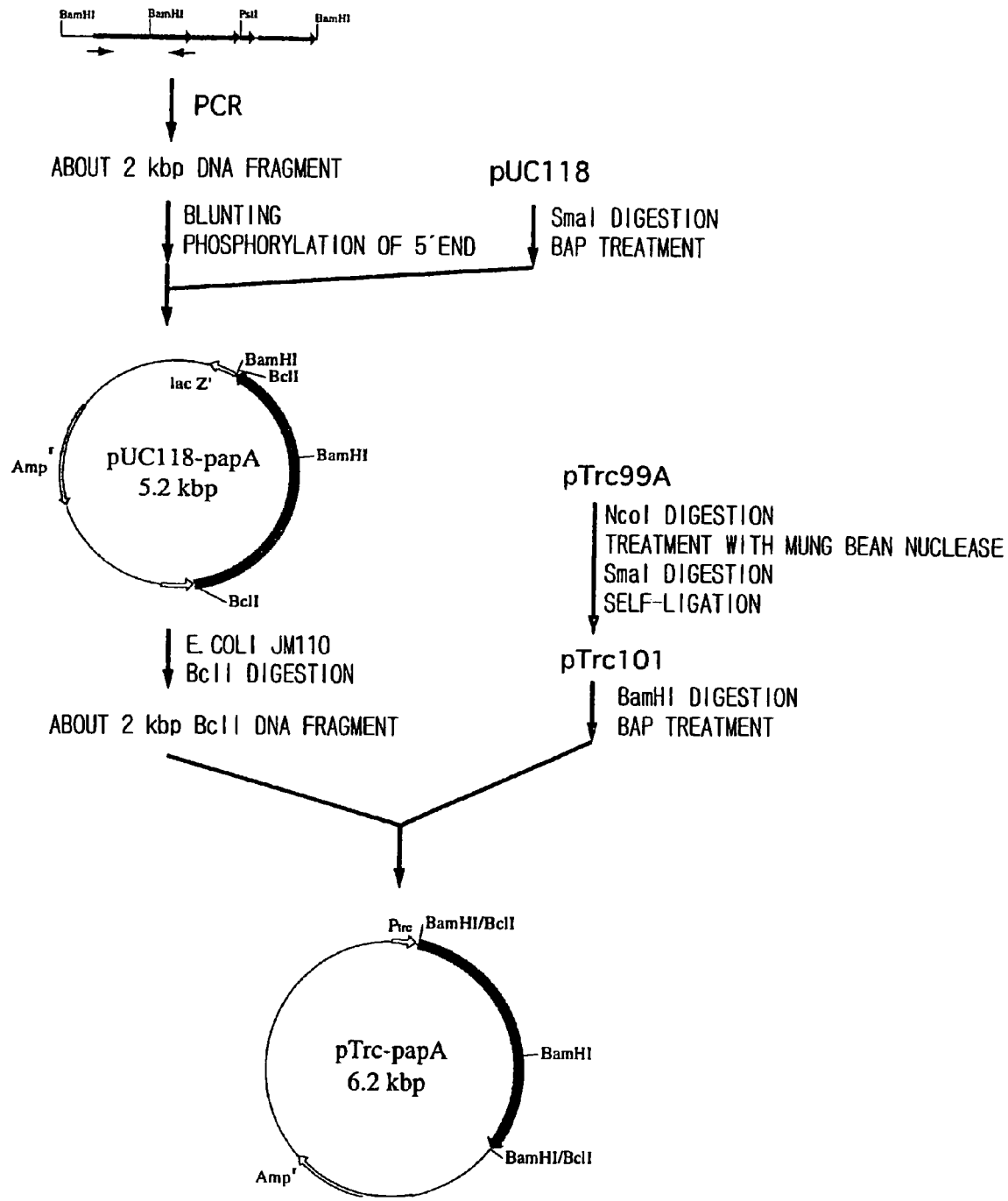
FIG. 2 shows the construction of plasmid pTrc-papA.

On the other hand, plasmid pTrc99A (Amersham Pharmacia Biotech) was digested with restriction enzyme NcoI, and the DNA terminals were blunted using Mung Bean Nuclease (Wako Pure Chemical Industries, Ltd.). The resultant fragment was further digested with restriction enzyme SmaI and then self-ligated using T4 DNA ligase to obtain plasmid pTrc101.

pTrc101 was digested with restriction enzyme BamHI and treated with alkaline phosphatase (Takara Shuzo Co., Ltd.), after which the resultant fragment was ligated to the above-mentioned 2 kbp BclI DNA fragment. A plasmid into which the papA gene was inserted in the correct orientation to the promoter contained in pTrc101 was selected and named pTrc-papA. FIG. 2 shows the process of the above-mentioned plasmid construction.

The *Escherichia coli* JM109 strain carrying pTrc-papA was cultured in an LB liquid medium (1% Bacto-tryptone, 0.5% yeast extract, 0.5% sodium chloride) supplemented with 100 μg/ml ampicillin, at 37° C. overnight. A 1 ml portion of the resultant culture was inoculated into 100 ml of the same medium, and incubation was carried out at 30° C. for 4 hours, after which 1 ml of 100 mM isopropylthiogalactoside (IPTG) was added, and incubation was further carried out at 30° C. for 3 hours. After incubation, cells were recovered from the culture by centrifugation, suspended in 4 ml of buffer solution for cell homogenization (50 mM Tris-HCl (pH 8.0), 5 mM EDTA, 10% glycerol) and then homogenized by ultrasonic treatment. After homogenization, the supernatant was recovered by centrifugation to obtain a cell extract. Further, the *Escherichia coli* JM109 strain carrying plasmid pTrc101 was treated in the same manner to prepare another cell extract.

The cell extracts thus prepared were measured for their enzymatic activity. Namely, 100 μl of the cell extract, 400 μl of distilled water, and 500 μl of a substrate solution [10 mM barium chorismate (Sigma), 10 mM glutamine (Wako Pure Chemical Industries, Ltd.), 10 mM magnesium chloride, 100 mM MOPS (Wako Pure Chemical Industries, Ltd.), pH 7.5] were mixed and reacted at 30° C. for 2 hours. After reaction, a portion of the reaction solution was analyzed using a full automatic amino acid analyzer JLC-500/V (JEOL, Ltd.).

Figure 3:
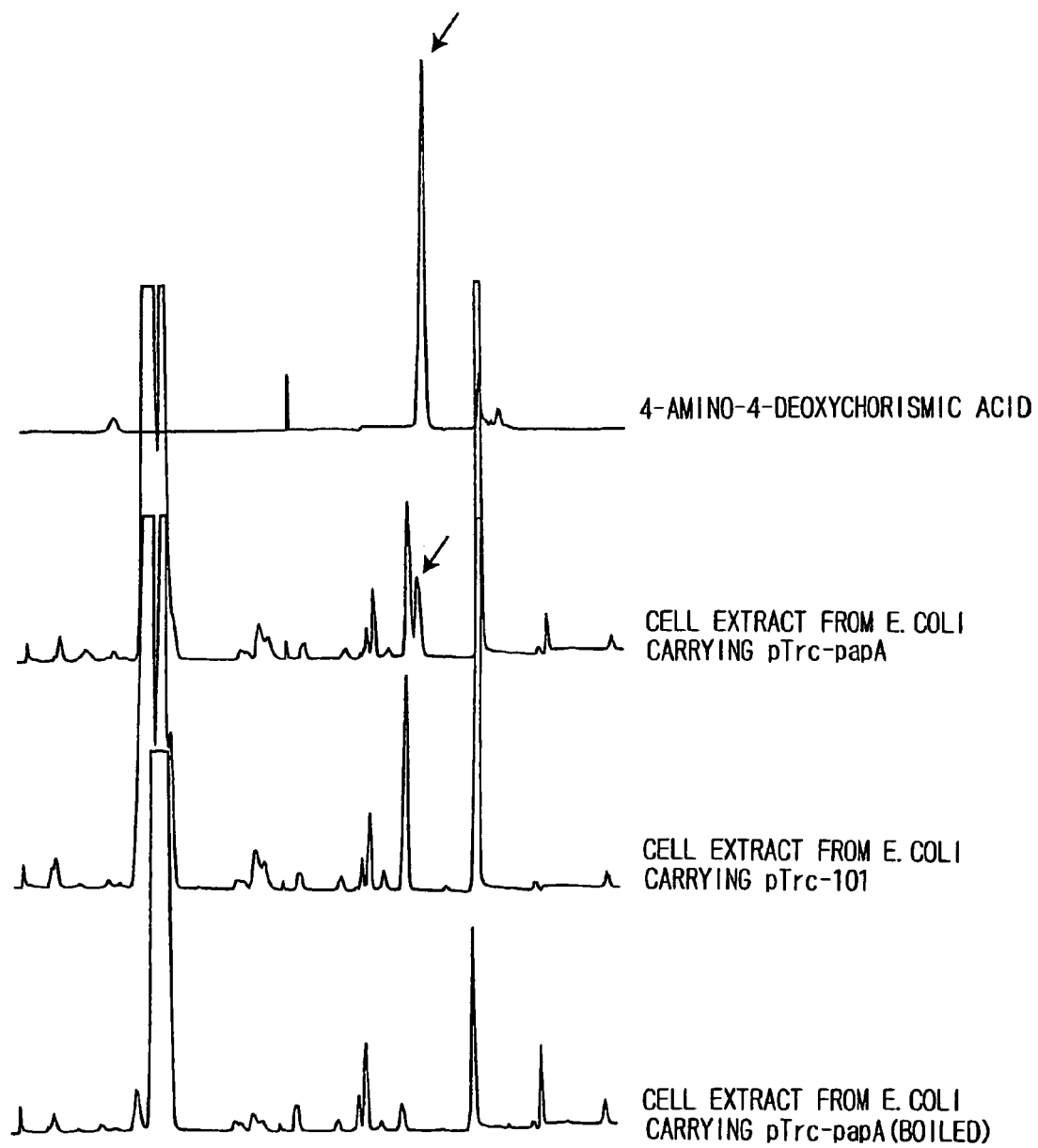
FIG. 3 shows the amino acid analyzer chromatograms used for detecting enzyme activity of a papA gene product.

As shown in FIG. 3, when the cell extract prepared from the *Escherichia coli* carrying pTrc-papA was used, a peak was detected on a position showing the same retention time with a standard for 4-amino-4-deoxychorismic acid synthesized according to the method of Chia-Yu P. Teng et al. (Chia-Yu P. Teng et al., J. Am. Chem. Soc., 107, 5008-5009, 1985). On the other hand, the peak on that position was not found when the cell extract was boiled or when the cell extract prepared from the *Escherichia coli* carrying pTrc101 was used. Thus, the papA gene was verified to encode 4-amino-4-deoxychorismate synthase.

Example 3

Expression of papB Gene in *Escherichia coli*

In order to obtain the translation region of the papB gene, PCR was carried out with the phage DNA derived from the positive clone shown in Example 1 as a template and oligonucleotides of SEQ ID NO: 11 and SEQ ID NO: 12 as primers. The PCR was carried out with KOD Dash (Toyobo Co., Ltd.) as DNA polymerase using GeneAmp PCR System 9700 (Perkin-Elmer). A reaction solution containing 1 μl of phage DNA (equivalent to 1 μg), 5 μl of 10-fold concentrated reaction buffer attached to the enzyme, 5 μl of a 2 mM dNTP solution, 1 μl each of the above-mentioned primers prepared at a concentration of 100 pmol/μl, 5 μl of dimethyl sulfoxide (Wako Pure Chemical Industries, Ltd.), 1 μl of KOD Dash and 31 μl of sterile water was made up into a total volume of 50 μl. The reaction was carried out by repeating incubation of 15 cycles of 30 seconds at 94° C., 2 seconds at 50° C. and 30 seconds at 72° C., after pretreatment at 94° C. for 5 minutes. The reaction solution thus obtained was extracted with phenol:chloroform:isoamyl alcohol (25:24:1) and precipitated with ethanol. The precipitate was redissolved in sterile water and digested with restriction enzyme BamHI, after which agarose gel electrophoresis was carried out, and a DNA fragment of approximately 0.3 kbp was isolated according to an ordinary method to recover a DNA fragment.

pTrc101 was digested with restriction enzyme BamHI and treated with alkaline phosphatase (Takara Shuzo Co., Ltd.), after which the resultant fragment was ligated to the above-mentioned 0.3-kbp BamHI DNA fragment using T4 DNA ligase. A plasmid into which the papB gene was inserted in the correct orientation to the promoter contained in pTrc101 was selected and named pTrc-papB (FIG. 4). The nucleotide sequence of the inserted fragment of pTrc-papB (FERM BP-7257) was determined using a fluorescent DNA sequencer ABI PRISM 310 Genetic Analyzer (Perkin-Elmer) to verify that the sequence was identical with the nucleotide sequence of SEQ ID NO: 3.

The *Escherichia coli* JM109 strain carrying pTrc-papB (FERM BP-7257) was cultured in an LB liquid medium (1% Bacto-tryptone, 0.5% yeast extract, 0.5% sodium chloride) supplemented with 100 μg/ml ampicillin, at 37° C. overnight. A 1 ml portion of the resultant culture was inoculated into 100 ml of the same medium, and incubation was carried out at 37° C. for 2 hours, after which 1 ml of 100 mM isopropylthiogalactoside (IPTG) was added, and incubation was further carried out at 37° C. for 5 hours. After incubation, cells were recovered from the culture by centrifugation, suspended in 4 ml of buffer solution for cell homogenization (50 mM Tris-HCl (pH 8.0), 5 mM EDTA, 10% glycerol), and then homogenized by ultrasonic treatment. After homogenization, the supernatant was recovered by centrifugation to obtain a cell extract. Further, the *Escherichia coli* JM109 strain carrying plasmid pTrc101 was treated in the same manner to prepare a cell extract.

The cell extracts thus prepared were measured for their enzymatic activity. Namely, 50 μl of the cell extract, 200 μl of distilled water, and 250 μl of a substrate solution [2 mg/ml 4-amino-4-deoxychorismic acid, 10 mM magnesium chloride, 100 mM MOPS (Wako Pure Chemical Industries, Ltd.), pH 7.5] were mixed and reacted at 30° C. for 1 hour. After reaction, a portion of the reaction solution was analyzed using a full automatic amino acid analyzer JLC-500/V (JEOL, Ltd.).

Figure 5:
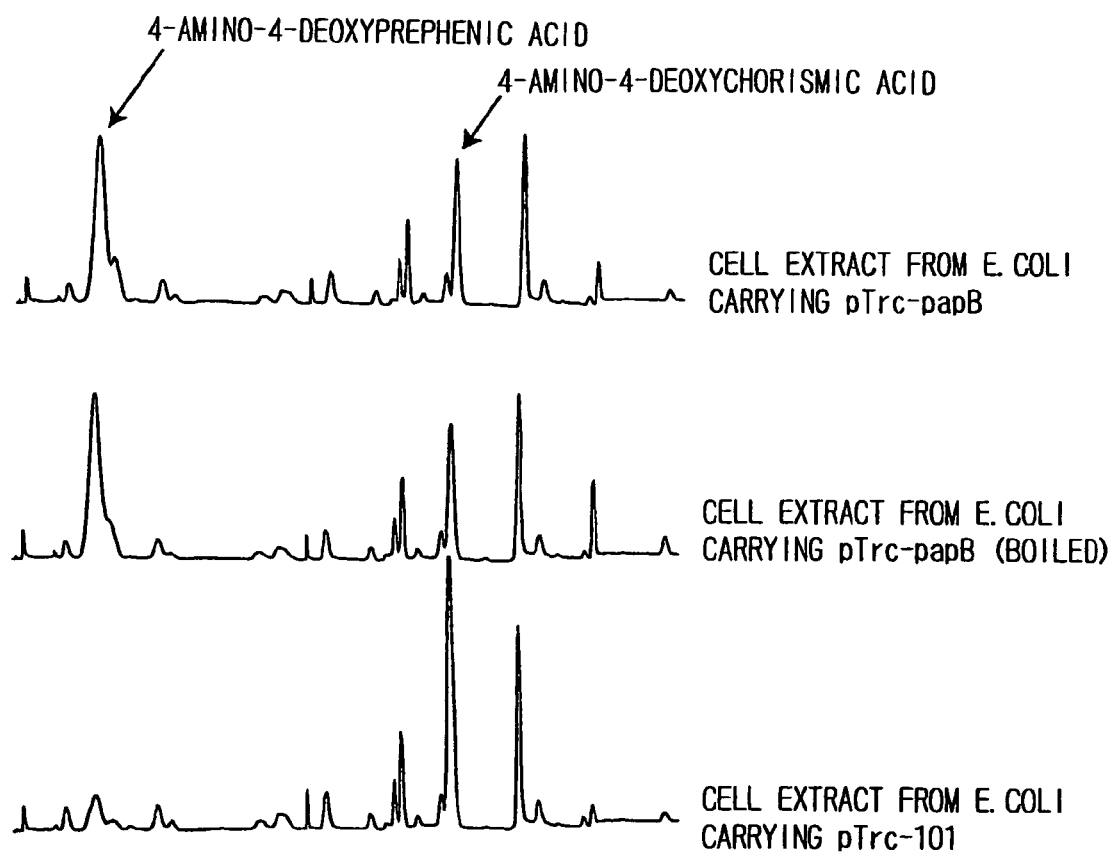
FIG. 5 shows the amino acid analyzer chromatograms used for detecting enzyme activity of a papB gene product.

As shown in FIG. 5, when the cell extract prepared from the *Escherichia coli* carrying pTrc-papB (FERM BP-7257) was used, the peak for 4-amino-4-deoxychorismic acid declined and the peak for 4-amino-4-deoxyprephenic acid was newly detected. A similar result was obtained when the cell extract boiled for 5 minutes was used.

On the other hand, when the cell extract prepared from the *Escherichia coli* carrying pTrc101 was used, there was no change in the peak for 4-amino-4-deoxychorismic acid, and the peak for 4-amino-4-deoxyprephenic acid was not detected. Thus, these results revealed that the papB gene encodes 4-amino-4-deoxychorismate mutase and that the 4-amino-4-deoxychorismate mutase encoded by the papB gene had heat-resistant activity which was not lost even after boiling for 5 minutes.

Example 4

Expression of papC Gene in *Escherichia coli*

In order to obtain the translation region of the papC gene, PCR was carried out using the phage DNA derived from the positive clone shown in Example 1 as a template and oligonucleotides of SEQ ID NO: 13 and SEQ ID NO: 14 as primers. The PCR was carried out with KOD Dash (Toyobo Co., Ltd.) as DNA polymerase using GeneAmp PCR System 9700 (Perkin-Elmer). A reaction solution containing 1 µl of phage DNA (equivalent to 1 µg), 5 µl of 10-fold concentrated reaction buffer attached to the enzyme, 5 µl of a 2 mM dNTP solution, 1 µl each of the above-mentioned primers prepared at a concentration of 100 pmol/µl, 5 µl of dimethyl sulfoxide (Wako Pure Chemical Industries, Ltd.), 1 µl of KOD Dash and 31 µl of sterile water was made up into a total volume of 50 µl. The reaction was carried out by repeating incubation of 15 cycles of 30 seconds at 94° C., 2 seconds at 50° C. and 30 seconds at 72° C., after pretreatment at 94° C. for 5 minutes. The reaction solution thus obtained was extracted with phenol:chloroform:isoamyl alcohol (25:24:1) and precipitated with ethanol. The precipitate was redissolved in sterile water, and digested with restriction enzyme BamHI, after which agarose gel electrophoresis was carried out, and a DNA fragment of approximately 1 kbp was isolated according to an ordinary method to recover a DNA fragment.

Plasmid pET-11c (Stratagene) was digested with restriction enzyme BamHI and treated with alkaline phosphatase (Takara Shuzo Co., Ltd.), after which the resultant fragment was ligated to the above-mentioned 1 kbp BamHI DNA fragment using T4 DNA ligase. A plasmid into which the papC gene was inserted in the correct orientation to the promoter contained in pET-11c (FERM BP-7258) was selected and named pET-papC.

The nucleotide sequence of the inserted fragment of pET-papC (FERM BP-7258) was determined using a fluorescent DNA sequencer ABI PRISM 310 Genetic Analyzer (Perkin-Elmer) to verify that the sequence was identical with the nucleotide sequence of SEQ ID NO: 5.

On the other hand, when the papC gene was expressed using pET-papC (FERM BP-7258), evaluation of properties of papC gene products was expected to be difficult since the vector-derived peptide composed of 14 amino acids was added to the N-terminal side of the papC gene products. Therefore, pET-papC (FERM BP-7258) was digested with restriction enzyme NdeI, after which plasmid pET-papC1 was obtained by self-ligation using T4 DNA ligase. Use of pET-papC1 made it possible to produce papC gene products by themselves and not as fusion proteins. The above-mentioned plasmid construction process is shown in FIG. 6.

The *Escherichia coli* BL21 (DE3) strain carrying pET-papC1 was cultured in an LB liquid medium (1% Bacto-tryptone, 0.5% yeast extract, 0.5% sodium chloride) supplemented with 100 µg/ml ampicillin, at 37° C. overnight. A 1 ml portion of the resultant culture was inoculated into 100 ml of the same medium, and incubation was carried out at 37° C. for 2 hours, after which 1 ml of 100 mM isopropylthiogalactoside (IPTG) was added, and incubation was further carried out at 37° C. for 5 hours. After incubation, cells were recovered by centrifugation, suspended in 4 ml of buffer solution for cell homogenization (50 mM Tris-HCl (pH 8.0), 5 mM EDTA, 10% glycerol), and then homogenized by ultrasonic treatment. After homogenization, the supernatant was recovered by centrifugation to obtain a cell extract. Further, the *Escherichia coli* BL21 (DE3) strain carrying plasmid pET-11c was treated in the same manner to prepare a cell extract.

The cell extracts thus prepared were measured for their enzymatic activity. Namely, 40 µl of the cell extract, 10 µl of the cell extract which was prepared from the *Escherichia coli* carrying pTrc-papB (FERM BP-7257) described in Example 3 and boiled, 190 µl of distilled water, 10 µl of a 10 mM NAD solution, and 250 µl of a substrate solution [2 mg/ml 4-amino-4-deoxychorismic acid, 10 mM magnesium chloride, 100 mM MOPS (Wako Pure Chemical Industries, Ltd.), pH 7.5] were mixed and reacted at 30° C. for 1 hour. After reaction, a portion of the reaction solution was analyzed using a full automatic amino acid analyzer JLC-500/V (JEOL, Ltd.).

Figure 7:
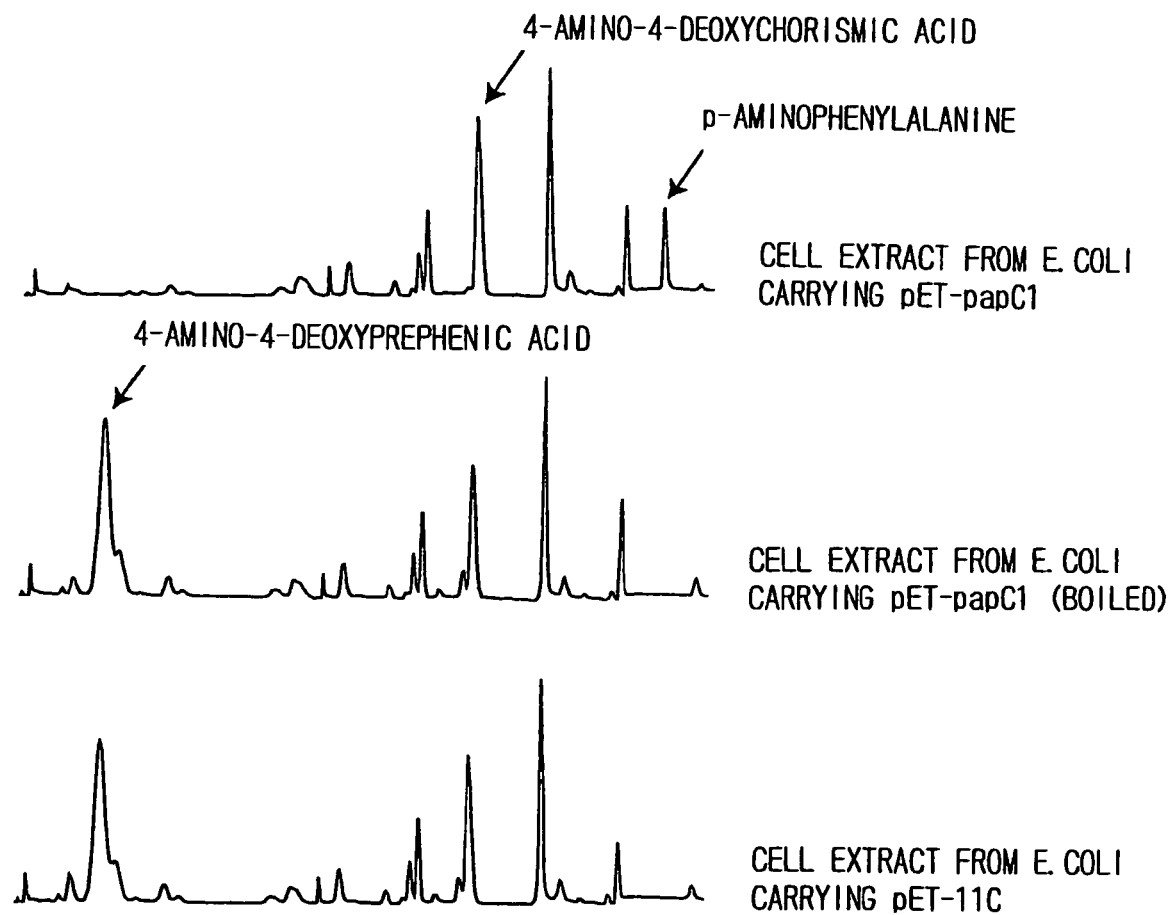
FIG. 7 shows the amino acid analyzer chromatograms used for detecting enzyme activity of a papC gene product.

As shown in FIG. 7, when the cell extract prepared from the *Escherichia coli* carrying pET-papC1 was used, the peak for 4-amino-4-deoxychorismic acid declined, and the peak for 4-amino-4-deoxyprephenic acid to be generated by the papB gene products disappeared. Since p-aminophenylpyruvic acid cannot be detected by the full automatic amino acid analyzer JLC-500/V, its synthesis could not directly be confirmed.

However, a peak for p-aminophenylalanine was detected. This was generated probably due to the transfer of an amino group of p-aminophenylpyruvic acid generated from papC gene products, by *Escherichia coli* aminotransferase. On the other hand, when the cell extract boiled and the cell extract which was prepared from the *Escherichia coli* carrying pET-11c were used, there was no change in the peak for 4-amino-4-deoxyprephenic acid generated from papB gene products. Thus, it was revealed that the papC gene coded for 4-amino-4-deoxyprephenate dehydrogenase.

Example 5

Construction of Plasmids pPF260-A3 and pPF260-A4 for Introduction into Phenylalanine Auxotrophic Microorganism Plasmids pPF260-A3 and pPF260-A4 for expressing the papA gene in a phenylalanine auxotrophic microorganism were constructed as shown in FIG. 8.

An expression vector pABPd for a PF1022-producing microorganism was constructed, and then the DNA fragment obtained from plasmid pUC118-papA (FERM BP-7256) described in Example 2 was ligated to this vector to obtain an expression vector. More specifically, the expression vector was constructed as described below.

Isolation of Genomic DNA of Substance PF1022-Producing Microorganism

The genomic DNA of the PF1022 strain (FERM BP-2671) was isolated according to the method of Horiuchi et al. (H. Horiuchi et al., J. Bacteriol., 170, 272-278, 1988). More specifically, cells of the substance PF1022-producing strain (FERM BP-2671) were cultured for 2 days in a seed medium (2.0% soluble starch, 1.0% glucose, 0.5% polypeptone, 0.6% wheat germ, 0.3% yeast extract, 0.2% soybean cake, and 0.2% calcium carbonate; pH 7.0 before sterilization; see Example 1 in WO 97/00944), and the cells were recovered by centrifugation (3500 rpm, 10 minutes).

The cells thus obtained were lyophilized, suspended in a TE solution (10 mM Tril-HCl (pH 8.0), 1 mM EDTA), treated in a 3% SDS solution at 60° C. for 30 minutes, and then subjected to a phenol:chloroform:isoamylalcohol extraction (25:24:1) to remove the cell debris. The extract was precipitated with ethanol and treated with Ribonuclease A (Sigma) and Proteinase K (Wako Pure Chemical Industries, Ltd.), and then the nucleic acid was precipitated with 12% polyethylene glycol 6000. The precipitate was subjected to TE-saturated phenol extraction and ethanol precipitation, and the resulting precipitate was dissolved in a TE solution to obtain the genomic DNA.

Construction of Genome Library of Substance PF1022-Producing Microorganism

The genomic DNA derived from the PF1022 strain (FERM BP-2671) prepared as described above was partially digested with Sau3AI. The product was ligated to the BamHI arm of a phage vector, λEMBL3 Cloning Kit (Stratagene) using T4 ligase (Ligation Kit Ver. 2; Takara Shuzo Co., Ltd.). After ethanol precipitation, the precipitate was dissolved in a TE buffer. The entire ligated mixture was used to infect Escherichia coli LE392 strain using a Gigapack III Plus Packaging Kit (Stratagene) to form phage plaques. The $1.3 \times 10^4$ ($2.6 \times 10^4$ PFU/ml) phage library obtained by this method was used for cloning of the Abp1 gene.

Cloning of the Abp1 Gene from the Genomic DNA Derived from Substance PF1022-Producing Microorganism A probe to be used was prepared by amplifying the translation region of the Abp1 gene by the PCR method. The PCR was carried out using the genomic DNA prepared from the substance PF1022-producing microorganism as described above as a template and synthetic primers 8-73U and 8-73R, according to a LETS GO PCR kit (SAWADY Technology). The PCR reaction for amplification was conducted by repeating 25 cycles of 30 seconds at 94° C., 30 seconds at 50° C., and 90 seconds at 72° C. DNA sequences of the 8-73U and 8-73R are as follows:
8-73U: CTCAAACCAGGAACTCTTTC (SEQ ID NO: 15)
8-73R: GACATGTGGAAACCACATTTTG (SEQ ID NO: 16)

Figure 9:
FIG. 9 shows the restriction map of a 6-kb HindIII fragment containing a Abp1 gene.

The PCR product thus obtained was labeled using an ECL Direct System (Amersham Pharmacia Biotech). The phage plaque prepared as described above was transferred to a Hybond N+ nylon transfer membrane (Amersham Pharmacia Biotech), and after alkaline denaturation, the membrane was washed with 5×SSC(SSC: 15 mM trisodium citrate, 150 mM sodium chloride) and dried to immobilize the DNA. According to the kit protocol, prehybridization (42° C.) was carried out for 1 hour, after which the above-mentioned labeled probe was added, and hybridization was carried out at 42° C. for 16 hours. The nylon membrane was washed according to the kit protocol described above. The washed nylon membrane was immersed for one minute in a detection solution and then photosensitized on a medical X-ray film (Fuji Photo Film Co., Ltd.) to obtain one positive clone. Southern blot analysis of this clone showed that a HindIII fragment of at least 6 kb was identical with the restriction enzyme fragment long of the genomic DNA. FIG. 9 shows the restriction map of this HindIII fragment. The HindIII fragment was subcloned into pUC119 to obtain pRQHin/119 for use of the following experiment.

Construction of Expression Vector

The promoter region and the terminator region of the Abp1 gene were amplified by the PCR method using pRQHin/119 as a template. The PCR method was carried out using a PCR Super Mix High Fidelity (Lifetech Oriental Co., Ltd.) with primers ABP-Neco and ABP-Nbam for promoter amplification and ABP-Cbam and ABP-Cxba for terminator amplification. The amplification reaction was conducted by repeating 25 cycles of 30 seconds at 94° C., 30 seconds at 50° C. and 90 seconds at 72° C. The DNA sequences of ABP-Neco, ABP-Nbam, ABP-Cbam and ABP-Cxba are as follows:
ABP-Neco: GGGGAATTCGTGGGTGGTGATAT-CATGGC (SEQ ID NO: 17)
ABP-Nbam: GGGGGATCCTTGATGGGTTTTGGG (SEQ ID NO: 18)
ABP-Cbam: GGGGGATCCTAAACTCCCATCTATAGC (SEQ ID NO: 19)
ABP-Cxba: GGGTCTAGACGACTCATTGCAGT-GAGTGG (SEQ ID NO: 20)

Figure 10:
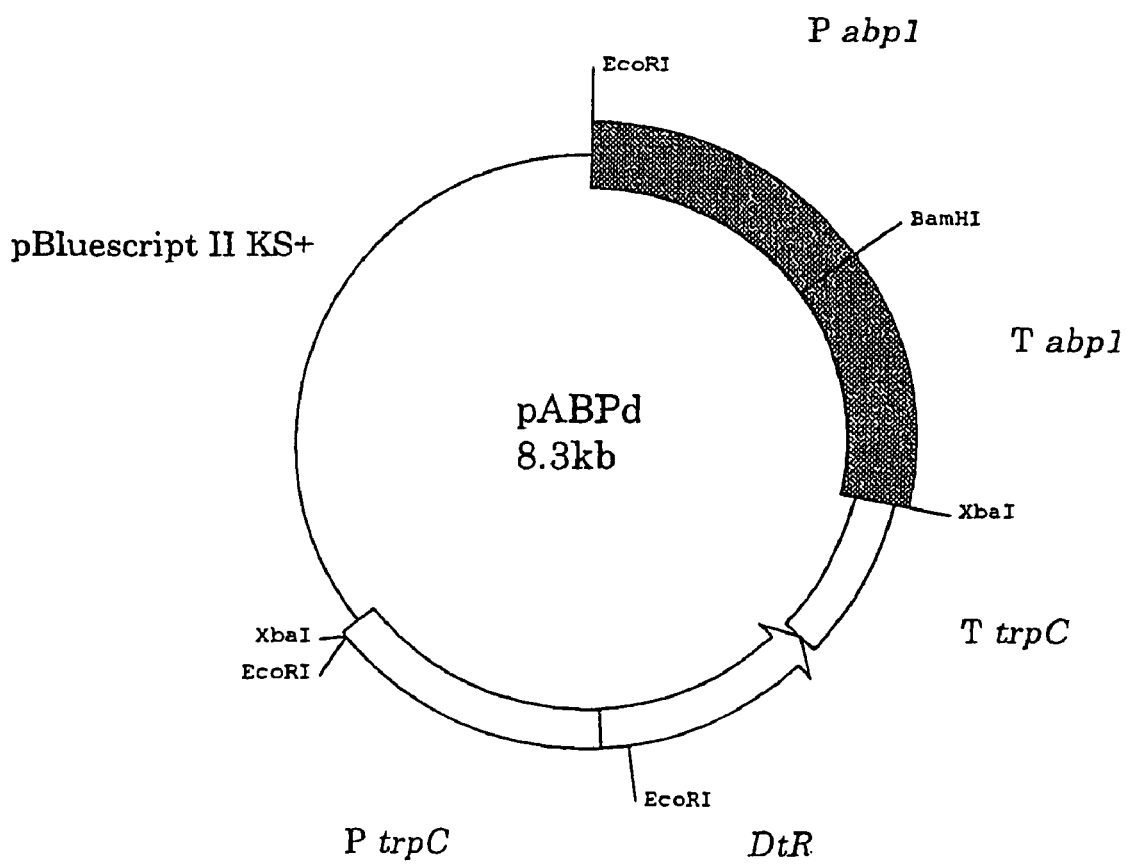
FIG. 10 shows the restriction map of plasmid pABPd.

Each PCR product was purified with a Microspin S-400 column (Amersham Pharmacia Biotech) and precipitated with ethanol, after which the promoter was double-digested with EcoRI and BamHI, the terminator was double-digested with BamHI and XbaI, and the resulting fragments were ligated one by one to pBluescript II KS+ previously digested with the same enzymes. The product was digested with XbaI, and a destomycin resistance cassette derived from pMKD01 (WO 98/03667, FERM BP-5974) was inserted to construct pABPd (FIG. 10). pABPd has the promoter and terminator of the Abp1 gene.

An approximately 2 kbp BclI DNA fragment was prepared from plasmid pUC118-papA (FERM BP-7256) described in Example 2. This fragment was inserted into the BamHI site of the expression vector pABPd for substance PF1022-producing microorganism to obtain plasmid pPF260-A.

Next, pPF260-A was double-digested with restriction enzymes PstI and BamHI to prepare a DNA fragment of approximately 1.7 kbp. This fragment was subcloned into PstI and BamHI sites of pUC119 to obtain plasmid pUC119-A. Treatment for site-directed mutagenesis was carried out with pUC119-A as a template DNA and the oligonucleotide of SEQ ID NO: 21 as a primer using a Muta-Gene in vitro Mutagenesis Kit (Bio-Rad) to obtain plasmid pUC119-A1.

Next, pUC119-A1 and pPF260-A were double-digested with restriction enzymes PstI and BamHI to prepare DNA fragments of approximately 1.7 kbp and approximately 8.6 kbp, and then these fragments were ligated to obtain plasmid pPF260-A2. Further, pPF260-A2 was digested with restriction enzyme XbaI and then self-ligated using T4 DNA ligase to obtain plasmid pPF260-A3. Next, plasmid pDHBAR (Watanabe, M. et al., Appl. Environ. Microbiol., 65, 1036-1044 (1999)) was digested with restriction enzyme XbaI to obtain an approximately 2.5 kbp DNA fragment. This fragment was digested with restriction enzyme XbaI and the obtained fragment was ligated with plasmid pPF260-A3 treated with a phosphatase to obtain plasmid pPF260-A4.

Example 6

Figure 11:
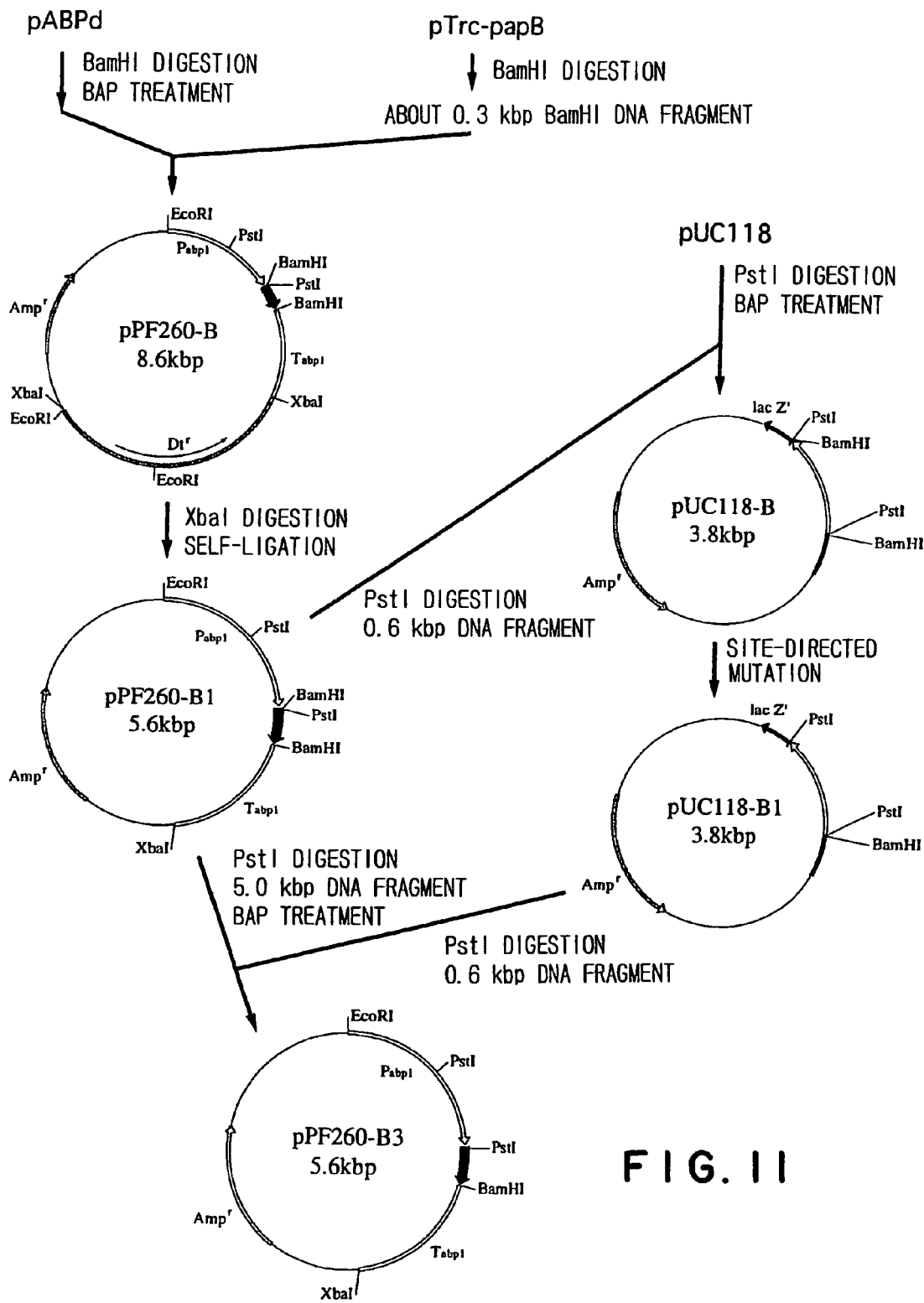
FIG. 11 shows the construction of plasmid pPF260-B3.

Construction of Plasmid pPF260-B3 for Introduction into Phenylalanine Auxotrophic Microorganism Plasmid pPF260-B3 for expressing the papB gene in a phenylalanine auxotrophic microorganism was constructed as shown in FIG. 11.

An approximately 0.3 kbp BamHI DNA fragment was prepared from plasmid pTrc-papB (FERM BP-7257) described in Example 3. This fragment was inserted into the BamHI site of the expression vector pABPd (Example 5) to obtain plasmid pPF260-B. pPF260-B was digested with restriction enzyme XbaI and then self-ligated using T4 DNA ligase to obtain plasmid pPF260-B1.

Next, pPF260-B1 was digested with restriction enzyme PstI to prepare a DNA fragment of approximately 0.6 kbp. This fragment was subcloned into the PstI site of pUC118 in such a manner that the papB gene and the lacZ' gene aligned in the same direction to obtain plasmid pUC118-B. Treatment for site-directed mutagenesis was carried out with pUC118-B as a template DNA and the oligonucleotide of SEQ ID NO: 22 as a primer using a Muta-Gene in vitro Mutagenesis Kit (Bio-Rad) to obtain plasmid pUC118-B1.

Next, pUC118-B1 and pPF260-B1 were digested with restriction enzyme PstI to prepare DNA fragments of approximately 0.6 kbp and approximately 8.0 kbp, and then these fragments were ligated to obtain plasmid pPF260-B3.

Example 7

Figure 12:
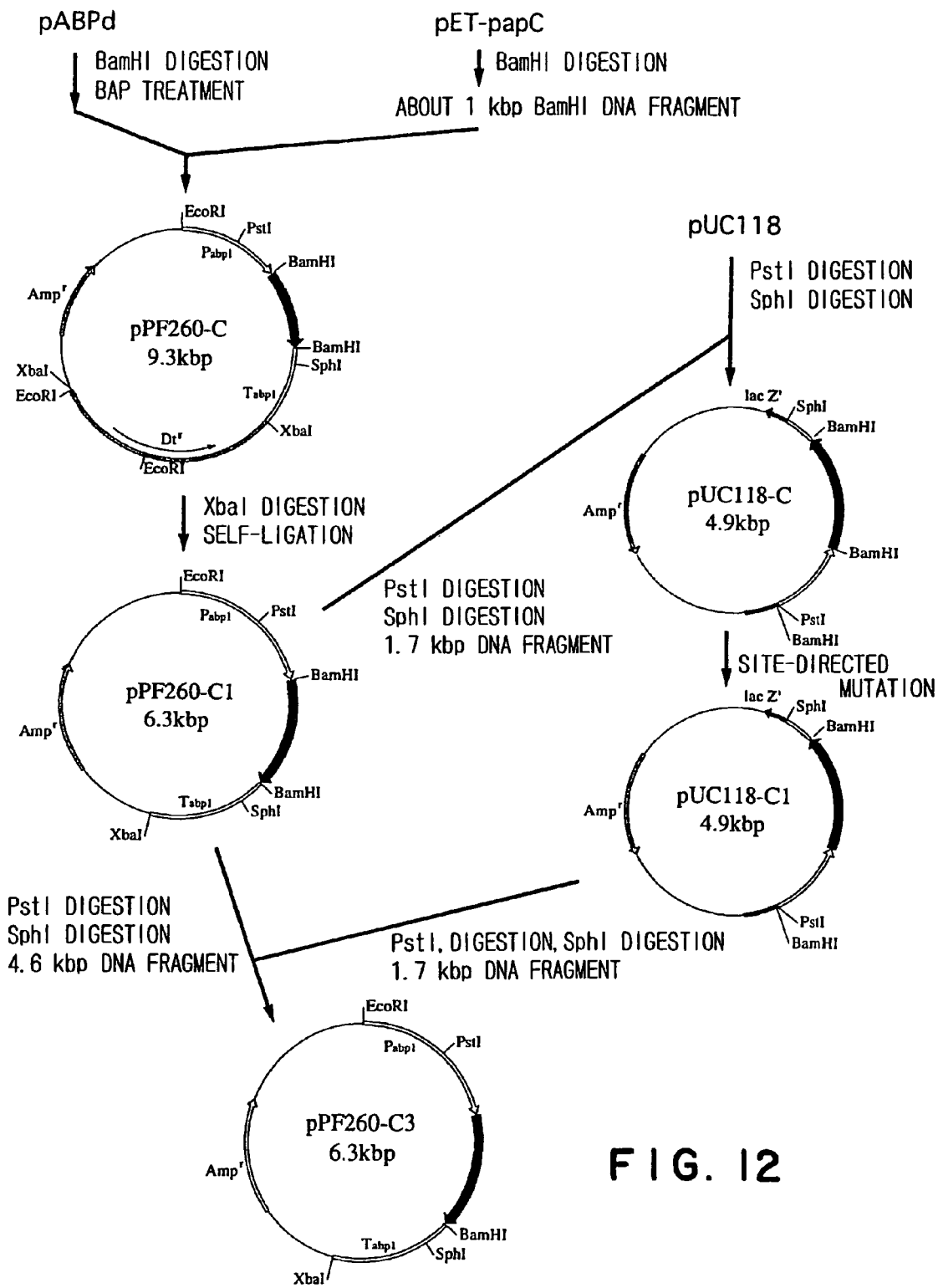
FIG. 12 shows the construction of plasmid pPF260-C3.

Construction of Plasmid pPF260-C3 for Introduction into Phenylalanine Auxotrophic Microorganism Plasmid pPF260-C3 for expressing the papC gene in a phenylalanine auxotrophic microorganism was constructed as shown in FIG. 12.

An approximately 1 kbp BamHI DNA fragment was prepared from plasmid pET-papC (FERM BP-7258) described in Example 4. This fragment was inserted into the BamHI site of the expression vector pABPd (Example 5) to obtain plasmid pPF260-C. pPF260-C was digested with restriction enzyme XbaI and then self-ligated using T4 DNA ligase to obtain plasmid pPF260-C1.

Next, pPF260-C1 was double-digested with restriction enzymes PstI and SphI to prepare a DNA fragment of approximately 1.7 kbp. This fragment was subcloned into the PstI and SphI sites of pUC118 to obtain plasmid pUC118-C. Treatment for site-directed mutagenesis was carried out with pUC118-C as a template DNA and the oligonucleotide of SEQ ID NO: 23 as a primer using a Muta-Gene in vitro mutagenesis kit (Bio-Rad) to obtain plasmid pUC118-C1.

Next, pUC118-C1 and pPF260-C1 were double-digested with restriction enzymes PstI and SphI to prepare DNA fragments of approximately 1.7 kbp and approximately 7.6 kbp, and then these fragments were ligated using T4 DNA ligase to obtain plasmid pPF260-C3.

Example 8

Isolation of Chorismate Mutase Gene Derived from Substance PF1022-Producing Microorganism A chorismate mutase gene derived from a substance PF1022-producing microorganism was isolated as follows.

Amplification of Partial Gene Fragment by PCR

Amino acid sequences of chorismate mutase derived from *Arabidopsis thariana* and *Saccharomyces cerevisiae* were compared to search for highly homologous parts. As a result, since amino acid residues 159-164 and 244-249 of the amino acid sequence of chorismate mutase derived from *Saccharomyces cerevisiae* were highly homologous, oligonucleotides extrapolated from these sequences were synthesized. They are shown below.

CMUC-U: CAYTWYGGNAARTTYGT (SEQ ID NO: 24)
CMUD-L: TAYTCNACYTSNACYTC (SEQ ID NO: 25)
(N: A, G, C or T, R: A or G, S: G or C, W: A or T, Y: C or T)

Here in the synthesis, inosine was used for base 9 in CMUC-U and base 6 in CMUD-L. Next, cDNA to be used as a template in PCR was prepared as follows.

The PF1022 strain (FERM BP-2671) was cultured in the medium and under the conditions described in Example 5 and the resulting cells were recovered by centrifugation (3000 rpm, 10 minutes). The cells were washed with purified water, frozen at −80° C. and then disrupted with a blender (Nippon Seiki, AM-3) in the presence of liquid nitrogen. The resulting product was suspended in a denaturation solution (4 M guanidine thiocyanate, 25 mM trisodium citrate, 0.5% N-lauryl sarcocine sodium salt, 0.1 M mercaptoethanol) and the suspension was stirred at room temperature for 5 minutes, neutralized with 2 M sodium acetate (pH 4.5), and further stirred, adding TE-saturated phenol. Here, chloroform-isoamyl alcohol (24:1) was added and the admixture was stirred and then centrifuged to isolate the cell component denatured with phenol. The upper layer (water layer) was recovered and nucleic acid was precipitated with isopropanol.

This precipitate was dissolved in a TE buffer solution (10 mM Tris-HCl (pH 8.0), 1 mM EDTA) to make a nucleic acid concentration of 1 mg/ml, and precipitated with 2.5 M lithium chloride (5° C., 2 hours). The precipitate was recovered by centrifugation, washed with 70% ethanol, and then redissolved in the TE buffer solution to obtain a total RNA fraction. mRNA was purified from the total RNA fraction using an mRNA purification kit (Amersham Pharmacia Biotech). Further, cDNA was synthesized with this mRNA as a template using a Time Saver cDNA synthesis kit (Amersham Pharmacia Biotech).

PCR was carried out with the cDNA of the PF1022 strain (FERM BP-2671) as a template using a SuperTaq premix kit (Sawaday Technology). The PCR, touch down PCR, was performed by repeating 7 cycles of 1 minute at 94° C., 2 minutes at 50° C., and 2 minutes at 72° C. after heat denaturation treatment at 94° C. for 1 minute, then gradually decreasing annealing temperature each time by 3° C. up to a total of 28 cycles.

As a result, a fragment of approximately 270 bp was amplified. This fragment was subjected to agarose gel electrophoresis and a fragment of interest was purified using a Sephagrass band prep kit (Pharmacia Biotech). This fragment was ligated to a pT7-blue T vector (Novagen). The resulting sequence was analyzed using an Auto read sequencing kit and an ALF DNA sequencer II (Pharmacia Biotech). The result showed that this PCR fragment contained amino acid residues 171-251 of the sequence of SEQ ID NO: 27.

Cloning of Chorismate Mutase Gene by Plaque Hybridization

The chromosomal DNA library of the PF1022 strain (FERM BP-2671) described in Example 5 was transferred onto a HyBond-N+ (Amersham) and plaque hybridization was carried out using the abovementioned PCR fragment of approximately 270 bp as a probe according to a DIC system (Behringer Mannheim). As a result, 6 kinds of positive clones were obtained. Of these 6 kinds of positive clone, an XbaI fragment of approximately 7 kbp showing the same length of restriction enzyme fragment as Southern blot analysis for chromosomal DNA of the PF1022 strain (FERM BP-2671) was cloned into pUC18 to obtain plasmid pCM-Xba.

Nucleotide sequence analysis was carried out with this plasmid using an ABIPRISM 377 sequencer (Applied Biosystems). FIG. 13 shows the restriction map of the XbaI fragment and the location of the chorismate mutase gene. The presence of one intron in the chorismate mutase gene was inferred from the nucleotide sequence analysis, and its presence was confirmed by cDNA analysis. The nucleotide sequence of the chorismate mutase gene and the amino acid sequence deduced from the nucleotide sequence were shown in SEQ ID NO: 26 and SEQ ID NO: 27, respectively.

Example 9

Figure 14:
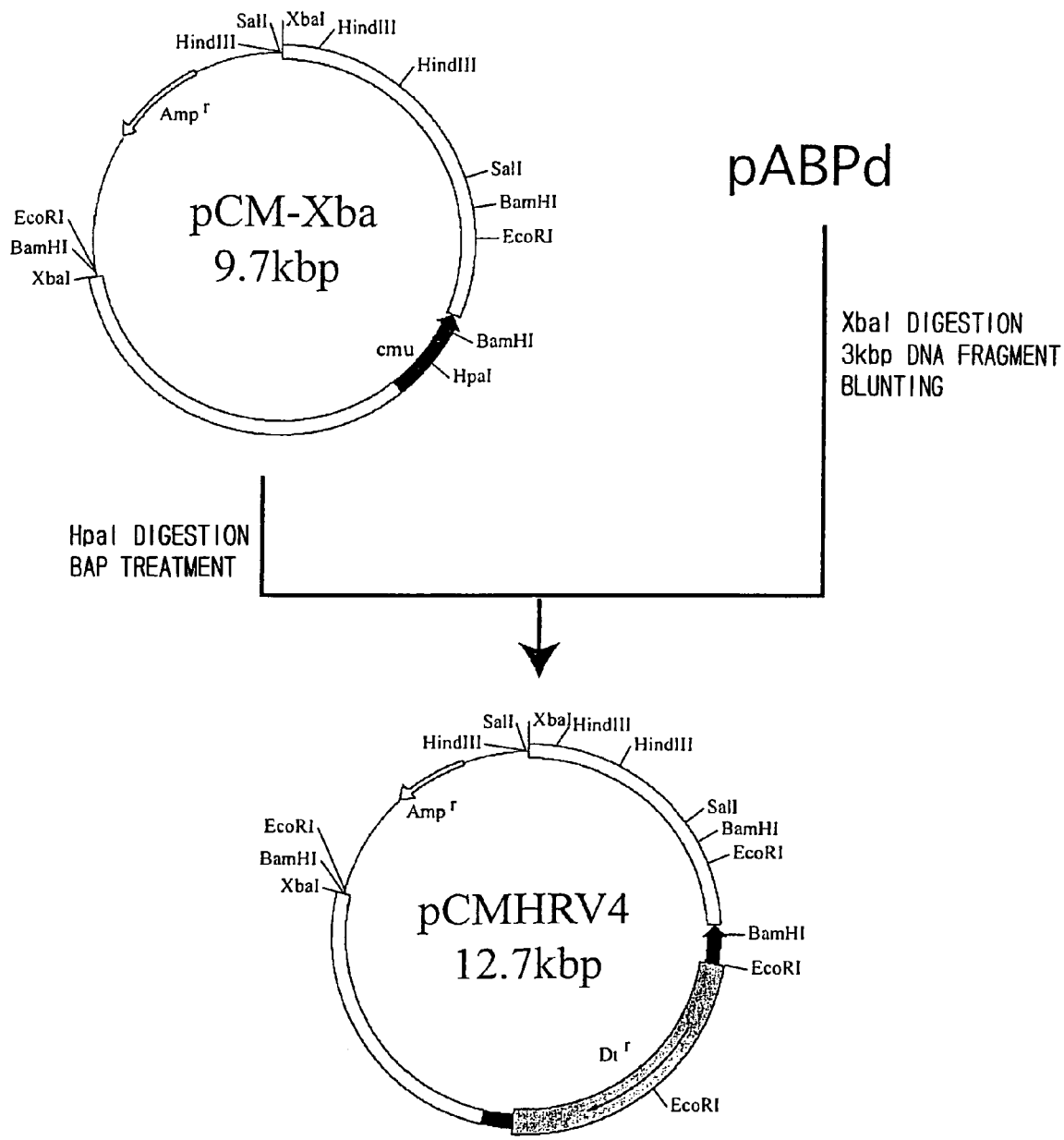
FIG. 14 shows the construction of plasmid pCMHRV4.

Disruption of Chorismate Mutase Gene of Substance PF1022-Producing Microorganism A plasmid for disrupting the chorismate mutase was prepared as shown in FIG. 14. Plasmid pABPd (FIG. 10) described in Example 5 was digested with restriction enzyme XbaI to prepare a DNA fragment of approximately 3 kbp containing a destomycin resistance gene. This DNA fragment was blunted by treating with Mung Bean Nuclease (Nippon Gene). Next, plasmid pCM-Xba described in Example 8 was digested with restriction enzyme HpaI, treated with phosphatase, and then ligated to the abovementioned blunted DNA fragment to construct plasmid pCMHRV4.

Plasmid pCMHRV4 was digested with restriction enzyme XbaI and then subjected to agarose gel electrophoresis to extract and purify a DNA fragment of approximately 10 kbp. This DNA was then dissolved in a TE buffer solution (10 mM Tris-HCl (pH 8.0), 1 mM EDTA) to make a concentration of 1 µg/ml. This DNA solution was used for the following transformation experiment.

The substance PF1022-producing microorganism was transformed according to the method described in Example 1 of WO97/00944. More specifically, strain PF1022 (FERM BP-2671) was cultured at 26° C. for 48 hours in the seed medium described in Example 5. After cultivation, the resulting mycelia were collected by centrifugation (3000 rpm, 10 minutes) and washed with a 0.5 M sucrose solution. The mycelia thus obtained were subjected to protoplast generation by shaking in a 0.5 M sucrose solution containing 3 mg/ml β-glucuronidase (Sigma), 1 mg/ml chitinase (Sigma) and 1 mg/ml zymolyase (Seikagaku Kogyo) at 30° C. for 2 hours. The mixture thus obtained was filtered to remove the cell debris. The protoplasts were washed twice by centrifugation (2500 rpm, 10 minutes, 4° C.) with an SUTC buffer solution (0.5 M sucrose, 10 mM Tris-HCl (pH 7.5), 10 mM calcium chloride), and then a $1 \times 10^7$/ml protoplast suspension was prepared with the SUTC buffer solution.

The previously prepared DNA solution was added to 100 µl of the protoplast suspension, and the resulting mixture was allowed to stand under ice-cooling for 5 minutes. Then, 400 µl of a polyethylene glycol solution (60% polyethylene glycol 4000 (Wako Pure Chemical Industries, Ltd.), 10 mM Tris-HCl (pH 7.5), 10 mM calcium chloride) was added to this mixture, and the resulting admixture was allowed to stand under ice-cooling for 20 minutes.

The protoplasts treated as described above were washed with the SUTC buffer solution and resuspended in the same buffer solution. The resulting suspension was double-layered onto a potato dextrose agar medium containing 25 µg/ml hygromycin B and 0.5 M sucrose, together with a potato dextrose soft agar medium. Incubation was carried out at 26° C. for 5 days, and colonies appeared were deemed to be transformants.

When the resulting transformants were seeded on a minimal medium (0.5% glucose, 0.67% yeast nitrogen base w/o amino acids (Difco), 0.12% sodium glutamate, 0.14% asparagine, 2 µg/ml coline chloride, 1.5% purified agar (Sigma)), there was a strain which did not grow (strain V4M-11). On the other hand, when the strain V4M-11 was seeded on the minimal medium supplemented with 50 µg/ml phenylalanine, the growth recovery was observed. Accordingly, the strain V4M-11 was revealed to be auxotrophic to phenylalanine.

Next, chorismate mutase activity of the strain V4M-11 was measured as follows. The parent strain and the strain V4M-11 were cultured under the same conditions as described in Example 5, after which cells were collected by centrifugation and suspended in a buffer solution for cell disruption (50 mM Tris-HCl (pH 8.0), 5 mM EDTA, 1 mM DTT, 1 mM PMSF, 10% glycerol). This suspension was treated with ultrasonication and the supernatant was recovered by centrifugation to obtain a cell extract. 30 µl of the cell extract, 20 µl of 1 M Tris-HCl (pH 8.0), and 50 µl of 2 mM barium chorismate (Sigma) were mixed and held at 30° C. for 1 hour.

Next, 100 µl of 1 N hydrochloric acid were added and the admixture was held at 30° C. for 15 minutes, after which 800 µl of 1 N sodium hydroxide solution were added and the optical density of the solution was measured at 320 nm. A sample in which 2 mM barium chorismate was added after adding 1 N hydrochloric acid was used as a control. The result is shown in Table 1 below.

TABLE 1

| Strain | A320 | | |
|---|---|---|---|
| | After reaction | Control | ΔA320 |
| Parent strain | 0.363 | 0.203 | 0.160 |
| V4M-11 | 0.190 | 0.203 | −0.013 |

The result above revealed that the strain V4M-11 lacked chorismate mutase activity.

Example 10

Transformation of Chorismate Mutase Gene-Disrupted Strain of PF1022-Producing Microorganism (Phenylalanine Auxotrophic Host)

A mixture of 1 µg of pPF260-A4, 3 µg of pPF260-A3, 3 µg of pPF260-B3, and 3 µg of pPF260-C3 was precipitated with ethanol and then redissolved in 10 µl of a TE buffer solution (10 mM Tris-HCl (pH 8.0), 1 mM EDTA). The DNA solution thus prepared was used to transform the strain V4M-11 according to the method described in Example 9, except that 50 µg/ml bialaphos was added instead of hygromycin B.

Chromosomal DNAs were obtained from the resulting transformants, and PCR was carried out using them as a template DNA under the same conditions as described in Examples 2, 3 and 4, except that 25 cycles were repeated, to detect the papa, papB and papC genes. As a result, strain TF-57 was selected as a transformant into which all of the three genes were introduced.

Example 11

Cultivation of Transformant and Detection of PF1022-220

The transformant strain TF-57 selected in Example 10 was cultured as described in WO 97/20945. Namely, cells were cultured at 26° C. for 2 days in the seed medium described in Example 5. A 2 ml portion of each resultant culture was inoculated into 50 ml of a production medium (0.6% wheat germ, 1.0% pharma media, 2.6% soluble starch, 6.0% starch syrup, 0.2% $MgSO_4 \cdot 7H_2O$, 0.2% NaCl), and incubation was further carried out at 26° C. for 6 days. After incubation, the resulting cells were collected from a 40 ml portion of the culture by centrifugation and then extracted with 30 ml of ethyl acetate. The extract was concentrated by drying and redissolved in 4 ml of methanol. A 10 µl portion of the solution was subjected to HPLC analysis.

Figure 15B:
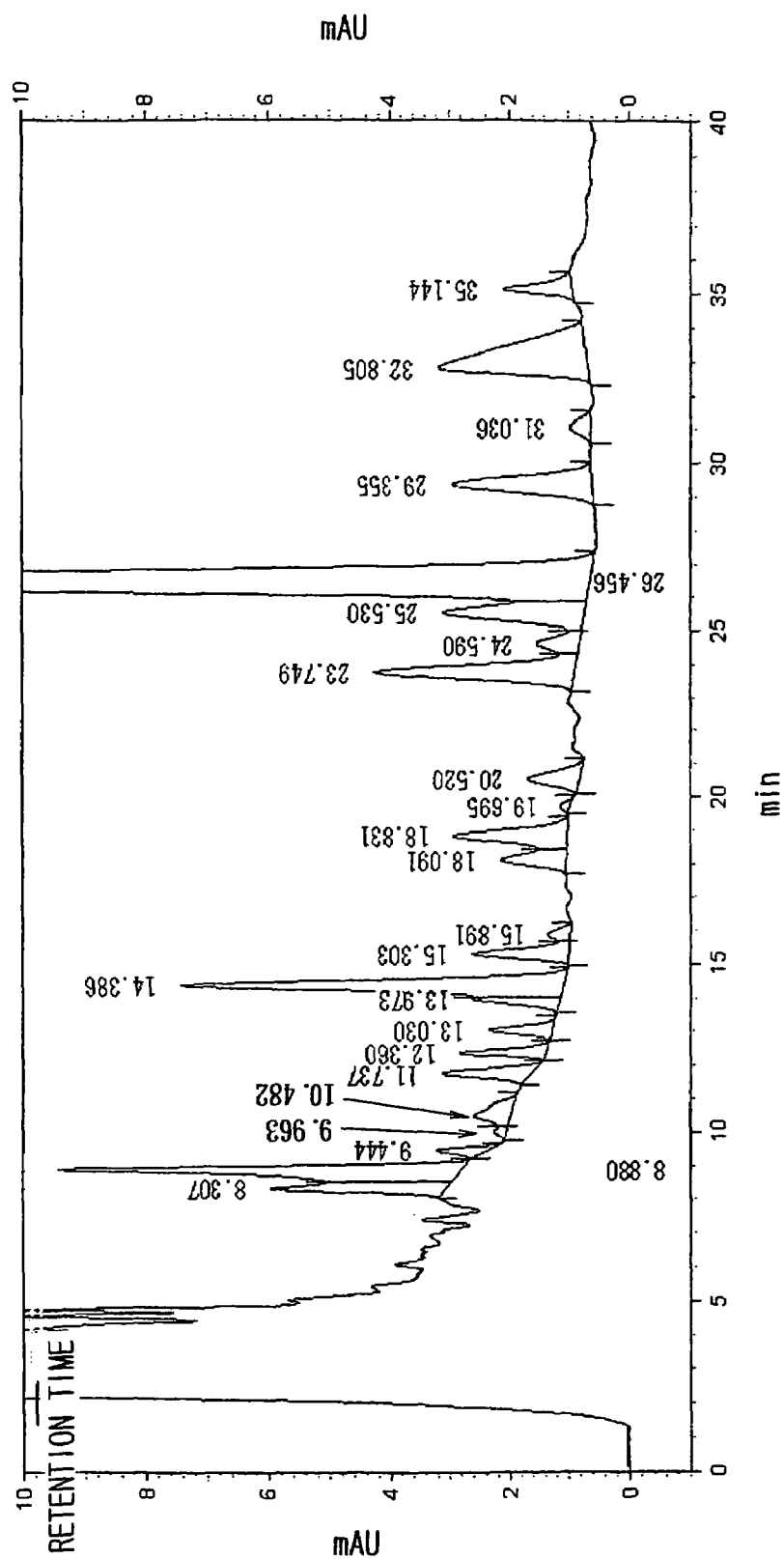
FIG. 15 shows the HPLC chromatograms used for detecting a substance PF1022 derivative, PF1022-220. A is the chromatogram for standard PF1022-220, B is the chromatogram for the sample prepared from the transformant, and C is the chromatogram for the sample prepared from the transformant and standard PF1022-220.
Figure 15C:
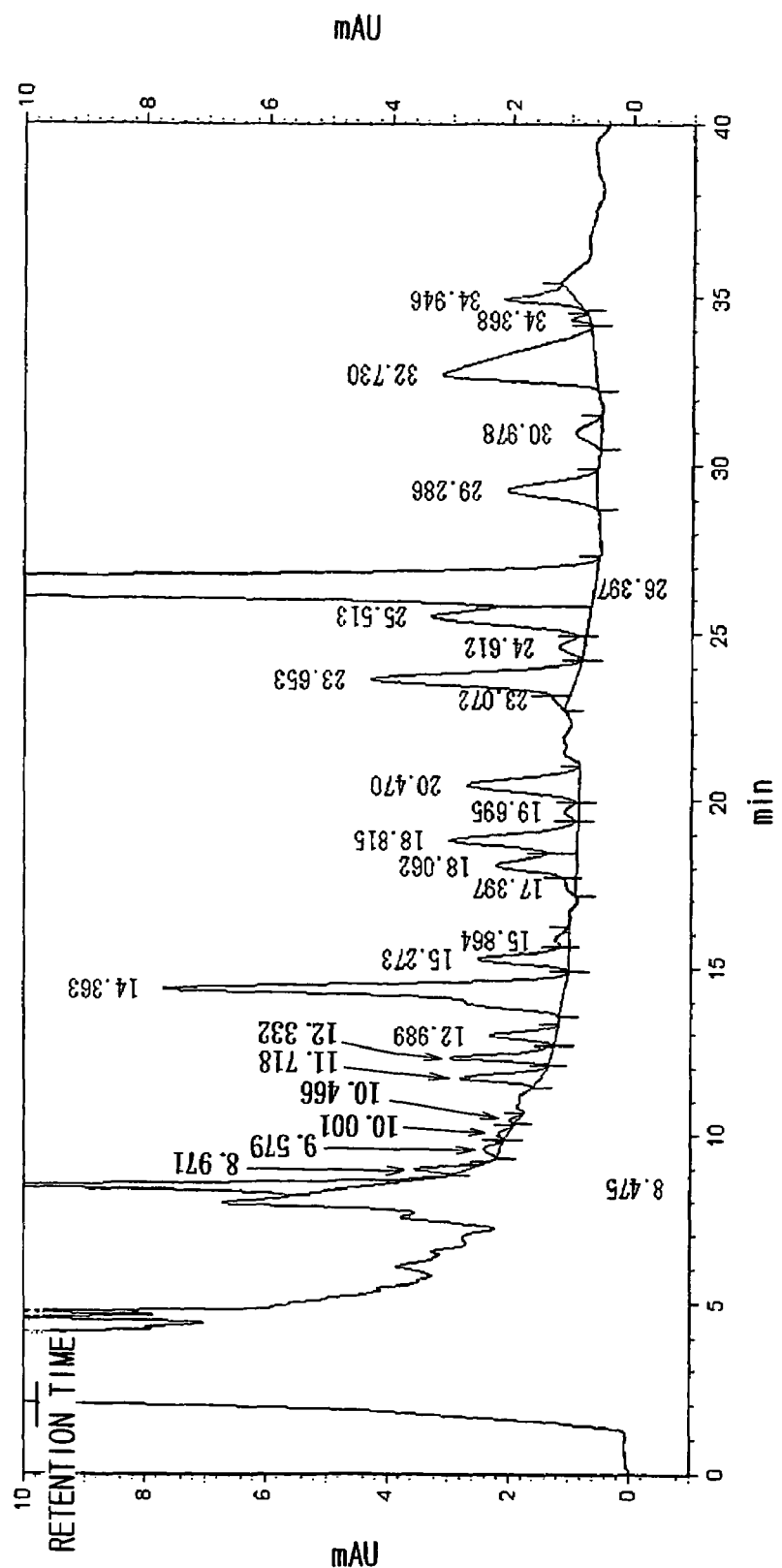

Conditions for HPLC analysis were as follows:
HPLC system—LC-10ADVP, Shimadzu Corp.
Column—Inertsil ODS-2, 4.6×250 mm
Mobile phase—Acetonitorile:water=70:30
Flow rate—1.0 ml/min
Column temperature—40° C.
Detector—UV visible detector SPD-M10AVP, Shimadzu Corp.
UV wavelength—272 nm As shown in FIG. 15, the extract from the transformant strain TF-57 exhibited the peak in the same retention time (20.520 min) with standard PF1022-220 (20.308 min). Further, HPLC analysis using a mixture of the extract derived from the transformant and the standard verified that the peaks derived from the extract and the standard perfectly matched (20.470 min). Measurements of mass spectra for the substances contained in the peak using an LC-MS system (a quadrapole-type bench top LC/MS system NAVIGATOR with aQa™, Thermoquest) agreed with that for the standard. From the result above, it was revealed that the transformant strain TF-57 produced a substance PF1022 derivative, PF1022-220.

Example 12

Cultivation of Transformant and Detection of PF1022-260

The transformant strain TF-57 selected in Example 10 was cultured under the conditions as described in Example 11. After incubation, the resulting cells were collected from a 500 ml portion of the culture by centrifugation and then extracted with 500 ml of methanol. The extract was concentrated by drying and redissolved in 2 ml of methanol. A 10 µl portion of the solution was subjected to HPLC analysis.

Figure 16B:
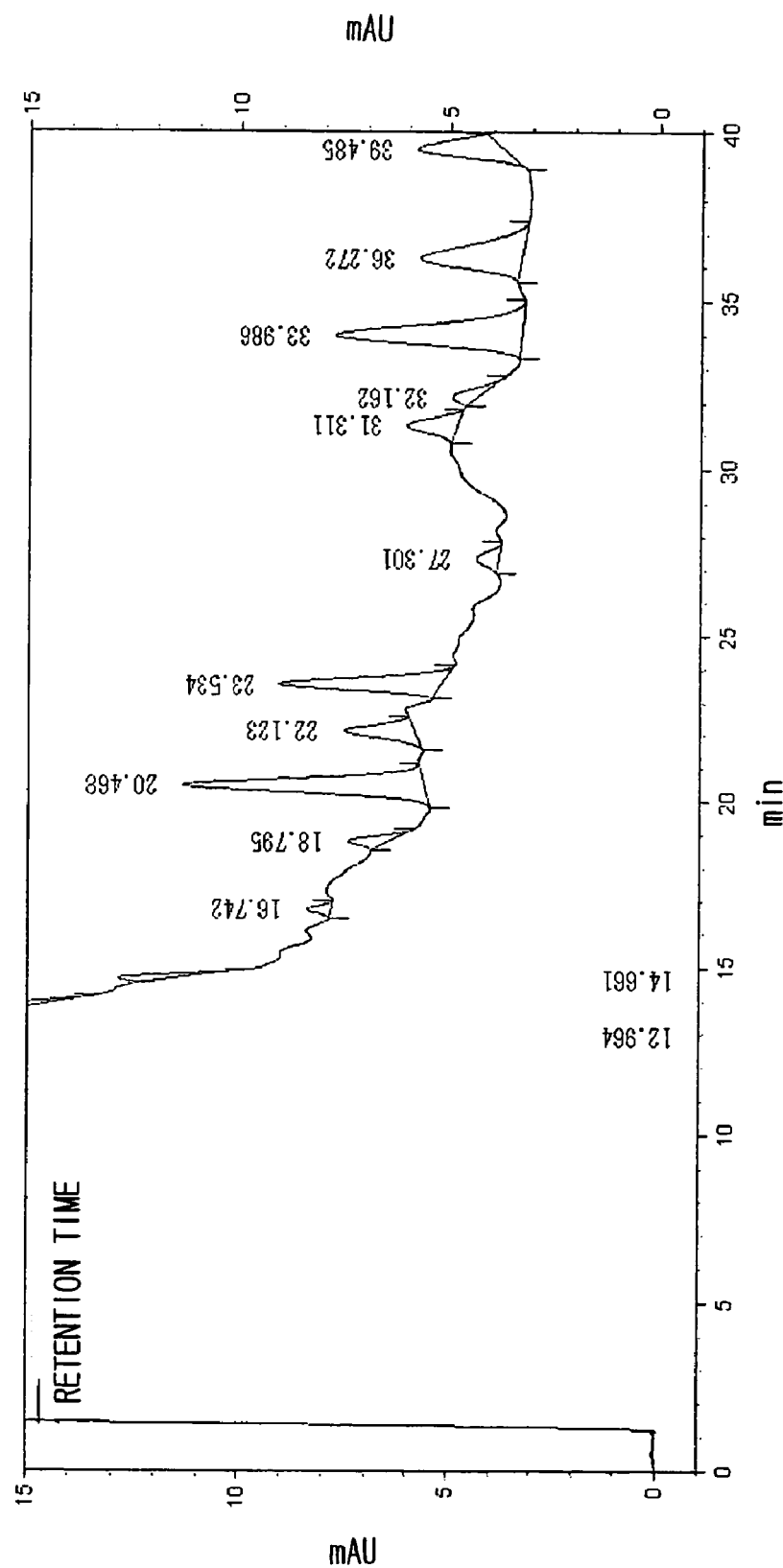
FIG. 16 shows the HPLC chromatograms used for detecting a substance PF1022 derivative, PF1022-260. A is the chromatogram for standard PF1022-260, and B is the chromatogram for the sample prepared from the transformant.

Conditions for HPLC analysis were as follows:
HPLC system—LC-10ADVP, Shimadzu Corp.
Column—Inertsil ODS-2, 4.6×250 mm
Mobile phase—Acetonitorile:water=55:45
Flow rate—1.0 ml/min
Column temperature—40° C.
Detector—UV visible detector SPD-M10AVP, Shimadzu Corp.
UV wavelength—245 nm As shown in FIG. 16, the extract from the transformant strain TF-57 exhibited the peak in the same retention time (27.301 min) with standard PF1022-260 (27.337 min). Measurements of mass spectra using an LC-MS system (a quadrapole-type bench top LC/MS system NAVIGATOR with aQa™, Thermoquest) for the substances contained in the peak agreed with that for the standard. From the result above, it was revealed that the transformant strain TF-57 produced a substance PF1022 derivative, PF1022-260.

Example 13

Partial Purification of Prephenate Dehydratase (PDT)

The PF1022 strain (FERM BP-2671) was cultured in the medium and under the conditions described in Example 11, after which the cells were recovered from about 700 ml of the resulting culture fluid by centrifugation (9,000×g, 30 minutes), the precipitate was suspended in a buffer solution for disruption (50 mM Tris-HCl (pH 8.0), 5 mM EDTA, 1 mM DTT, 1 mM PMSF, 20% glycerol) to wash the cells. Further, centrifuge was carried out (9000×g, 30 minutes) and the resulting precipitate was resuspended in 800 ml of the above-mentioned buffer solution for disruption to obtain a cell suspension.

The cell suspension was treated with ultrasonication (10 minutes, 3 times) and then centrifuged (9,000×g, 30 minutes, 2 times) to remove cell debris and a cell extract was obtained. This cell extract was subjected to Q Sepharose Fast Flow column chromatography (Amersham Pharmacia Biotech, 2.6×32 cm). The flow rate was 1 ml/min. The column was then washed with 540 ml of a buffer solution A (50 mM Tris-HCl (pH 8.0), 1 mM DTT, 20% glycerol). Further, proteins were eluted with a linear concentration gradient of 0-1.0 M sodium chloride using a total volume of 730 ml of the buffer solution A containing 1 M sodium chloride. Fractions of 20 ml were collected starting 300 minutes after the start of the concentration gradient, and each fraction was measured for PDT activity as follows: Namely, 20 µl of 2 mM barium prephenate (Sigma), 8 µl of 1 M Tris-HCl (pH 7.0), and 12 µl of an enzyme sample were mixed and held at 30° C. for 30 minutes, after which 360 µl of 1 N sodium hydroxide were added and the optical density was measured at 320 nm. As a result, high activity was detected in fractions 13-16 and these fractions were pooled to make a Q Sepharose fraction (80 ml).

Next, 19.36 g of ammonium sulfate were added to the whole volume of the Q Sepharose fraction, centrifugation was carried out (20,000×g, 15 minutes), and the resulting precipitate was removed to obtain supernatant. The supernatant was subjected to Butyl-Toyopearl 650S column chromatography (Toso, 1.6×25 cm). The flow rate was 1 ml/min. The column was washed with the buffer solution A containing 1.6 M ammonium sulfate, after which proteins were eluted with a linear concentration gradient of 1.6-0M ammonium sulfate using a total volume of 100 ml of the buffer solution A, and further with 50 ml of the buffer solution A. Fractions of 5 ml were collected starting 50 minutes after the start of the concentration gradient, and each fraction was measured for PDT activity. As a result, activity was detected in fractions 8-15 and these fractions were pooled to make a Butyl-Toyopearl fraction (40 ml).

13.48 g of ammonium sulfate were added to the whole volume of the Butyl-Toyopearl fraction and the resulting precipitate was recovered by centrifugation (20,000×g, 15 minutes). The precipitate was dissolved in 1 ml of a buffer solution B (50 mM sodium phosphate (pH 7.0), 1 mM DTT, 20% glycerol), subjected to a HiLoad 26/60 Superdex 200 pg (Amersham Pharmacia Biotech, 2.6×60 cm), and eluted using the buffer solution B. The flow rate was 1 ml/min. Fractions of 20 ml were collected over a period from 160 minutes to 220 minutes after charging the sample, each fraction was measured for PDT activity. As a result, activity was detected in fractions 4-8 and these fractions were pooled to make a Superdex 200 fraction (25 ml).

The whole volume of the Superdex 200 fraction was subjected to Macro-Prep Hydroxyapatite column chromatography (Bio-Rad, 0.5×20 cm) and eluted using the buffer solution B. The flow rate was 0.5 ml/min. Fractions of 2 ml were collected after charging the sample and each fraction was measured for PDT activity. As a result, activity was detected in fractions 2-25 and these fractions were pooled to make a Hydroxyapatite fraction (38 ml).

The whole volume of the Hydroxyapatite fraction was concentrated using a CENTRICON PLUS-20 (Millipore) and the resulting concentrate was applied onto a HiTrap Blue HP column (Amersham Pharmacia Biotech, 5 ml) and eluted with the buffer solution B. The flow rate was 1 ml/min. Fractions of 2 ml were collected after charging the sample and each fraction was measured for PDT activity. As a result, activity was detected in fractions 6-22 and these fractions were pooled to make a HiTrap Blue fraction (34 ml).

The whole volume of the HiTrap Blue fraction was concentrated using a CENTRICON PLUS-20 and a Microcon-10 (Amicon) and the resulting concentrate was applied onto a Superdex 75 HR column (Amersham Pharmacia Biotech, 1.0×30 cm) and then eluted with the buffer solution B. The flow rate was 0.25 ml/min. Fractions of 0.5 ml were collected starting 20 minutes after charging the sample and each fraction was measured for PDT activity. As a result, activity was detected in fractions 7-11. Accordingly, fractions 5-13 were analyzed using SDS-PAGE. Since the intensity of the resulting band of about 35 kDa agreed with the intensity of the enzyme activity, the protein obtained was identified as PDT.

Example 14

Determination of Partial Amino Acid Sequence of PDT (1) N-Terminal Amino Acid Sequence The active fraction obtained in Example 13 was subjected to SDS-PAGE (TEFCO) and the protein was electrically transferred onto a PVDF membrane (Immobilon-PSQ, Millipore) using a Multifor II (Amersham Pharmacia Biotech). The membrane was stained with Coomassie Brilliant Blue G250 (Nakarai Tesque), washed with water and dried in air. A band having a molecular weight of about 35 kDa was cut out from this membrane, and subjected to analysis of the N-terminal amino acid sequence using a protein sequencer Model 492 (Applied Biosystems). As a result, the following sequence was obtained. X shows an unidentified amino acid.
N-terminal amino acid sequence: GHTSAGDAGSKPVVX-FLGPISSY (23 residues) (SEQ ID NO: 28).

(2) Analysis of Internal Amino Acid Sequence (Peptide Mapping)

The active fraction purified in Example 13 was subjected to SDS-PAGE and stained with Coomassie Brilliant Blue R250 (Nakarai Tesque), and a band of about 35 kDa was cut out, completely destained at 30° C. in a 0.2 M ammonium bicarbonate buffer solution (pH 8.0) prepared in 50% acetonitrile, and dried in air at room temperature for 2 hours. Next, the resulting shrunken gel piece was moistened with a 0.2 M ammonium bicarbonate buffer solution (pH 8.0) containing 0.02% Tween 20 and then a 1/50 molar volume of trypsin (Promega) to the protein was added. The gel piece was allowed to stand at 37° C. for 10 minutes and then immersed in the abovementioned buffer solution, after which the reaction was carried out at 37° C. for 2 days. The supernatant after the reaction was recovered, and the decomposed product was further recovered from the gel piece with 60% acetonitrile and 0.1% trifluoroacetic acid and combined with the reaction supernatant. The resulting sample was concentrated and then subjected to column chromatography (RP-300 Aquapore C18, 220×2.1 mm, concentration gradient: 0.1% trifluoroacetic acid, 5% acetonitrile-0.085% trifluoroacetic acid, 35% acetonitrile) using a Model 172μ preparative HPLC system (Applied Biosystems) to fractionate four kinds of peptides. Sequences of the peptides obtained were determined by a protein sequencer.
T-19.4: GVETVDVSSTSR (12 residues) (SEQ ID NO: 29)
T-21.0: TLDHFADR (8 residues) (SEQ ID NO: 30)
T-33.4: FFVLR (5 residues) (SEQ ID NO: 31)
T-47.1: AFPLEQFDLMPVTTIK (16 residues) (SEQ ID NO: 32)

Example 15

Isolation of PDT Gene

Of the N-terminal amino acid sequence (SEQ ID NO: 28) determined in Example 14, the following 5' side primers were synthesized based on residues 4-9 of the amino acid sequence (PDTN-4,5,6).
PDTN-4: TCYGCNGGNGAYGCNGG (SEQ ID NO: 33)
PDTN-5: TCRGCNGGNGAYGCNGG (SEQ ID NO: 34)
PDTN-6: AGYGCNGGNGAYGCNGG (SEQ ID NO: 35)

Further, the following 3' side primers were synthesized based on residues 5-11 of the amino acid sequence of SEQ ID NO: 32.
PDTC-3: GGCATNARRTCRAAYTGYTC (SEQ ID NO: 36)

Using the abovementioned primers, PCR was carried out in combinations of PDTN-4×PDTC-3, PDTN-5×PDTC-3, and PDTN-6×PDTC-3. The PCR reaction was carried out with KOD Dash (Toyobo Co., Ltd.) as a template using a PERKIN ELMER GeneAmp PCR System 9700. A reaction solution contained 1 μl (equivalent to 1 μg) of the genomic DNA of the PF1022 strain (FERM BP-2671) prepared by the method described in Example 5, 5 μl of 10-fold concentrated reaction buffer attached to the enzyme, 5 μl of a 2 mM DNTP solution, 1 μl each of the abovementioned primers prepared at a concentration of 100 pmol/μl, 5 μl of dimethyl sulfoxide (special reagent grade, Wako Pure Chemical Industries, Ltd.), and 1 μl of KOD Dash, and. 31 μl of sterile water was added to make a total volume of 50 μl. The reaction was carried out by repeating 30 cycles of 30 seconds at 94° C., 30 seconds at 55° C., and 30 seconds at 74° C., after pretreatment at 94° C. for 5 minutes. The resulting reaction product was subjected to agarose gel electrophoresis for analysis. The result showed that a DNA fragment of approximately 200 bp was specifically amplified in combination of PDTN-6×PDTC-3.

Next, this DNA fragment of approximately 200 bp was excised from the agarose gel, extracted, purified, and then cloned using a TOPO TA cloning kit (Invitrogen). An inserted fragment of the resulting plasmid was analyzed for the base sequence using a fluorescent DNA sequencer ABI PRISM 310 Genetic Analyzer (Perkin-Elmer). As a result, it was revealed that the fragment encoded a sequence which partly agreed with the amino acid sequence determined from the N terminal and peptide, showing the resulting DNA fragment was a part of the PDT gene.

Figure 17:
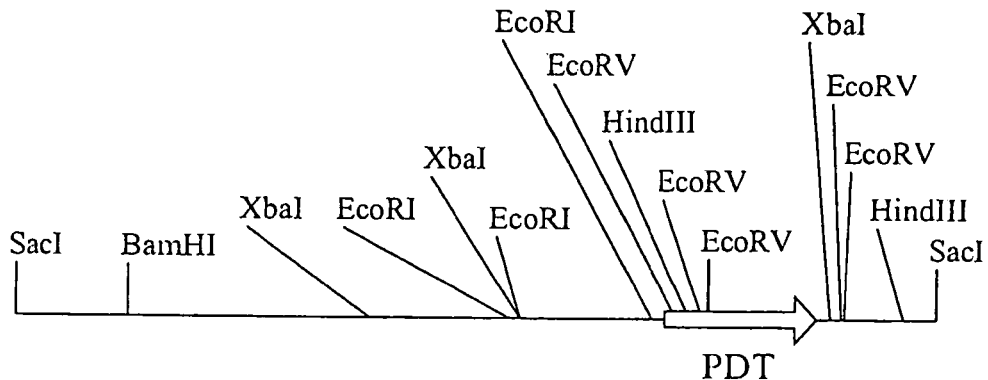
FIG. 17 shows the restriction map of a SacI fragment isolated from the genomic DNA of the PF1022 strain (FERM BP-2671) and the location of the PDT gene.

Accordingly, screening of the genomic library of the substance PF1022-producing microorganism prepared in Example 5 was carried out with this DNA fragment as a probe using an AlkPhos Direct Labelling and Detection System (Amersham Pharmacia Biotech). A phage DNA was extracted from the resulting positive clone and analyzed with restriction enzymes. As a result, it was revealed that an approximately 8.2-kbp SacI fragment was present as a DNA fragment to be hybridized with the abovementioned probe. Accordingly, this fragment was subcloned into pUC118 to obtain plasmid pUC-PDT. By using this plasmid, the nucleotide sequence was analyzed using an ABIPRISM 377 sequencer (Applied Biosystems). FIG. 17 shows the restriction enzyme map of the SacI fragment and the location of the PDT gene. The presence of two introns in the PDT gene was suggested by the nucleotide sequence analysis and was confirmed by the cDNA analysis. The nucleotide sequence of the PDT gene and the amino acid sequence deduced from this sequence are shown in SEQ ID NO: 37 and SEQ ID NO: 38, respectively. Of the nucleotide sequence in SEQ ID NO: 37, the base sequences 91-192 and 254-380 are introns.

Example 16

Construction of Plasmid for Disrupting PDT Gene of Substance PF1022-Producing Microorganism Plasmid pDPDT for disrupting the PDT gene was constructed as follows.

First, PCR was carried out using a commercially-available plasmid pUCSV-BSD (Funakoshi) containing a blasticidin S resistance gene (BSD) as a template and the oligonucleotides depicted in SEQ ID NO: 39 and SEQ ID NO: 40 as primers according to the method described in Example 2. After the reaction, a portion of the reaction solution was subjected to agarose gel electrophoresis, which confirmed that a DNA fragment of approximately 0.4 kbp was specifically amplified. Then, the remaining reaction solution was extracted with phenol:chloroform:isoamyl alcohol (25:24:1) and precipitated with ethanol. The precipitate was redissolved in sterile water, and 60 μl of the resulting solution were digested with restriction enzymes ClaI and BglII, after which agarose gel electrophoresis was carried out, and a band of approximately 0.4 kbp was cut out according to an ordinary method to recover the DNA fragment.

Next, plasmid pDHBAR (Watanabe, M. et al., Appl. Environ. Microbiol., 65, 1036-1044 (1999)) was digested with restriction enzymes ClaI and BamHI, after which agarose gel electrophoresis was carried out and a band of approximately 2 kbp was cut out according to an ordinary method to recover the DNA fragment. This DNA fragment and the abovementioned fragment of approximately 0.4 kbp were ligated to obtain plasmid pDHBSD. This plasmid was digested with restriction enzyme XbaI and the terminals were blunted using a DNA Blunting Kit (Takara Shuzo Co., Ltd.), after which agarose gel electrophoresis was carried out and a band of approximately 2.4 kbp was cut out according to an ordinary method to recover the DNA fragment.

Figure 18:
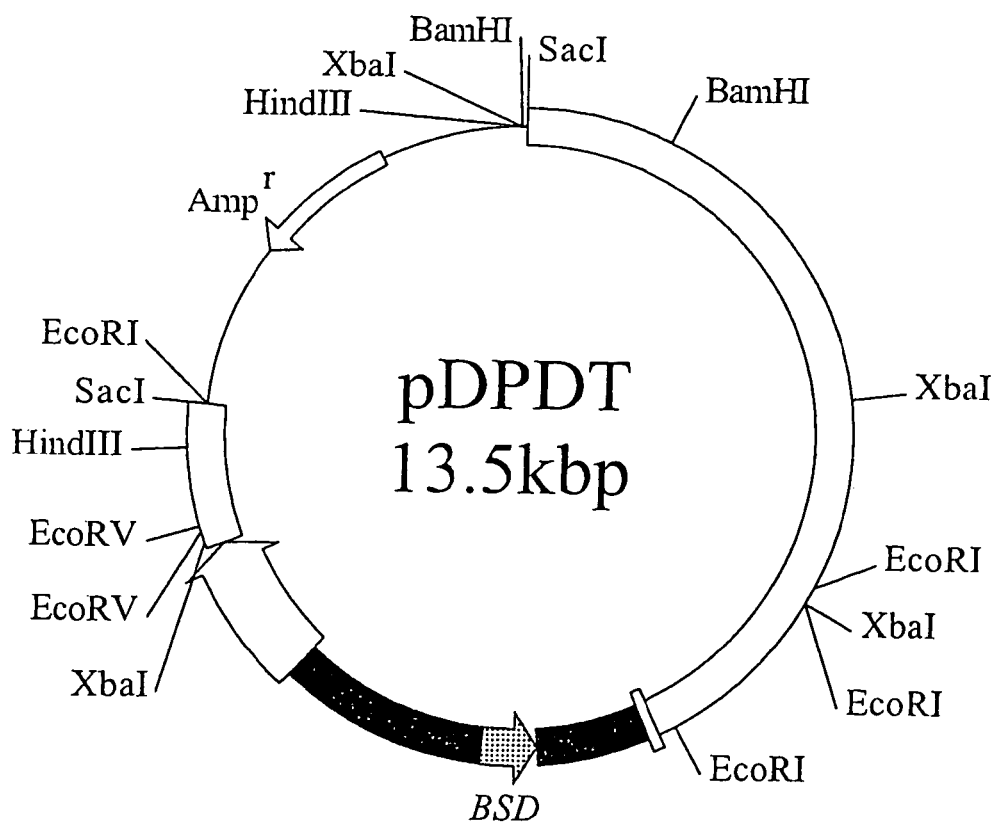
FIG. 18 shows the restriction map of plasmid pDPDT.

Next, the plasmid pUC-PDT described in Example 15 was partially digested with restriction enzyme EcoRV, after which a DNA fragment of approximately 11.1 kbp was cut out according to an ordinary method to recover the DNA fragment. This DNA fragment and the above-mentioned fragment of approximately 2.4 kbp were ligated to obtain plasmid pDPDT (FIG. 18).

Example 17

Disruption of PDT Gene of Substance PF1022-Producing Microorganism

The plasmid pDPDT described in Example 16 was digested with restriction enzyme SacI, and then dissolved in a TE buffer solution (10 mM Tris-HCl (pH 8.0), 1 mM EDTA) to make a final concentration of 1 μg/μl. Strain TF-57 described in Example 10 was transformed with this DNA solution by the method described in Example 9. In this case, 100 μg/ml blasticidin S was used as a selectable drug for transformants instead of hygromycin B.

About 100 strains of the resulting transformants were each cultured under the conditions described in Example 5, centrifuged, collected and then suspended in a buffer solution for disruption (50 mM Tris-HCl (pH 8.0), 5 mM EDTA, 1 mM DTT, 1 mM PMSF, 10% glycerol). This suspension was subjected to ultrasound treatment, centrifuged to recover supernatant to obtain the cell extract. PDT activity was measured for this cell extract by the method described in Example 13. As a result, it was revealed that no PDT activity was detected in 5 strains and these strains lacked the PDT activity.

Figure 19B:
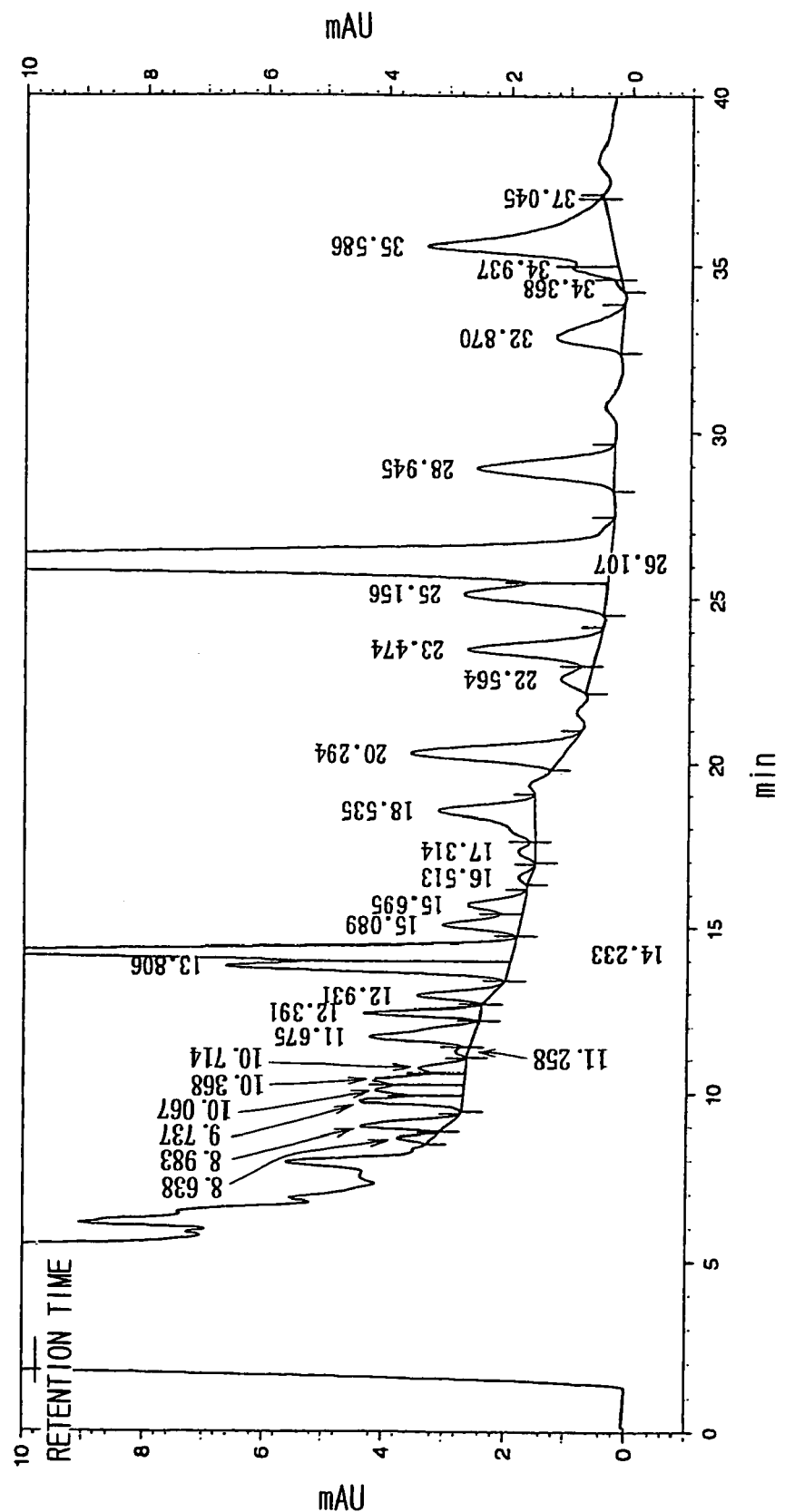
FIG. 19 shows the HPLC chromatograms used for detecting a substance PF1022 derivative, PF1022-220. A is the chromatogram for the sample prepared from strain TF-57, and B is the chromatogram for the sample prepared from strain TF-45.

Of these strains, strain TF-45 was selected and cultured along with a parent strain, TF-57, by the method described in Example 11 to detect PF1022-220. The result is shown in FIG. 19. PF1022-220 was detected at the position of 20.303 minutes for strain TF-57 and 20.294 minutes for strain TF-45. The peak area was about 4 times larger in strain TF-45 than strain TF-57. From the result above, it was revealed that PF1022-220 productivity was improved by impairing the PDT activity.

---

The invention claimed is:

1. An isolated transformant producing a substance PF1022 derivative, said transformant is produced by introducing genes involved in a biosynthetic pathway from chorismic acid to p-aminophenylpyruvic acid into a phenylalanine auxotrophic host induced from an organism that produces substance PF1022 ([cyclo(D-lactyl-L-N-methylleucyl-D-3phenyllactyl-L-N-methylleucyl)-D-lactyl-L-N-methylleucyl-D-3-phenyllactyl-L-N-methylleucyl)]) represented by formula (I):

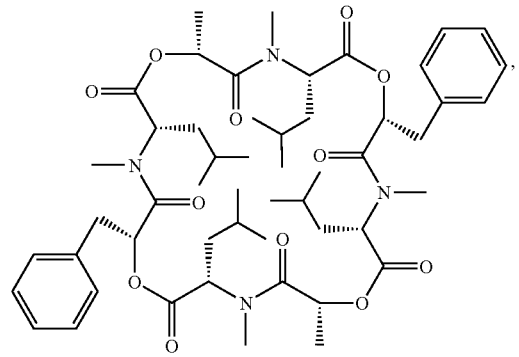

wherein said genes comprise:

(1) a gene encoding 4-amino-4-deoxychorismate synthase, which gene comprises the DNA sequence encoding the amino acid sequence of SEQ ID NO: 2;

(2) a gene encoding 4-amino-4-deoxychorismate mutase, which gene comprises the DNA sequence encoding the amino acid sequence of SEQ ID NO: 4; and (3) a gene encoding 4-amino-4-deoxyprephenate dehydrogenase, which gene comprises the DNA sequence encoding the amino acid sequence of SEQ ID NO: 6, and wherein the substance PF1022 derivative is a compound of formula (III) ([cyclo(D-lactyl-L-N-methylleucyl-D-3-(4-nitrophenyl)lactyl-L-N-methylleucyl-D-lactyl-L-N-methylleucyl-D-3-(4-nitrophenyl)lactyl-L-N-methylleucyl)]) represented by the following formula:

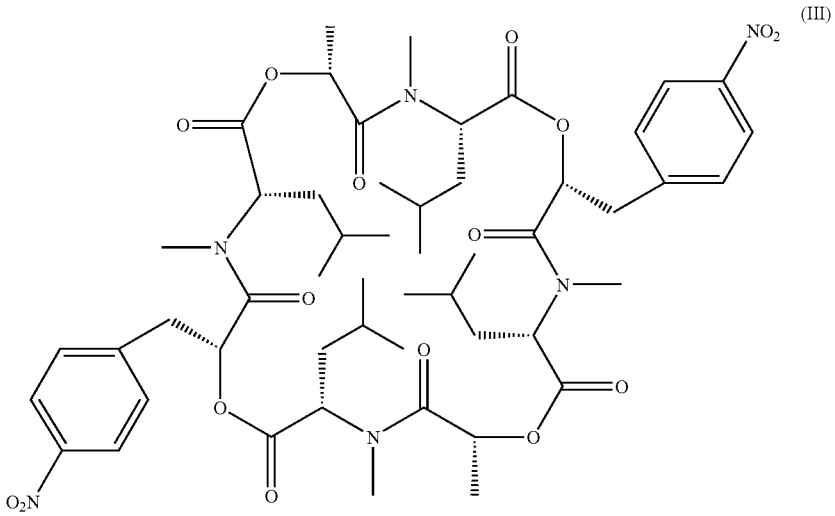

or a compound of formula (V) ([cyclo(D-lactyl-L-N-methylleucyl-D-3-(4-aminophenyl)lactyl-L-N-methylleucyl-D-lactyl-L-N-methylleucyl-D-3-(4-aminophenyl)lactyl-L -N-methylleucyl)]) represented by the following formula:

(V)

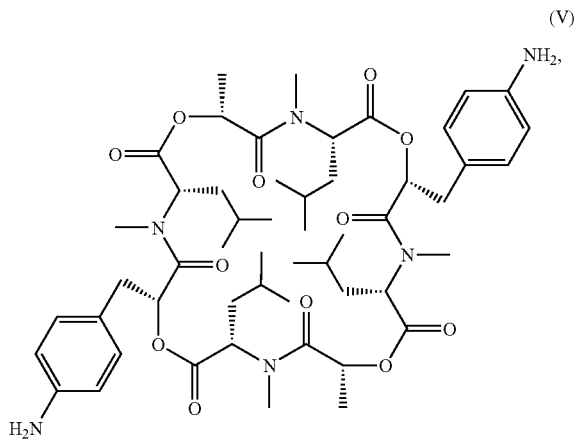

wherein the phenylalanine auxotrophic host is obtained from *Mycelia sterilia* by disrupting an endogenous chorismate mutase gene encoding the amino acid sequence of SEQ ID NO: 27 and/or a prephenate dehydratase gene encoding the amino acid sequence of SEQ ID NO: 38 by homologous recombination, "so as to reduce endogenous chorismate mutase and/or prephenate degydratase activity" wherein the Mycelia sterilia is the strain deposited with the National Institute of Advanced Industrial Science and Technology under an accession number of FERM BP-2671.

2. The transformant according to claim 1, wherein the phenylalanine auxotrophic host lacks endogenous chorismate mutase activity and/or prephenate dehydratase activity.

3. The transformant according to claim 1, wherein at least one of the genes is a gene from genus Streptomyces.

4. The transformant according to claim 1, wherein the gene encoding 4-amino-4-deoxychorismate synthase comprises the DNA sequence of SEQ ID NO: 1.

5. The transformant according to claim 1, wherein the gene encoding 4-amino-4-deoxychorismate mutase comprises the DNA sequence of SEQ ID NO: 3.

6. The transformant according to claim 1, wherein the gene encoding 4-amino-4-deoxyprephenate dehydrogenase comprises the DNA sequence of SEQ ID NO: 5.

7. The transformant according to claim 1, wherein the gene encoding 4-amino-4-deoxychorismate synthase, the gene encoding 4-amino-4-deoxychorismate mutase, and the gene encoding 4-amino-4-deoxyprephenate dehydrogenase comprise the DNA sequence of SEQ ID NO: 1, the DNA sequence of SEQ ID NO: 3, and the DNA sequence of SEQ ID NO: 5, respectively.

8. A method for producing a substance PF1022 derivative, which comprises the steps of culturing the transformant of claim 1 and collecting a substance PF1022 derivative.

9. The method for producing a substance PF1022 derivative according to claim 8, wherein the substance PF1022 derivative is a compound of formula (III):

(III)

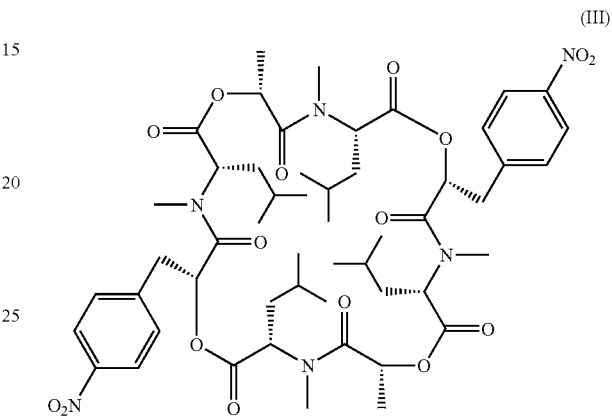

or a compound of formula (V):

(V)

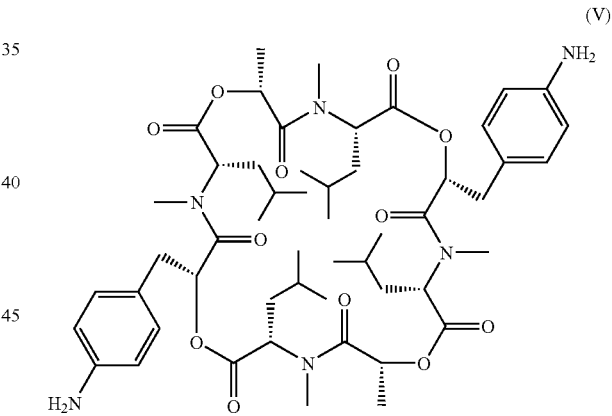

* * * * *